(12) United States Patent
van Loevezijn et al.

(10) Patent No.: US 9,126,942 B2
(45) Date of Patent: Sep. 8, 2015

(54) ARYLSULFONYL PYRAZOLINE CARBOXAMIDINE DERIVATIVES AS 5-HT$_6$ ANTAGONISTS

(71) Applicant: AbbVie Bahamas Limited, New Providence, Nassau (BS)

(72) Inventors: Arnold van Loevezijn, Weesp (NL); Wouter I. Iwema Bakker, Weesp (NL); Alex Stoit, Weesp (NL); Agatha M. Rensink, CP Weesp (NL); Jennifer Venhorst, CP Weesp (NL); Martina A.W. Van Der Neut, CP Weesp (NL); Martin De Haan, CP Weesp (NL); Cornelis G. Kruse, CP Weesp (NL)

(73) Assignee: ABBVIE BAHAMAS LIMITED, Nassau (BS)

( * ) Notice: Subject to any disclaimer, the term of this patent is extended or adjusted under 35 U.S.C. 154(b) by 0 days.

(21) Appl. No.: 14/527,651

(22) Filed: Oct. 29, 2014

(65) Prior Publication Data

US 2015/0051239 A1    Feb. 19, 2015

Related U.S. Application Data

(63) Continuation of application No. 14/024,030, filed on Sep. 11, 2013, now Pat. No. 8,901,108, which is a continuation of application No. 12/933,182, filed as application No. PCT/EP2009/053133 on Mar. 18, 2008, now Pat. No. 8,563,723.

(30) Foreign Application Priority Data

Mar. 8, 2008  (EP) .................... 08152873

(51) Int. Cl.
| | |
|---|---|
| C07D 231/06 | (2006.01) |
| C07D 231/54 | (2006.01) |
| C07D 403/12 | (2006.01) |
| C07D 491/10 | (2006.01) |
| A61K 31/415 | (2006.01) |
| A61K 31/4155 | (2006.01) |
| A61K 31/635 | (2006.01) |
| A61K 45/06 | (2006.01) |
| C07D 471/10 | (2006.01) |
| C07D 491/107 | (2006.01) |
| A61K 31/4162 | (2006.01) |
| A61K 31/435 | (2006.01) |
| C07D 231/00 | (2006.01) |

(52) U.S. Cl.
CPC ............ *C07D 231/06* (2013.01); *A61K 31/415* (2013.01); *A61K 31/4155* (2013.01); *A61K 31/4162* (2013.01); *A61K 31/435* (2013.01); *A61K 31/635* (2013.01); *A61K 45/06* (2013.01); *C07D 231/00* (2013.01); *C07D 231/54* (2013.01); *C07D 403/12* (2013.01); *C07D 471/10* (2013.01); *C07D 491/10* (2013.01); *C07D 491/107* (2013.01)

(58) Field of Classification Search
None
See application file for complete search history.

(56) References Cited

U.S. PATENT DOCUMENTS 7,728,018 B2    6/2010   Van Loevezijn et al.

FOREIGN PATENT DOCUMENTS

| WO | WO 03/026648 A | 4/2003 |
|---|---|---|
| WO | WO 2006/308006 A | 4/2006 |
| WO | WO 2008/034863 A | 3/2008 |

OTHER PUBLICATIONS

Woolley et al., 5-HT6 Receptors, Current Drug Targets—CNS & Neurological Disorders, 59-79 (2004).*
International Search Report and Written Opinion dated Apr. 22, 2009, corresponding to PCT/EP2009/053133.
Castañeda-Corral, G. et al., "Role of Peripheral and Spinal 5-HT$_6$ Receptors According to the Rat Formalin Test", *Neuroscience*, 162 (2009) 444-452.
De Bruin, N.M.W.J. et al., "A novel highly selective 5-HT$_6$ receptor antagonist attenuates ethanol and nicotine seeking but does not affect inhibitory response control in Wistar rats", *Behavioural Brain Research*, 236 (2013) 157-165.

(Continued)

*Primary Examiner* — Timothy R Rozof
(74) *Attorney, Agent, or Firm* — Finnegan, Henderson, Farabow, Garrett & Dunner LLP

(57) ABSTRACT

This invention concerns arylsulfonyl pyrazoline carboxamidine derivatives as antagonists of 5-ht6 receptors, to methods for the preparation of these compounds and to novel intermediates useful for their synthesis. The invention also relates to the uses of such compounds and compositions, particularly their use in administering them to patients to achieve a therapeutic effect in Parkinson's disease, Huntington's chorea, schizophrenia, anxiety, depression, manic depression, psychoses, epilepsy, obsessive compulsive disorders, mood disorders, migraine, Alzheimer's disease, age related cognitive decline, mild cognitive impairment, sleep disorders, eating disorders, anorexia, bulimia, binge eating disorders, panic attacks, akathisia, attention deficit hyperactivity disorder, attention deficit disorder, withdrawal from abuse of cocaine, ethanol, nicotine or benzodiazepines, pain, disorders associated with spinal trauma or head injury, hydrocephalus, functional bowel disorder, irritable bowel syndrome, obesity and type-2 diabetes. The compounds have the general formula (1) wherein the symbols have the meanings given in the description.

21 Claims, No Drawings

(56) References Cited

OTHER PUBLICATIONS

Freitas, Renato Leonardo et al., "5-HT$_{1A/1B}$, 5-HT$_6$ and 5-HT$_7$ serotonergic receptors recruitment in tonic-clonic seizure-induced antinociception: Role of dorsal raphe nucleus", *Experimental Neurology*, 217 (2009) 16-24.
Meltzer, Herbert Y., "The Role of Serotonin in Antipsychotic Drug Action", *Neuropsychopharmacology*, 1999, vol. 21, No. 2S.
Schechter, Lee E. et al., "Neuropharmacological Profile of Novel and Selective 5-HT$_6$ Receptor Agonists: WAY-181167 and WAY-208466", *Neuropsychopharmacology*, (2008); 33. 1323-1335.
Van Gaalen, Marcel M. at al., "5-HT$_8$ antagonism attenuates cue-induced relapse to cocaine seeking without affecting cocaine reinforcement", *International Journal of Neuropsychopharmacology*, vol. 13, Issue 07, Aug. 2010, pp. 961-965.
Benes, F.M. et al., Acute amygdalar activation induces an upregulation of multiple monoamine G protein coupled pathways in rat hippocampus; Molecular Psychiatry (2004); vol. 9, pp. 932-945.
Castañeda-Corral, G. et al.; Role of Peripheral and Spinal 5-HT$_6$ Receptors According to the Rat Formalin Test; Neuroscience (2009); vol. 162; pp. 444-452.
De Bruin, N.M.W.J. et al.; A novel highly selective 5-HT$_6$ receptor antagonist attenuates ethanol and nicotine seeking but does not affect inhibitory response control in Wistar rats; Behavioural Brain Research (2013); vol. 236; pp. 157-165.
Finn, David P. et al; The effects of pharmacological blockade of the 5-HT$_6$ receptor on formalin-evoked nociceptive behavior, locomotor activity and hypothalamo-pituitary-adrenal axis activity in rats; European Journal of Pharmacology (2007); vol. 569; pp. 59-63.
Heal, D.J. et al.; Selective 5-HT$_6$ receptor ligands: Progress in the development of a novel pharmacological approach to the treatment of obesity and related metabolic disorders; Pharmacology & Therapeutics (2008) vol. 117; pp. 207-231.
Meltzer, Herbert Y.; The Role of Serotonin in Antipsychotic Drug Action; Neuropsychopharmacology (1999); vol. 21, No. 2S; pp. 106S-115S.
Moriarty, Stephen R. et al.; Selective 5-HT$_{2A}$ and 5-HT$_6$ Receptor Antagonists Promote Sleep in Rats; Sleep (2008); vol. 31, No. 1; pp. 34-44.
Pullagurla, Manik et al.; Modulation of the stimulus effects of (+)amphetamine by the 5-HT$_6$ antagonist MS-245; Pharmacology, Biochemistry and Behavior (2004); vol. 78; pp. 263-268.
Van Gaalen, Marcel M. et al.; 5-HT$_6$ antagonism attenuates cue-induced relapse to cocaine seeking without affecting cocaine reinforcement; International Journal of Neuropsychopharmacology (2010); vol. 13; pp. 961-965.
Wesolowska, Anna et al.; Anxiolytic-like and antidepressant-like effects produced by the selective 5-HT$_6$ receptor antagonist SB-258585 after intrahippocampal administration to rats; Behavioural Pharmacology (2007); vol. 18, Nos. 5&6; pp. 439-446.
Young, Richard et al.; Effect of the 5-HT$_6$ serotonin antagonist MS-245 on the actions of (−)nicotine; Pharmacology, Biochemistry and Behavior (2006) vol. 85; pp. 170-177.

\* cited by examiner

ARYLSULFONYL PYRAZOLINE CARBOXAMIDINE DERIVATIVES AS 5-HT$_6$ ANTAGONISTS

This application is a continuation application of U.S. patent application Ser. No. U.S. patent application No. 14/024,030, filed on Sep. 11, 2013, which is a continuation of U.S. patent application Ser. No. 12/933,182, filed on Nov. 12, 2010, issued as U.S. Pat. No. 8,563,723, on Oct. 22, 2013, which is a national stage entry, under 35 U.S.C. §371, of PCT/EP2009/053133, filed Mar. 17, 2009, which claims the benefit of EP Application No. 08152873.9, filed Mar. 18, 2008, and U.S. Provisional Application No. 61/037,463, filed Mar. 18, 2008, the disclosures of all of which are incorporated herein by reference in their entirety.

TECHNICAL FIELD

This invention relates to the fields of pharmaceutical and organic chemistry, and provides arylsulfonyl pyrazoline carboxamidine derivatives, intermediates, formulations and methods.

BACKGROUND ART

Serotonin (5-hydroxytryptamine or 5-HT), a key transmitter of the peripheral and central nervous system, modulates a wide range of physiological and pathological functions, mediated through a number of receptor families termed 5-HT$_1$, 5-HT$_2$, 5-HT$_3$, 5-HT$_4$, 5-HT$_5$, 5-HT$_6$ and 5-HT$_7$. Although the functions of the latter three are less well understood than those of the others, it is generally accepted that compounds which selectively interfere with 5-HT-mediated signal transduction are important novel drug targets.

The rat 5-HT$_6$ receptor was cloned by two different groups (Ruat, 1993; Sebben, 1994), and that of the human, sharing a 89% sequence identity, shortly thereafter (Kohen, 1996). Much of the recent interest in the 5-HT$_6$ receptor is because several psychotropic agents are high affinity antagonists at the human 5-HT$_6$ receptor (Kohen, 1996; Roth, 1994). These compounds include amitriptyline ($K_i$=65 nM) and the atypical antipsychotics clozapine ($K_i$=9.5 nM), olanzapine ($K_i$=10 nM), and quetiapine ($K_i$=33 nM). None of these compounds, however, is selective. The first selective 5-HT$_6$ receptor antagonists reported are Ro 04-6790 and Ro 63-0563. Their usefulness is limited by their moderate affinity ($K_i$=50 nM and 12 nM, respectively) and poor pharmacokinetics (Sleight, 1998). With the recent development of the selective 5-HT$_6$ receptor antagonists Ro-04-6790 and SB-271046, there have been several reports on the activity of these compounds in models of cognitive function. SB-271046 improved performance in the Morris water maze (Rogers, 1999). These results are consistent with the finding that chronic intracerebroventricular administration of antisense oligonucleotides directed toward the 5-HT$_6$ receptor sequence led to improvements in some measures of performance in the Morris water maze (Bentley, 1999[b]). Recently, the effect of 5-HT$_6$ antagonists and 5-HT$_6$ antisense oligonucleotides to reduce food intake in rats has been reported (Bentley, 1997; Bentley, 1999[a]; Woolley, 2001). Obesity is a condition characterized by an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and type-2 diabetes.

5-HT$_6$ selective ligands have been identified as potentially useful in the treatment or prophylaxis of certain disorders of the central nervous system such as Parkinson's disease, Huntington's chorea and/or schizophrenia, anxiety, depression, manic depression, psychoses, epilepsy, obsessive compulsive disorders, mood disorders, migraine, Alzheimer's disease (enhancement of cognitive memory), age related cognitive decline, mild cognitive impairment, neurodegenerative diseases characterized by impaired neuronal growth, sleep disorders, feeding disorders such as anorexia and bulimia, binge eating disorders, panic attacks, akathisia, attention deficit hyperactivity disorder (ADHD), attention deficit disorder (ADD), withdrawal from drug abuse such as cocaine, ethanol, nicotine and benzodiazepines, and pain, and also disorders associated with spinal trauma and/or head injury such as hydrocephalus. 5-HT$_6$ selective ligands are also expected to be of use in the treatment of certain gastrointestinal disorders such as functional bowel disorder and Irritable Bowel Syndrome and in the treatment or prophylaxis of obesity and type-2 diabetes, to achieve reduction of body weight and of body weight gain. The reduction of body weight and of body weight gain (e.g. treating body-weight disorders) is achieved inter alia by reduction of food intake.

The goal of the present invention was to provide potent and selective 5-HT$_6$ antagonists, metabolically more stable than known, chemically related, 5-HT$_6$ antagonists (as disclosed in WO 2008/034863), compounds useful for the treatment of certain CNS disorders.

DISCLOSURE

Surprisingly it was found that certain arylsulfonyl pyrazoline carboxamidine derivatives bearing a H-bond donor functionality on or in the arylsulfonyl moiety, are 5-HT$_6$ receptor antagonists, more potent, and metabolically more stable than known, chemically related, 5-HT$_6$ antagonists. The invention relates to a compound of the general formula (1):

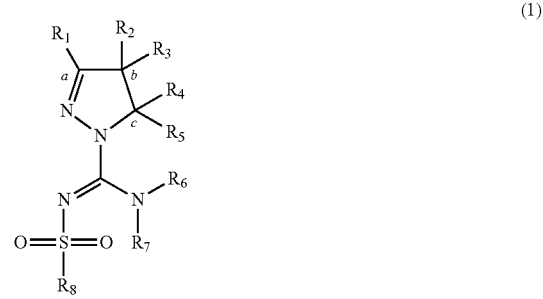

or a tautomer, stereoisomer, N-oxide, or a pharmacologically acceptable salt of any of the foregoing, wherein:

$R_1$ is chosen from hydrogen or an alkyl($C_{1-4}$) group, optionally substituted with one or more halogen atoms or an hydroxyl group, $R_2$ and $R_3$ are independently chosen from hydrogen, an hydroxyl group or an alkyl($C_{1-4}$) group optionally substituted with one or more substituents Q, independently chosen from: halogen, alkyl($C_{1-4}$), alkenyl($C_{1-4}$), alkynyl($C_{1-4}$), $CF_3$, $NH_2$, NHalkyl($C_{1-4}$), N[alkyl($C_{1-4}$)]$_2$, OH, =O, O-alkyl($C_{1-4}$), or $OCF_3$, or, $R_1$ and $R_2$, together with the carbon atoms marked 'a' and 'b' form a $C_{5-8}$-cycloalkyl ring, optionally substituted with one or more halogen atoms, an hydroxyl group or an alkyl($C_{1-4}$) group, or, $R_2$ and $R_3$, together with the carbon atom marked 'b' form a $C_{3-8}$-cycloalkyl or a $C_{4-8}$-heterocycloalkyl ring, optionally substituted with one or more substituents Q, as defined above, $R_4$ and $R_5$ are independently chosen from hydrogen or an alkyl($C_{1-4}$) group optionally substituted with one or more substituents Q, as defined above, or, $R_4$ and $R_5$ are independently chosen from a monocyclic or fused bicyclic aromatic or hetero-aromatic group, optionally substituted with one or more substituents Q, as defined above, with the proviso that Q cannot be =O (keto) on aromatic rings, or $R_3$ and $R_4$, together with the carbon atoms marked 'b' and 'c' form a $C_{3-8}$-cycloalkyl or a $C_{5-8}$-heterocycloalkyl ring, optionally substituted with one or more substituents Q, as defined above, $R_6$ and $R_7$ are independently chosen from hydrogen, or an alkyl($C_{1-4}$) group optionally substituted with one or more halogen atoms or an hydroxyl group, or a dialkyl($C_{1-3}$)-amino-alkyl($C_{1-3}$) group, or, $R_6$ and $R_7$ independently are chosen from a monocyclic or fused bicyclic aromatic or hetero-aromatic group optionally substituted with one or more substituents Q, as defined above, or, $R_6$ and $R_7$ independently are a $C_{5-8}$-cycloalkyl group or a $C_{5-8}$-heterocycloalkyl group optionally substituted with one or more substituents Q, as defined above, or, $R_6$ and $R_7$, together with the nitrogen atom to which they are attached, form a $C_{5-8}$-heterocycloalkyl group optionally substituted with one or more substituents Q, as defined above, $R_8$ is chosen from:

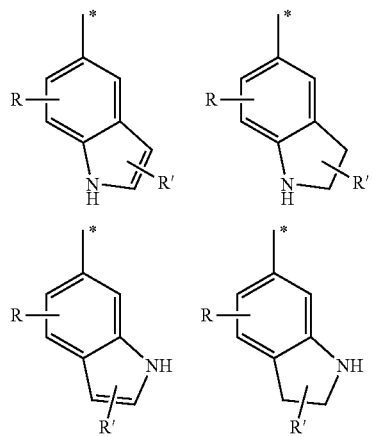

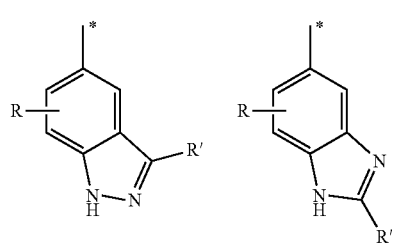

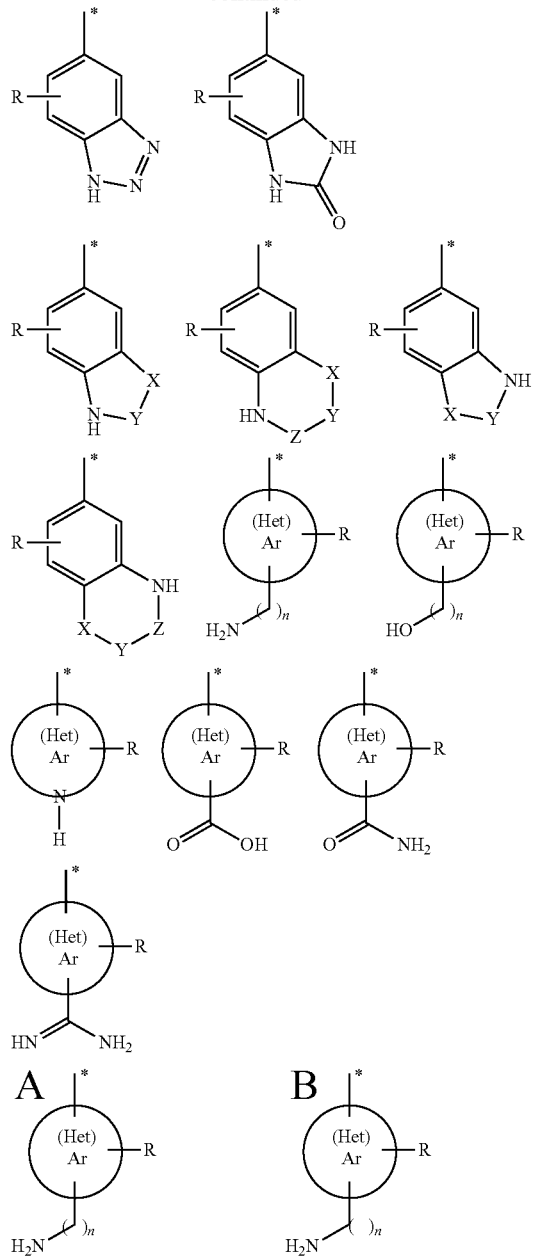

wherein:
the asterisk (*) marks the bond to the S-atom,
n is either 0 (zero) or 1,

is an aryl or heteroaryl group,
X, Y and Z are independently chosen from C, N, O or S, with the understanding that bonds in the ring containing X, Y or Z can be single or double, and C and N are substituted with H-atoms only,
R and R' are independently chosen from halogen, alkyl($C_{1-4}$), alkenyl($C_{1-4}$), alkynyl($C_{1-4}$), $CF_3$, $NH_2$, NHalkyl($C_{1-4}$), N[alkyl($C_{1-4}$)]$_2$, OH, SH, keto, O-alkyl ($C_{1-4}$), S-alkyl($C_{1-4}$), SO-alkyl($C_{1-4}$), SO$_2$-alkyl($C_{1-4}$), OCF$_3$, nitro and cyano, with the proviso that when $R_1$, $R_3$, $R_4$, $R_5$ and $R_6$ are hydrogen, $R_2$ and $R_7$ are ethyl, and $R_8$ is either 4-aminophenyl or 3-chloro-4-aminophenyl, the compounds are not racemic mixtures but pure enantiomers (both racemic mixtures were disclosed in WO 2008/034863).

The invention relates to racemates, mixtures of diastereomers as well as the individual stereoisomers of the compounds having formula (1). The invention also relates to the E isomer, Z isomer and E/Z mixtures of compounds having formula (1).

The invention particularly relates to a compound of the general formula (1) or a tautomer, stereoisomer, N-oxide, or a pharmacologically acceptable salt of any of the foregoing, wherein:

$R_1$, $R_4$ and $R_6$ are hydrogen $R_2$ and $R_3$ are independently chosen from hydrogen, an hydroxyl group or an alkyl($C_{1-4}$) group, optionally substituted with one or more substituents Q*, independently chosen from: halogen, alkyl($C_{1-4}$), NH$_2$, NHalkyl($C_{1-4}$), N[alkyl($C_{1-4}$)]$_2$ or OH, or $R_2$ and $R_3$, together with the carbon atom to which they are attached, form a $C_{3-8}$-cycloalkyl or a $C_{5-8}$-heterocycloalkyl ring optionally substituted with one or more substituents Q* as defined above, $R_5$ is chosen from hydrogen or an alkyl($C_{1-4}$) group, optionally substituted with one or more substituents Q* as defined above, or a monocyclic aromatic or heteroaromatic group optionally substituted with one or more substituents Q* as defined above, $R_7$ is chosen from hydrogen, or an unsubstituted alkyl($C_{1-4}$) group, optionally substituted with one or more halogen atoms or an hydroxyl group, $R_8$ is chosen from:

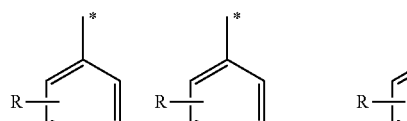

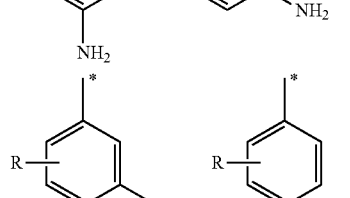

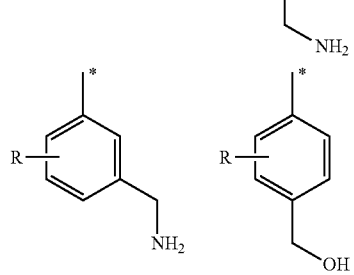

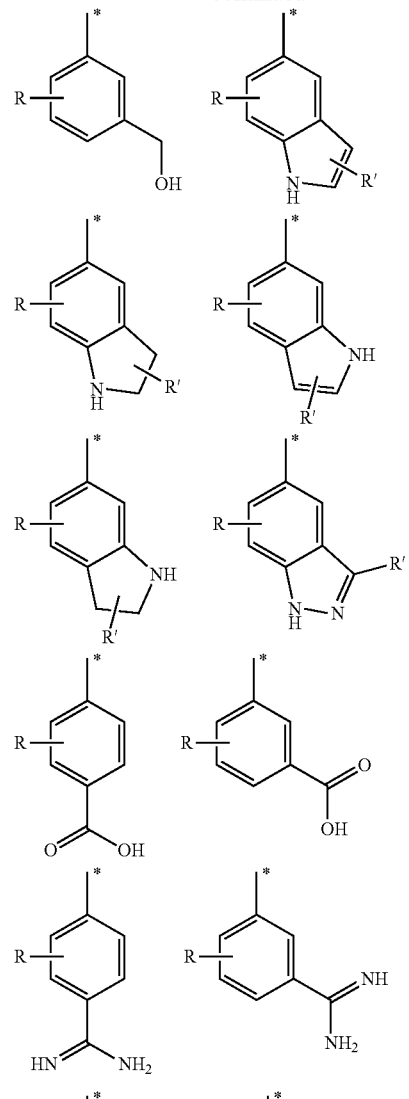

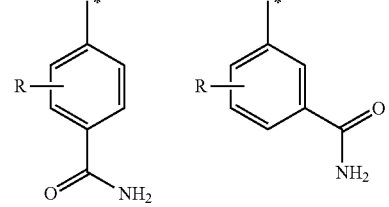

wherein the symbols have the same meanings as given in claim 1, with the proviso that when $R_3$ and $R_5$ are hydrogen, $R_2$ and $R_7$ are ethyl, and $R_8$ is either 4-aminophenyl or 3-chloro-4-aminophenyl, the compounds are not racemic mixtures but pure enantiomers.

In another embodiment the invention relates to compounds of formula (1) wherein either one, or both, of the two potentially asymmetric carbon atoms in the pyrazoline ring is the levorotatory or dextrorotatory enantiomer.

The compounds of the invention of formula (1), as well as the pharmacologically acceptable salts thereof, have 5-HT$_6$ receptor antagonistic activity. They are useful in treating disorders involving 5-HT$_6$ receptors, or treatable by manipulation of those receptors. For instance in: Parkinson's disease, Huntington's chorea, schizophrenia, anxiety, depression, manic depression, psychoses, epilepsy, obsessive compulsive disorders, mood disorders, migraine, Alzheimer's disease, age related cognitive decline, mild cognitive impairment, sleep disorders, eating disorders, anorexia, bulimia, binge eating disorders, panic attacks, akathisia, attention deficit hyperactivity disorder, attention deficit disorder, withdrawal from abuse of cocaine, ethanol, nicotine or benzodiazepines, pain, disorders associated with spinal trauma or head injury, hydrocephalus, functional bowel disorder, Irritable Bowel Syndrome, obesity and type-2 diabetes.

Other embodiments of the invention include:

pharmaceutical compositions for treating, for example, a disorder or condition treatable by blocking $5\text{-HT}_6$ receptors, the composition comprising a compound of formula (1) or a pharmaceutically acceptable salt thereof, and a pharmaceutically acceptable carrier;

methods of treating a disorder or condition treatable by blocking $5\text{-HT}_6$ receptors, the method comprising administering to a patient in need of such treating a compound of formula (1) or a pharmaceutically acceptable salt thereof;

pharmaceutical compositions for treating, for example, a disorder or condition chosen from the disorders listed herein;

methods of treating a disorder or condition chosen from the disorders listed herein, the methods comprising administering to a patient in need of such treating a compound of formula (1) or a pharmaceutically acceptable salt thereof;

pharmaceutical compositions for treating a disorder or condition chosen from the disorders listed herein, the compositions comprising a compound of formula (1) or a pharmaceutically acceptable salt thereof, and a pharmaceutically acceptable carrier;

methods for treating a disorder or condition chosen from the disorders listed herein, the methods comprising administering to a patient in need of such treating a compound of formula (1) or a pharmaceutically acceptable salt thereof.

methods of antagonizing a $5\text{-HT}_6$ receptor that comprises administering to a subject in need thereof, an effective amount of a compound of formula (1);

The invention also provides the use of a compound or salt according to formula (1) for the manufacture of medicament.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for treating one or more of the conditions listed. Such other therapeutic agent(s) may be administered prior to, simultaneously with, or following the administration of the compounds of the invention.

The invention also provides compounds, pharmaceutical compositions, kits and methods for treating a disorder or condition chosen from the disorders listed herein, the method comprising administering to a patient in need of such treating a compound of formula (1) or a pharmaceutically acceptable salt thereof.

The compounds of the invention possess $5\text{-HT}_6$ receptor antagonizing activity. This activity of the compounds of the invention is readily demonstrated, for example, using one or more of the assays described herein or known in the art.

The invention also provides methods of preparing the compounds of the invention and the intermediates used in those methods.

Isolation and purification of the compounds and intermediates described herein can be affected, if desired, by any suitable separation or purification procedure such as, for example, filtration, extraction, crystallization, column chromatography, thin-layer chromatography, thick-layer chromatography, preparative low or high-pressure liquid chromatography, or a combination of these procedures. Specific illustrations of suitable separation and isolation procedures can be taken from the preparations and examples. However, other equivalent separation or isolation procedures could, of course, also be used.

The compounds of the present invention may contain one or more asymmetric centers and can thus occur as racemates and racemic mixtures, single enantiomers, diastereomeric mixtures and individual diastereomers.

Depending on the nature of the various substituents, the molecule can have additional asymmetric centers. Each such asymmetric center will independently produce two optical isomers. All of the possible optical isomers and diastereomers, in mixtures and as pure or partially purified compounds, belong to this invention. The present invention comprehends all such isomeric forms of these compounds. Formula (1) shows the structure of the class of compounds without preferred stereochemistry. The independent syntheses of these diastereomers, or their chromatographic separations, may be achieved as known in the art by appropriate modification of the methodology disclosed therein. Their absolute stereochemistry may be determined by the X-ray crystallography of crystalline products or crystalline intermediates, which are derivatized, if necessary, with a reagent containing an asymmetric center of known absolute configuration. Racemic mixtures of the compounds can be separated into the individual enantiomers by methods well-known in the art, such as the coupling of a racemic mixture of compounds to an enantiomerically pure compound to form a diastereomeric mixture, followed by separation of the individual diastereomers by standard methods, such as fractional crystallization or chromatography. The coupling often consists of the formation of salts using an enantiomerically pure acid or base, for example (−)-di-p-toluoyl-D-tartaric acid and/or (+)-di-p-toluoyl-L-tartaric acid. The diastereomeric derivatives may then be converted to the pure enantiomers by cleavage of the added chiral residue. The racemic mixture of the compounds can also be separated directly by chromatographic methods utilizing chiral stationary phases: Methods well-known in the art. Alternatively, any enantiomer of a compound may be obtained by stereoselective synthesis using optically pure starting materials or reagents of known configuration by methods well-known in the art.

Cis and trans isomers of the compound of formula (1), or a pharmaceutically acceptable salt thereof, also belong to the invention, and this also applies to tautomers of the compounds of formula (1) or a pharmaceutically acceptable salt thereof.

Some of the crystalline forms for the compounds may exist as polymorphs: as such intended to belong to the invention. In addition, some of the compounds may form solvates with water (i.e. hydrates), or common organic solvents. Such solvates also fall within the scope of this invention.

Isotopically-labeled compound of formula (1) or pharmaceutically acceptable salts thereof, including compounds of formula (1) isotopically-labeled to be detectable by PET or SPECT, also fall within the scope of the invention. The same applies to compounds of formula (I) labeled with [$^{13}$C]-, [$^{14}$C]-, [$^{3}$H]-, [$^{18}$F]-, [$^{125}$I]- or other isotopically enriched atoms, suitable for receptor binding or metabolism studies.

The compounds of the invention may also be used as reagents or standards in the biochemical study of neurological function, dysfunction and disease.

Definitions

Within the context of this description, the term '5-HT$_6$ receptor antagonist' refers to a compound displaying this activity—measured by unambiguous and well accepted pharmacological assays, including those described in WO 2008/034863—without displaying substantial cross-reactivity towards another receptor.

General terms used in the description of compounds herein disclosed bear their usual meanings. The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified as 'lower', the alkyl group will contain from 1 to 6 carbon atoms. The same carbon content applies to the parent term 'alkane', and to derivative terms such as 'alkoxy'. The carbon content of various hydrocarbon containing moieties is indicated by a prefix designating the minimum and maximum number of carbon atoms in the moiety, i.e., the prefix $C_{x-y}$ defines the number of carbon atoms present from the integer "x" to the integer "y" inclusive. 'Alkyl($C_{1-3}$)' for example, means methyl, ethyl, n-propyl or isopropyl, and 'alkyl($C_{1-4}$)' means 'methyl, ethyl, n-propyl, isopropyl, n-butyl, 2-butyl, isobutyl or 2-methyl-n-propyl'. The term 'alkenyl' denotes straight or branched hydrocarbon radicals having one or more carbon-carbon double bonds, such as vinyl, allyl, butenyl, etc., and for example represents ($C_{2-4}$)-alkenyl. In 'alkynyl' groups the straight or branched hydrocarbon radicals have one or more carbon-carbon triple bonds, such as ethynyl, propargyl, 1-butynyl, 2-butynyl, etc., and for example represent ($C_{2-4}$)alkynyl. Unless otherwise stated, álkenyl' and 'alkynyl chains can contain from 1 to 18 carbon atoms.

The term 'acyl' means alkyl($C_{1-3}$) carbonyl, arylcarbonyl or aryl-alkyl($C_{1-3}$)-carbonyl. 'Aryl' embraces mono- or polycyclic aromatic groups, including phenyl, naphthyl, 1,2,3,4-tetrahydro-naphtyl, indenyl, fluorenyl, anthracenyl, phenanthrenyl, naphtacenyl and azulenyl. 'Heteroaryl' embraces mono- or polycyclic hetero-aromatic, including furyl, thienyl, pyrrolyl, oxazolyl, thiazolyl, imidazolyl, imidazo[2,1-b][1,3]thiazolyl, pyrazolyl, isoxazolyl, isothiazolyl, pyridyl, pyridazinyl, pyrimidinyl, pyrazinyl, 1,3,5-triazinyl, indazolyl, indolyl, indolizinyl, isoindolyl, benzo[b]furanyl, 1,2,3,4-tetrahydroiso-quinolinyl, indanyl, indenyl, benzo[b]thienyl, 2,3-dihydro-1,4-benzodioxin-5-yl, benzimidazolyl, cinnolinyl, carbazolyl, acridinyl, phenazinyl, phenothiazinyl, phenoxazinyl, benzothiazolyl, benzo[1,2,5]thia-diazolyl, purinyl, quinolinyl, isoquinolinyl, quinolizinyl, phtalazinyl, quinazolinyl, quinoxalinyl, 1,8-naphthyridinyl and pteridinyl.

'Halo' or 'Halogen' means chloro, fluoro, bromo or iodo; 'hetero' as in 'heteroalkyl, heteroaromatic' etc. means containing one or more N, O or S atoms. 'heteroalkyl' includes alkyl groups with heteroatoms in any position, thus including N-bound O-bound or S-bound alkyl groups.

The term "substituted" means that the specified group or moiety bears one or more substituents. Where any group may carry multiple substituents, and a variety of possible substituents can be provided, the substituents are independently selected, and need not to be the same. The term "unsubstituted" means that the specified group bears no substituents.

With reference to substituents, the term 'independently' means that when more than one of such substituents are possible, they may be the same or different from each other.

'Cycloalkyl($C_{3-8}$)' means cyclopropyl, cyclobutyl, cyclopentyl, cyclohexyl, cycloheptyl or cyclooctyl; 'heterocycloalkyl($C_{4-8}$)' refers to heteroatom containing rings including piperidinyl, morpholinyl, azepanyl, pyrrolidinyl, thiomorpholinyl, piperazinyl, tetrahydrofuryl, tetrahydropyranyl.

The terms "oxy", "thio" and "carbo" as used herein as part of another group respectively refer to an oxygen atom, a sulphur atom and a carbonyl (C=O) group, serving as linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used herein as part of another group respectively refer to an —SO— or an —SO$_2$— group.

To provide a more concise description, the terms 'compound' or 'compounds' include tautomers, stereoisomers, N-oxides, isotopically-labelled analogues, or pharmacologically acceptable salts, also when not explicitly mentioned.

N-oxides of the compounds mentioned above belong to the invention. Tertiary amines may or may not give rise to N-oxide metabolites. The extent to what N-oxidation takes place varies from trace amounts to a near quantitative conversion. N-oxides may be more active than their corresponding tertiary amines, or less active. Whilst N-oxides can easily be reduced to their corresponding tertiary amines by chemical means, in the human body this happens to varying degrees. Some N-oxides undergo nearly quantitative reductive conversion to the corresponding tertiary amines, in other cases conversion is a mere trace reaction, or even completely absent (Bickel, 1969).

The term 'form' encompasses all solids: polymorphs, solvates, and amorphous forms. 'Crystal form' refers to various solid forms of the same compound, for example polymorphs, solvates and amorphous forms. 'Amorphous forms' are non-crystalline materials with no long range order, and generally do not give a distinctive powder X-ray diffraction pattern. Crystal forms in general have been described by Byrn (1995) and Martin (1995). 'Polymorphs' are crystal structures in which a compound can crystallize in different crystal packing arrangements, all of which have the same elemental composition. Polymorphism is a frequently occurring phenomenon, affected by several crystallization conditions such as temperature, level of supersaturation, presence of impurities, polarity of solvent, rate of cooling. Different polymorphs usually have different X-ray diffraction patterns, solid state NMR spectra, infrared or Raman spectra, melting points, density, hardness, crystal shape, optical and electrical properties, stability, and solubility. Recrystallization solvent, rate of crystallization, storage temperature, and other factors may cause one crystal form to dominate.

To give a more concise description, some of the quantitative expressions given herein are not qualified with either "about" or "approximately". It is understood that whether either of these terms is used explicitly or not, every quantity given is meant to refer to the actual value, and also to the approximation to such given value that would reasonably be inferred based on the ordinary skill in the art, including approximations due to experimental or measurement conditions for such given value.

The terms "selective" and "selectivity" refer to compounds that display reactivity towards a particular receptor (e.g. a 5-HT$_6$ receptor) without displaying substantial cross-reactivity towards another receptor (e.g. other 5-HT receptor subtypes).

Throughout the description and the claims of this specification the word "comprise" and variations of the word, such as "comprising" and "comprises" is not intended to exclude other additives, components, integers or steps.

While it may be possible for the compounds of formula (1) to be administered as the raw chemical, it is preferable to present them as a 'pharmaceutical composition'. According to a further aspect, the present invention provides a pharmaceutical composition comprising a compound of formula (1), or a pharmaceutically acceptable salt or solvate thereof, together with one or more pharmaceutically acceptable carriers thereof, and optionally one or more other therapeutic ingredients. The carrier(s) must be 'acceptable' in the sense of being compatible with the other ingredients of the formulation and not deleterious to the recipient thereof.

The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Within the context of this application, the term 'combination preparation' comprises both true combinations, meaning a compound of formula (1) and one or more other medicaments physically combined in one preparation such as a tablet or injection fluid, as well as 'kit-of-parts', comprising a compound of formula (1) and one or more other medicaments in separate dosage forms, together with instructions for use, optionally with further means for facilitating compliance with the administration of the component compounds, e.g. label or drawings. With true combinations, the pharmacotherapy by definition is simultaneous. The contents of 'kit-of-parts', can be administered either simultaneously or at different time intervals. Therapy being either concomitant or sequential will be dependant on the characteristics of the other medicaments used, characteristics like onset and duration of action, plasma levels, clearance, etc., as well as on the disease, its stage, and characteristics of the individual patient.

The affinity of the compounds of the invention for 5-HT$_6$ receptors was determined as described above. From the binding affinity measured for a given compound of formula (1), one can estimate a theoretical lowest effective dose. At a concentration of the compound equal to twice the measured $K_i$-value, nearly 100% of the 5-HT$_6$ receptors likely will be occupied by the compound. Converting that concentration to mg compound per kg patient yields a theoretical lowest effective dose, assuming ideal bioavailability. Pharmacokinetic, pharmacodynamic, and other considerations may alter the dose actually administered to a higher or lower value. The typical daily dose of the active ingredients varies within a wide range and will depend on various factors such as the relevant indication, the route of administration, the age, weight and sex of the patient, and may be determined by a physician. In general, total daily dose administration to a patient in single or individual doses, may be in amounts, for example, from 0.001 to 10 mg/kg body weight daily, and more usually from 0.01 to 1,000 mg per day, of total active ingredients. Such dosages will be administered to a patient in need of treatment from one to three times each day, or as often as needed for efficacy, and for periods of at least two months, more typically for at least six months, or chronically.

The term "therapeutically effective amount" refers to an amount of a therapeutic agent to treat a condition treatable by administrating a composition of the invention. That amount includes the amount sufficient to exhibit a detectable therapeutic or ameliorative response in a human tissue system. The effect may include treating conditions listed herein. The precise pharmaceutically effective amount for a subject will depend upon the subject's size and health, the nature and extent of the condition being treated, recommendations of the physician, and the therapeutics, or combination of therapeutics, selected for administration. Thus, it is not useful to specify an exact pharmaceutically effective amount in advance. The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids (Berge, 1977). The 'free base' form may be regenerated by contacting the salt with a base or acid, and isolating the parent compound in the conventional matter. The parent form of the compound differs from the various salt forms in certain physical properties, such as solubility in polar solvents, but otherwise the salts are equivalent to the parent form of the compound for the purposes of the present invention.

The term "treatment" refers to any treatment of a human condition or disease, and includes: (1) inhibiting the disease or condition, i.e., arresting its development, (2) relieving the disease or condition, i.e., causing the condition to regress, or (3) stopping the symptoms of the disease. The term 'inhibit' includes its generally accepted meaning which includes restraining, alleviating, ameliorating, and slowing, stopping or reversing progression, severity, or a resultant symptom. As used herein, the term "medical therapy" intendeds to include diagnostic and therapeutic regimens carried out in vivo or ex vivo on humans.

As used herein, the term "body weight disorders" refers to the disorders caused by an imbalance between energy intake and energy expenditure, resulting in abnormal (e.g., excessive) body weight. Such body weight-disorders include obesity (Roth, 1994; Sibley, 1993; Sleigh, 1995, 1997). 'Obesity' refers to a condition whereby a person has a Body Mass Index (BMI), calculated as weight per height squared (km/m$^2$), of at least 25.9. Conventionally, those persons with normal weight have a BMI of 19.9 to less than 25.9. The obesity herein may be due to any cause, whether genetic of environmental. Examples of disorders that may result in obesity or be the cause of obesity include overeating and bulimia, polycystic ovarian disease, craniopharyngioma, the Prader-Willi syndrome, Frohlich's syndrome, Type-II diabetes, GH-deficient subjects, normal variant short stature, Turners syndrome, and other pathological conditions showing reduced metabolic activity or a decrease in resting energy expenditure as a percentage of total fat-free mass, e.g. children with acute lymphoblastic leukemia.

| ABBREVIATIONS | |
|---|---|
| ACE-Cl | 1-chloroethyl chloroformate |
| ACN | acetonitrile |
| ADD | attention deficit disorder |
| ADHD | attention deficit hyperactivity disorder |
| API | atmospheric pressure ionisation |
| BEMP | 2-tert-butylimino-2-diethylamino-1,3-dimethyl-perhydro-1,3,2-diazaphosphorine |
| BMI | body mass index |
| Boc | tert-butoxycarbonyl |
| Boc$_2$O | di-tert-butyl dicarbonate |
| CHO | Chinese Hamster Ovary (cells) |
| CNS | central nervous system |
| CUR | curtain gas |
| DCM | dichloromethane |
| DiPEA | N,N-diisopropylethylamine |
| DMAP | 4-dimethylaminopyridin |
| DMC | 2-chloro-1,3-dimethylimidazolinium chloride |
| DMF | N,N'-dimethylformamide |
| DMSO | dimethylsulfoxide |
| EA | ethylacetate |
| SI | Electron Spray Ionization |
| FCS | fetal calf serum |
| FP | focusing potential |
| g | gram(s) |
| h | hour(s) |
| HPLC | High Pressure (Performance) Liquid Chromatography |
| 5-HT | 5-hydroxytryptamine, serotonine |
| MeI | methyl iodide |
| MeOH | methanol |
| mg | milligram(s) |
| min | minute(s) |
| ml or mL | milliliter(s) |
| m.p. | melting point c.q. melting range |
| MS | Mass Spectrometry |
| MTBE | methyl tert-butylether |
| PA | petroleum aether (40-60) |
| R$_f$ | retention factor (thin layer chromatography) |
| R$_t$ | retention time (LC/MS) |
| RT | room temperature |
| SIM | Single Ion Monitoring |
| SCX | Strong Cation eXchange |
| SPE | Solid Phase Extraction |
| t$_{1/2}$ | half-life |
| TBAF | tetrabutylammonium fluoride |
| TBDPS | tert-butyldiphenylsilyl |
| TFAA | trifluoroacetic anhydride |
| TMS | trimethylsilyl |
| TMSCl | trimethylsiliyl chloride |
| THF | tetrahydrofuran |
| WME | Williams Medium E |
| X-Phos | 2-dicyclohexylphosphino-2',4',6'-triisopropylbiphenyl |

EXAMPLE 1

Analytical Methods

Nuclear magnetic resonance spectra ($^1$H NMR) were determined in the indicated solvent using a Bruker ARX 400 ($^1$H: 400 MHz) or a Varian VXR200 ($^1$H: 200 MHz) instrument at 300 K, unless indicated otherwise. The spectra were determined in deuterated chloroform or DMSO obtained from Cambridge Isotope Laboratories Ltd. Chemical shifts (δ) are given in ppm downfield from tetramethylsilane (1H). Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 'ddd' (double double doublet), 's' (singlet), 'bs' (broad singlet) and 'm' (multiplet). NH and OH signals were identified after mixing the sample with a drop of D$_2$O.

Flash chromatography refers to purification using the indicated eluent and silica gel (Merck silica gel 60: 0.040-0.063 mm). Melting points were recorded on a Büchi B-545 melting point apparatus. All reactions involving compounds sensitive to moisture and/or oxygen were carried out under an anhydrous nitrogen atmosphere. Reactions were monitored by using thin-layer chromatography (TLC) on silica coated glass plates (Merck precoated silica gel 60 F254) with the indicated eluent. Spots were visualised by UV light (254 nm) or I$_2$.

Liquid Chromatography-Mass Spectrometry (LC-MS): The LC-MS system consisted of 2 Perkin Elmer series 200 micro pumps. The pumps were connected to each other by a 50 μl tee mixer, connected to a Gilson 215 auto sampler. The method was as follows:

| step | total time | flow (μl/min) | A(%) | B(%) |
|---|---|---|---|---|
| 0 | 0 | 2000 | 95 | 5 |
| 1 | 1.8 | 2000 | 0 | 100 |
| 2 | 2.5 | 2000 | 0 | 100 |
| 3 | 2.7 | 2000 | 95 | 5 |
| 4 | 3.0 | 2000 | 95 | 5 |

A = 100% Water with 0.025% HCOOH and 10 mmol NH$_4$HCOO pH = ±3

B = 100% ACN with 0.025% HCOOH

The auto sampler had a 2 μl injection loop, and was connected to a Waters Atlantis C18 30*4.6 mm column with 3 μm particles. The column was thermostated in a Perkin Elmer series 200 column oven at 40° C. The column was connected to a Perkin Elmer series 200 UV meter with a 2.7 μl flowcel. The wavelength was set to 254 nm. The UV meter was connected to a Sciex API 150EX mass spectrometer. The mass spectrometer had the following parameters:

Scanrange:150-900 a.m.u.; polarity: positive; scan mode: profile; resolution Q1: UNIT; step size: 0.10 a.m.u.; time per scan: 0.500 sec; NEB: 10; CUR: 10 IS: 5200; TEM: 325; DF: 30; FP: 225 and EP: 10. The light scattering detector was connected to the Sciex API 150. The light scattering detector was a Sedere Sedex 55 operating at 50° C. and 3 bar N$_2$. The complete system was controlled by a G3 powermac.

EXAMPLE 2

General Aspects of Syntheses

Suitable syntheses of claimed compounds and intermediates containing pyrazoline moieties follow routes analogous to those previously disclosed in WO 2008/034863, employing 4,5-dihydro-1H-pyrazole or 4,5-dihydro-3H-pyrazole building blocks which are either commercially available or prepared as described below.

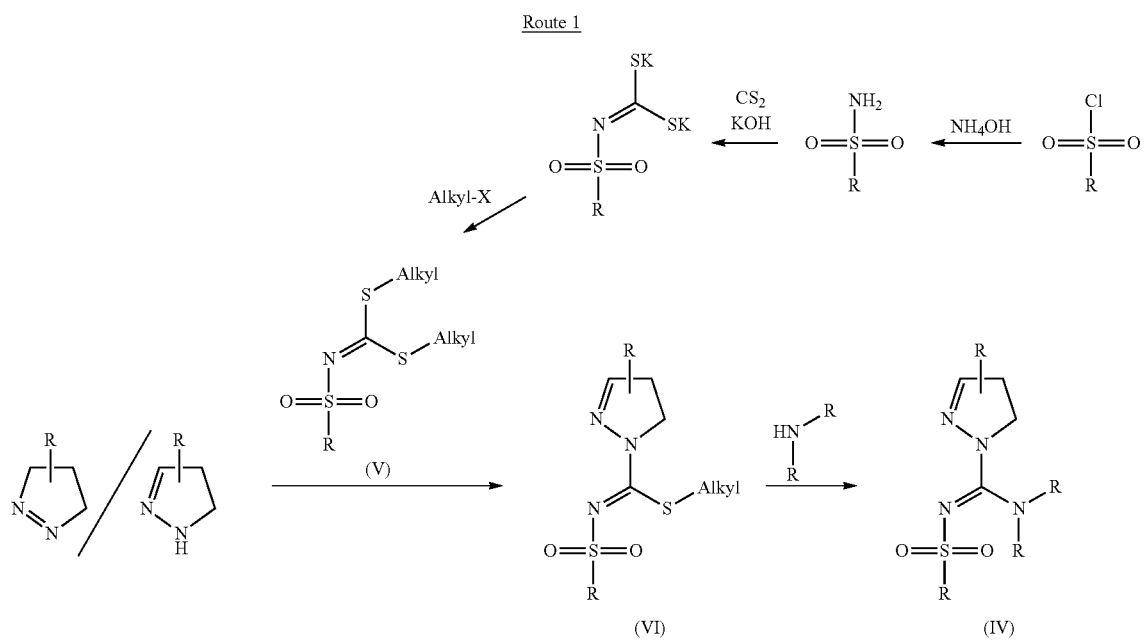

Route 1 employs N-(bis-alkylsulfanyl-methylene)-sulfonamide structures of general formula (V), which may be prepared from sulfonamides by reaction with CS₂ in the presence of KOH, followed by reaction with an alkyl halide such as methyl iodide. The two S-alkyl functionalities can subsequently be substituted by amines, preferably starting with the pyrazoline building blocks to obtain structures of general formula (VI), to end with sulfonylpyrazoline carboxamidine derivatives of general formula (IV).

Route 2 employs alkyl-isothiourea fragments or suitable salt forms thereof of general formula (IX), conveniently prepared by reaction of thiourea building blocks with alkyl halides, such as methyl iodide, that can be reacted with pyrazolines in the presence of base to obtain pyrazoline carboxamidine derivatives of general formula (X). The latter can be reacted with sulfonyl halides (X=Br, Cl, F, preferably Cl) in the presence of base to obtain sulfonylpyrazoline carboxamidine derivatives of general formula (IV).

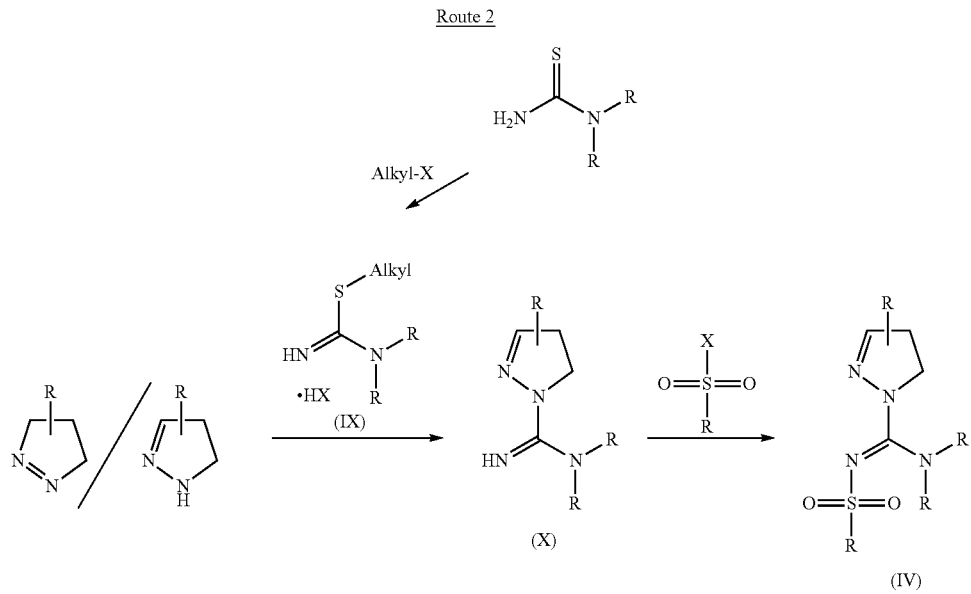

Route 3

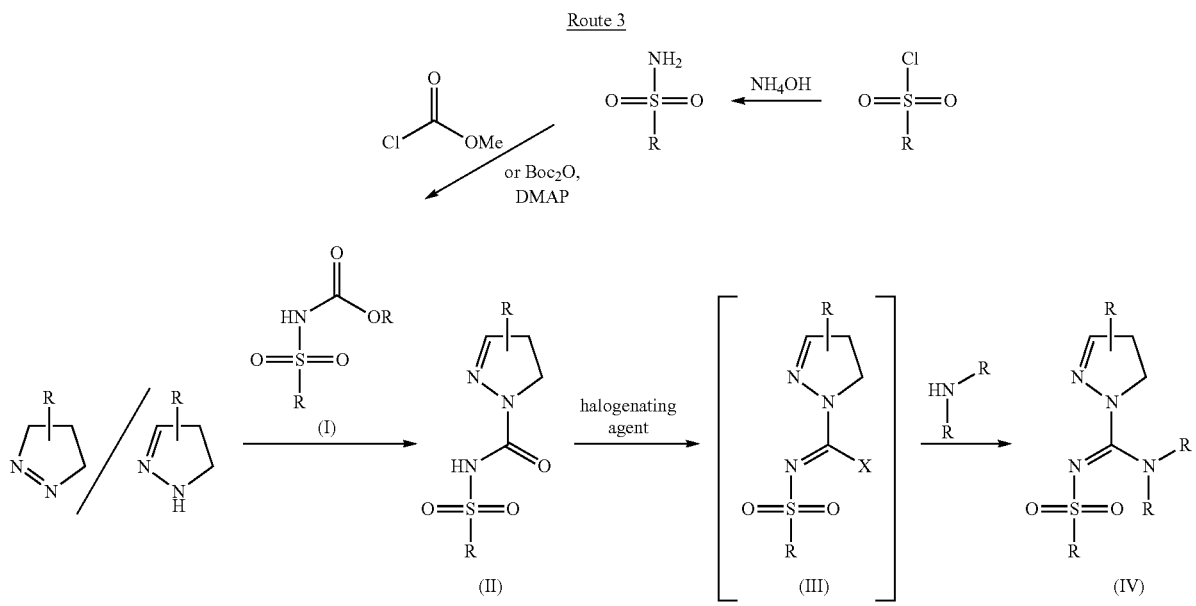

Route 3 employs sulfonyl carbamates of general formula (I), which can for instance be prepared by reaction of sulfonamides with methyl chloroformate or di-tert-butyl dicarbonate in the presence of base. Their reaction products with pyrazolines of general formula (II) can subsequently be converted into the chloroimine intermediates of general formula (III) using halogenating agents such as $PCl_3$, $POCl_3$/DMAP or 2-chloro-1,3-dimethylimidazolinium chloride (DMC), followed by reaction with amines to obtain sulfonylpyrazoline carboxamidine derivatives of general formula (IV).

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid or an organic acid.

EXAMPLE 3

Syntheses of Pyrazoline Intermediates

The following pyrazoline intermediates were synthesized as described in WO 2008/034863.

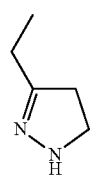

(i)

-continued

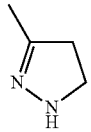

(ii)

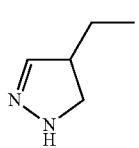

(iii)

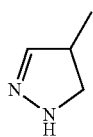

(iv)

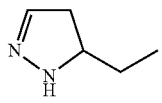

(v)

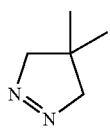

(vi)

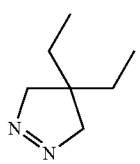

(vii)

-continued
(viii)
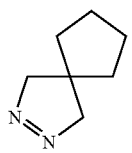
(ix)
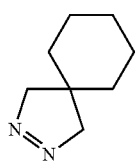
(x)
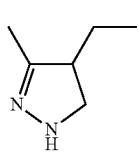
(xi)
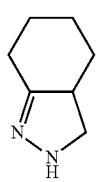
(xii)
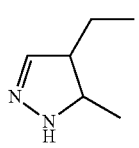
(xiii)
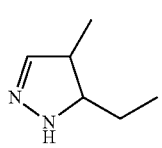
(xiv)
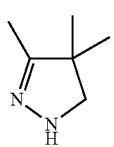
(xv)
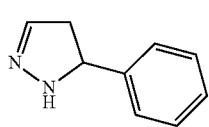
(xvi)
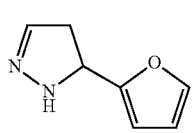
-continued
(xvii)
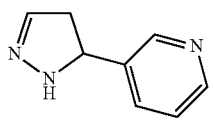
(xviii)
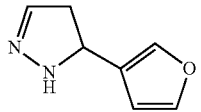
(xix)
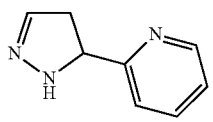
(xx)
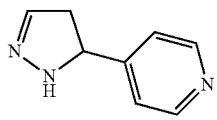
(xxi)
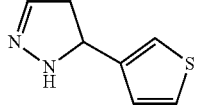
(xxii)
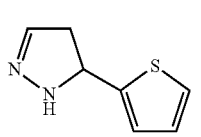
(xxiii)
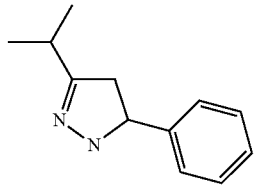
(xxiv)
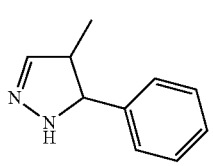
(xxv)
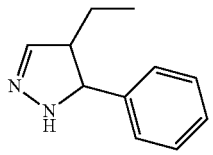
(xxvi)
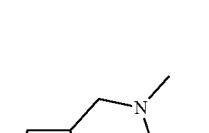

-continued

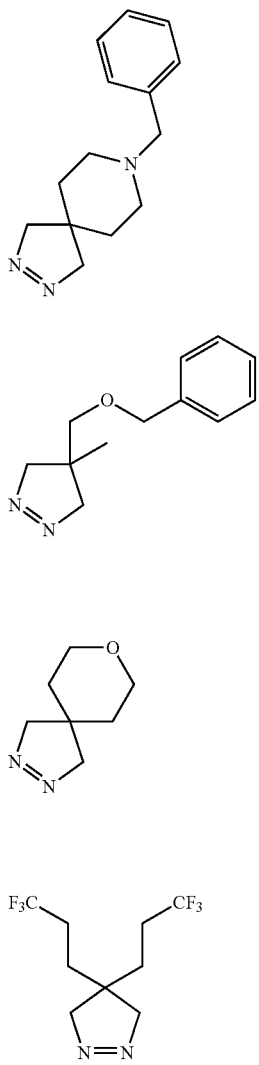

(i) 3-Ethyl-4,5-dihydro-1H-pyrazole
(ii) 3-Methyl-4,5-dihydro-1H-pyrazole
(iii) 4-Ethyl-4,5-dihydro-1H-pyrazole
(iv) 4-Methyl-4,5-dihydro-1H-pyrazole
(v) 5-Ethyl-4,5-dihydro-1H-pyrazole
(vi) 4,4-Dimethyl-4,5-dihydro-3H-pyrazole
(vii) 4,4-Diethyl-4,5-dihydro-3H-pyrazole
(viii) 2,3-Diaza-spiro[4.4]non-2-ene
(ix) 2,3-Diaza-spiro[4.5]dec-2-ene
(x) 4-Ethyl-3-methyl-4,5-dihydro-1H-pyrazole
(xi) 3,3a,4,5,6,7-Hexahydro-2H-indazole
(xii) 4-Ethyl-5-methyl-4,5-dihydro-1H-pyrazole
(xiii) 5-Ethyl-4-methyl-4,5-dihydro-1H-pyrazole
(xiv) 3,4,4-Trimethyl-4,5-dihydro-1H-pyrazole
(xv) 5-Phenyl-4,5-dihydro-1H-pyrazole
(xvi) 5-Furan-2-yl-4,5-dihydro-1H-pyrazole
(xvii) 3-(3,4-Dihydro-2H-pyrazol-3-yl)-pyridine
(xviii) 5-Furan-3-yl-4,5-dihydro-1H-pyrazole
(xix) 2-(3,4-Dihydro-2H-pyrazol-3-yl)-pyridine
(xx) 4-(3,4-Dihydro-2H-pyrazol-3-yl)-pyridine
(xxi) 5-Thiophen-3-yl-4,5-dihydro-1H-pyrazole
(xxii) 5-Thiophen-2-yl-4,5-dihydro-1H-pyrazole
(xxiii) 3-Isopropyl-5-phenyl-4,5-dihydro-1H-pyrazole
(xxiv) 4-Methyl-5-phenyl-4,5-dihydro-1H-pyrazole
(xxv) 4-Ethyl-5-phenyl-4,5-dihydro-1H-pyrazole
(xxvi) 5-Methyl-3a,4,5,6,7,7a-hexahydro-1H-pyrazolo[4,3-c]pyridine
(xxvii) 8-Benzyl-2,3,8-triaza-spiro[4.5]dec-2-ene
(xxviii) 4-Benzyloxymethyl-4-methyl-4,5-dihydro-3H-pyrazole
(xxix) 8-Oxa-2,3-diaza-spiro[4.5]dec-2-ene
(xxx) 4,4-Bis-(2,2,2-trifluoro-ethyl)-4,5-dihydro-3H-pyrazole

EXAMPLE 4

Syntheses of Specific Compounds

4-Amino-N-[(2,3-diaza-spiro[4.4]non-3-en-2-yl)-ethylamino-methylene]benzenesulfonamide (Compound 4)

4-Amino-N-(bis-methylsulfanyl-methylene)-benzenesulfonamide

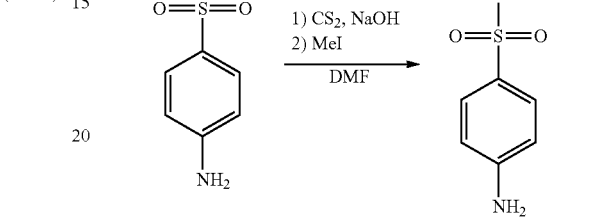

100 g Sulfanilamide was dissolved in 375 mL DMF, 33.2 mL of a 50% aqueous solution of NaOH was added dropwise and stirring was continued for 10 min. at room temperature. To the white suspension, 19.2 mL carbon disulfide was added dropwise and the mixture was stirred for 30 min. at room temperature. The mixture was treated twice more with subsequent addition of 18.1 mL 50% aqueous NaOH and 9.6 mL carbon disulfide, with a 10 min. stirring interval in between the two cycles. After finally stirring the mixture for 30 min, the orange/red solution was cooled with an ice bath, and 72.3 mL iodomethane was added dropwise at such a rate that the temperature of the mixture was kept below 25° C. An amount of 25 mL DMF was added to keep the mixture stirrable, and stirring was continued for 1 h. While still cooling, 250 mL of water was added to the mixture and the suspension was stirred mechanically overnight at room temperature. The precipitate was filtered off and washed with water and cold ethanol. The residue was recrystallized from ethyl acetate to give, after drying at 50° C. in vacuo, 64.9 g (40%) of a white solid. $^1$H NMR (400 MHz, DMSO-$d_6$) δ 3.38 (s, 6H), 6.15 (s, 2H), 6.66 (d, J=8.73 Hz, 2H), 7.56 (d, J=8.73 Hz, 2H).

4-Amino-N-[(2,3-diaza-spiro[4.4]non-3-en-2-yl)-methylsulfanyl-methylene]-benzenesulfonamide

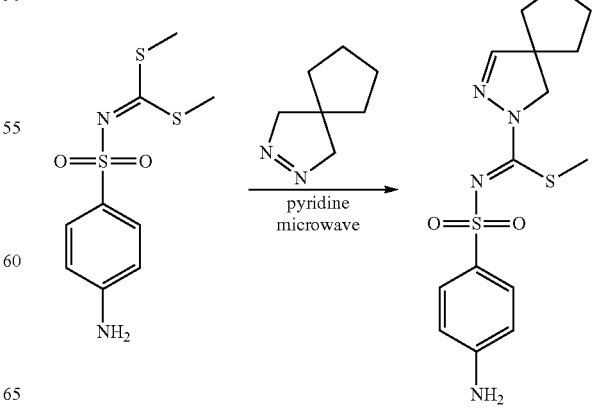

In a 25 mL microwave vial, 2.00 g 4-amino-N-(bis-methylsulfanyl-methylene)benzenesulfonamide and 1.00 g 2,3-diaza-spiro[4.4]non-2-ene were dissolved in 15 mL pyridine. The vial was capped and heated for 2 h. at 180° C. in the microwave. The mixtures resulting from 8 of these sequential experiments were combined and concentrated under reduced pressure. The residue was subjected to flash chromatography (DCM/EA 95:5→90:10) and evaporation of the pure fractions gave 5.20 g (25%) of a yellow solid. $^1$H NMR (400 MHz, CDCl$_3$) δ 1.63-1.92 (m, 8H), 2.23 (s, 3H), 3.06 (s, 2H), 4.03 (s, 2H), 6.67 (d, 2H), 6.98 (s, 1H), 7.74 (d, 2H).

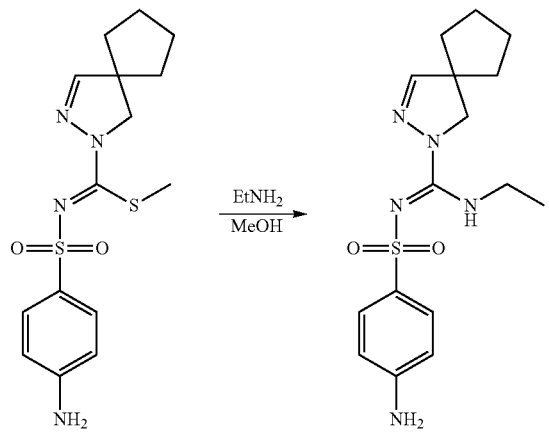 [SMILES: "EtNH2" ; "MeOH" ; CS/C(=N\S(=O)(=O)c1ccc(N)cc1)N1CC2(C=N1)CCCC2 ; CCN/C(=N\S(=O)(=O)c1ccc(N)cc1)N1CC2(C=N1)CCCC2]

To a solution of 4.05 g 4-amino-N-[(2,3-diaza-spiro[4.4]non-3-en-2-yl)-methylsulfanyl-methylene]-benzenesulfonamide in 30 mL MeOH was added 7.86 mL of a 70% aqueous solution of ethylamine. The mixture was stirred for 1 h. at room temperature and evaporated to dryness. The residue was dissolved in a minimal amount of DCM and triturated with MTBE. The precipitate was filtered off and dried in vacuo, and subsequently recrystallized from n-butyl acetate to give 2.40 g (67%) of 4-amino-N-[(2,3-diaza-spiro[4.4]non-3-en-2-yl)-ethylamino-methylene]-benzenesulfonamide as an off-white microcrystalline material after drying in vacuo at 80° C.; m.p. 141-142° C. $^1$H NMR (400 MHz, CDCl$_3$) δ 1.14 (t, J=7.22 Hz, 3H), 1.47-1.89 (m, 8H), 3.35-3.57 (m, 2H), 3.79 (s, 2H), 4.02 (br.s., 2H), 6.65 (d, J=8.73 Hz, 2H), 6.78 (s, 1H), 6.91 (br. s., 1H), 7.70 (d, J=8.73 Hz, 2H).

4-Amino-N-[(2,3-diaza-spiro[4.4]non-3-en-2-yl)-ethylamino-methylene]-3-fluoro-benzenesulfonamide (Compound 15)

3-Fluoro-4-nitro-benzenesulfonamide

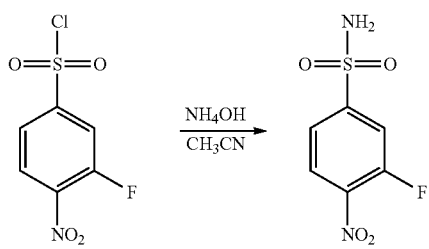 [SMILES: O=[N+]([O-])c1ccc(S(=O)(=O)Cl)cc1F ; "CH3CN" ; "NH4OH" ; NS(=O)(=O)c1ccc([N+](=O)[O-])c(F)c1]

To a solution of 5.00 g 3-fluoro-4-nitrobenzenesulfonyl chloride in 20 mL acetonitrile cooled in an ice bath was added dropwise 4.40 mL of a 30% ammonium hydroxide solution. After removal of the ice bath, stirring was continued for 30 min. at room temperature. Water was added and the mixture was extracted with DCM. The combined organic layers were dried over MgSO$_4$ and evaporated to dryness to give 4.65 g (99%) of a yellow solid. $^1$H NMR (400 MHz, DMSO-d$_6$) δ 7.51 (s, 2H), 7.89 (d, J=9.33 Hz, 1H), 7.92 (dd, J=10.23, 1.81 Hz, 1H), 8.14-8.21 (m, 1 H).

4-Amino-3-fluoro-benzenesulfonamide

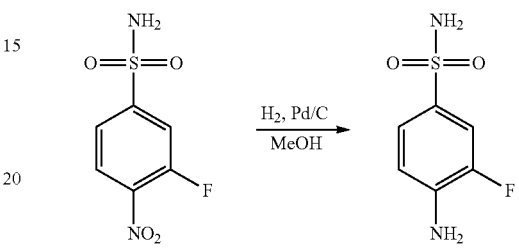

To a solution of 1.00 g 3-fluoro-4-nitro-benzenesulfonamide in 10 mL MeOH was added 10 mol % of palladium on carbon. The mixture was hydrogenated for 30 minutes at a H$_2$ pressure of 50 psi. After filtration over Hyflo, concentration in vacuo yielded 630 mg (74%) of a dark-brown oil. $^1$H NMR (400 MHz, DMSO-d$_6$) δ 6.83 (t, J=8.43 Hz, 1H), 7.42 (dd, J=8.28, 1.96 Hz, 1H), 7.47 (dd, J=10.99, 1.96 Hz, 1H) [NH$_2$'s invisible].

4-Amino-N-(bis-methylsulfanyl-methylene)-3-fluoro-benzenesulfonamide

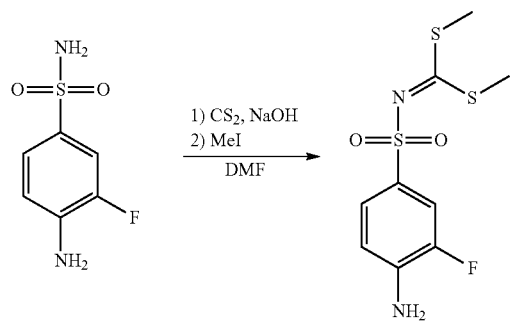

1.15 g 4-Amino-3-fluoro-benzenesulfonamide was dissolved in 50 mL DMF, 0.33 mL of a 50% aqueous solution of NaOH was added dropwise and stirring was continued for 30 min. at room temperature. To the mixture, 0.16 mL carbon disulfide was added dropwise and the mixture was stirred for 1 h. at room temperature. The mixture was treated twice more with subsequent addition of 0.16 mL 50% aqueous NaOH and 0.08 mL carbon disulfide, with a 30 min. stirring interval in between the two cycles. After finally stirring the mixture for 1 h., to the purple solution 0.72 mL iodomethane was added dropwise and stirring was continued for 1 h. After cooling the mixture in an ice bath, 100 mL of water was slowly added to the mixture and the suspension was stirred mechanically overnight at room temperature. The precipitate was filtered off and dried to give 0.60 g (35%) of a brown solid. $^1$H NMR (400 MHz, CDCl$_3$) δ 2.55 (s, 6H), 4.20 (br. s., 2H), 6.80 (t, J=8.58 Hz, 1H), 7.56-7.64 (m, 2 H).

4-Amino-N-[(2,3-diaza-spiro[4.4]non-3-en-2-yl)-methylsulfanyl-methylene]-3-fluoro-benzenesulfonamide

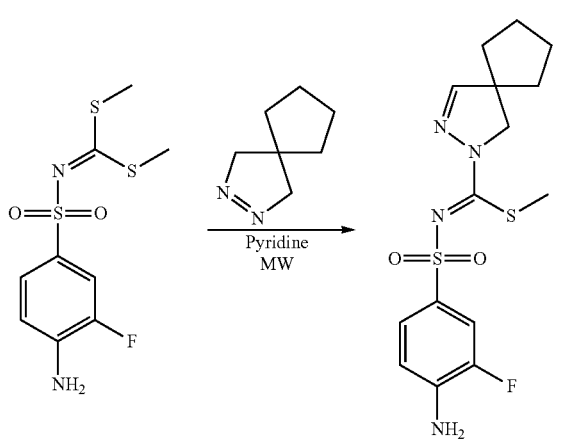

In a 10 mL microwave vial, 530 mg 4-amino-N-(bis-methylsulfanyl-methylene)-3-fluoro-benzenesulfonamide and 325 mg 2,3-diaza-spiro[4.4]non-2-ene were dissolved in 5 mL pyridine, and a drop of ionic liquid (1-butyl-3-methylimidazolium hexafluorophosphate) was added. The vial was capped and heated for 2 h. at 180° C. in the microwave. The mixture was concentrated under reduced pressure and dried in vacuo, and the crude product (840 mg) was used in the subsequent step. $^1$H NMR (400 MHz, CDCl$_3$) δ 1.60-2.03 (m, 8H), 2.24 (s, 3H), 3.07 (s, 2H), 4.90 (br.s., 2H), 7.00 (s, 1H), 7.28-7.33 (m, 1H), 7.65-7.73 (m, 1H), 8.62 (d, J=3.91 Hz, 1H).

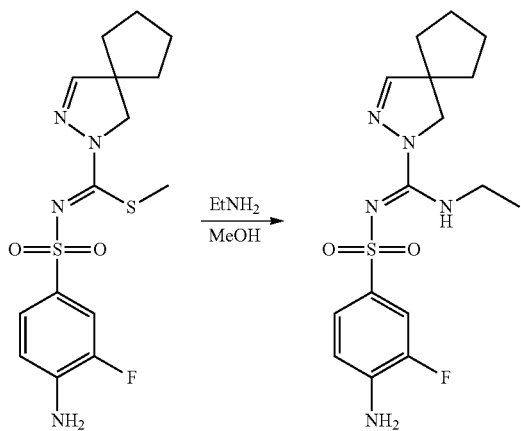 [SMILES: "EtNH2" ; "MeOH" ; CS/C(=N\S(=O)(=O)c1ccc(N)c(F)c1)N1CC2(C=N1)CCCC2 ; CCN/C(=N\S(=O)(=O)c1ccc(N)c(F)c1)N1CC2(C=N1)CCCC2]

To a solution of 840 mg 4-amino-N-[(2,3-diaza-spiro[4.4] non-3-en-2-yl)-methylsulfanyl-methylene]-3-fluoro-benzenesulfonamide (crude) in 25 mL MeOH was added 3.43 mL of a 70% aqueous solution of ethylamine. The mixture was stirred for 1 h. at room temperature, water was added, and the mixture was extracted with DCM. The combined organic layers were dried over MgSO$_4$ and evaporated to dryness. The residue was purified by flash chromatography (EA/PA 3:1) to give 260 mg (33% over 2 steps) of 4-amino-N-[(2,3-diaza-spiro[4.4]non-3-en-2-yl)-ethylamino-methylene]-3-fluoro-benzenesulfonamide as a brown oil. $^1$H NMR (400 MHz, CDCl$_3$) δ 1.16 (t, J=7.2 Hz, 3H), 1.57-1.87 (m, 7H), 3.43-3.53 (m, 2H), 3.82 (s, 2H), 4.02-4.07 (m, 2H), 6.77 (t, J=8.4 Hz, 1H), 6.80 (s, 1H), 7.50-7.58 (m, 2H) [NH$_2$ invisible].

N-[Ethylamino-(5-phenyl-4,5-dihydro-pyrazol-1-yl)-methylene]-4-hydroxybenzenesulfonamide (Compound 25)

N-(Bis-methylsulfanyl-methylene)-4-methoxy-benzenesulfonamide

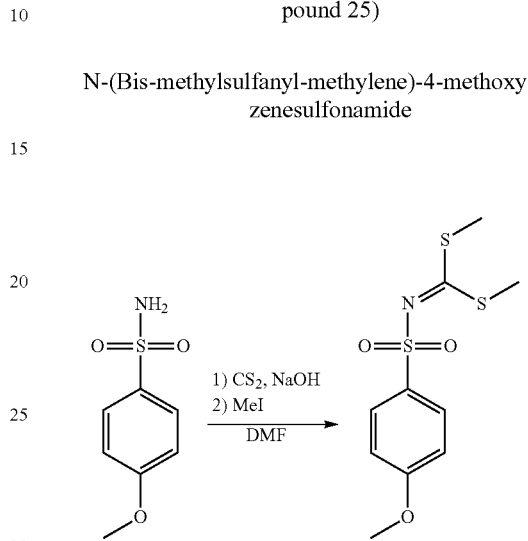

10.00 g 4-Methoxybenzenesulfonamide was dissolved in 90 mL DMF and 5.16 mL carbon disulfide was added. The mixture was cooled in an ice bath, followed by dropwise addition of 6.47 ml of a 50% aqueous solution of NaOH. The dark-red mixture was stirred for 30 min., 7.65 mL of iodomethane was added dropwise, the ice bath was removed and the mixture was stirred for 1 h. at room temperature. Subsequently, 33 mL of water was slowly added to the mixture and the suspension was stirred overnight at room temperature. The precipitate was filtered off, washed 3 times with water and dried in vacuo. The product was purified by flash chromatography (DCM→DCM/MeOH 95:5) to give 8.00 g (44%) of an amorphous oily white material. $^1$H NMR (400 MHz, CDCl$_3$) δ 2.53 (s, 6H), 3.88 (s, 3H), 6.97 (q, J=5.12 Hz, 2H), 7.93 (q, J=5.02 Hz, 2H).

4-Methoxy-N-[methylsulfanyl-(5-phenyl-4,5-dihydro-pyrazol-1-yl)-methylene]benzenesulfonamide

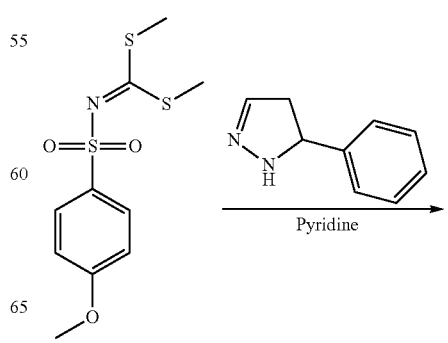

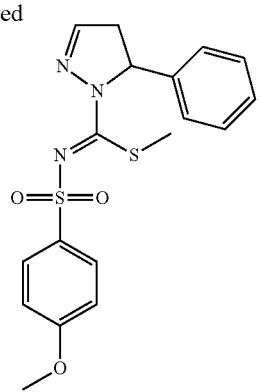

Under N₂ atmosphere, 3.26 g N-(Bis-methylsulfanyl-methylene)-4-methoxy-benzenesulfonamide and 4.34 g 5-phenyl-4,5-dihydro-1H-pyrazole were dissolved in 25 mL pyridine and refluxed during 3 days. The mixture was cooled down and concentrated under reduced pressure. The residue was taken up in EA and extracted with 5% aqueous NaHCO₃ solution. The organic layer was dried over MgSO₄ and evaporated to dryness, and the residue was purified by flash chromatography (DCM→DCM/MeOH 95:5). Evaporation of the pure fractions gave 2.30 g (40%) of a yellow oil. TLC: R_f 0.71 (DCM/MeOH 95:5). LC-MS: R_t 1.85 min (MH+390).

N-[Ethylamino-(5-phenyl-4,5-dihydro-pyrazol-1-yl)-methylene]-4-methoxy-benzenesulfonamide

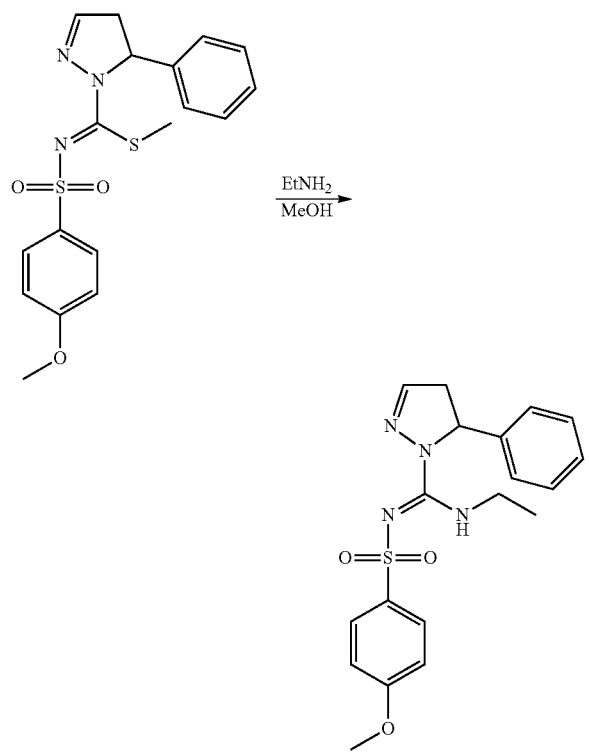

To a solution of 2.30 g 4-Methoxy-N-[methylsulfanyl-(5-phenyl-4,5-dihydro-pyrazol-1-yl)-methylene]-benzenesulfonamide in 50 mL MeOH was added 3.80 mL of a 70% aqueous solution of ethylamine. The mixture was stirred overnight at room temperature and evaporated to dryness. The residue was taken up in EA and extracted with 5% aqueous NaHCO₃ solution. The organic layer was dried over MgSO₄ and evaporated to dryness, and the residue was purified by preparative HPLC to give 1.20 g (62%) of a white amorphous solid. ¹H NMR (400 MHz, CDCl₃) δ 1.14 (t, J=7.2 Hz, 3H), 2.66-2.79 (m, 1H), 3.28-3.42 (m, 1H), 3.48-3.67 (m, 2H), 3.80 (s, 3H), 5.51 (dd, J=11.9, 7.1 Hz, 1H), 6.60 (d, J=9.0 Hz, 2H), 6.94-6.98 (m, 1H), 7.02-7.09 (m, 2H), 7.18 (d, J=9.0 Hz, 2H), 7.20-7.25 (m, 3H) [guanidine NH invisible].

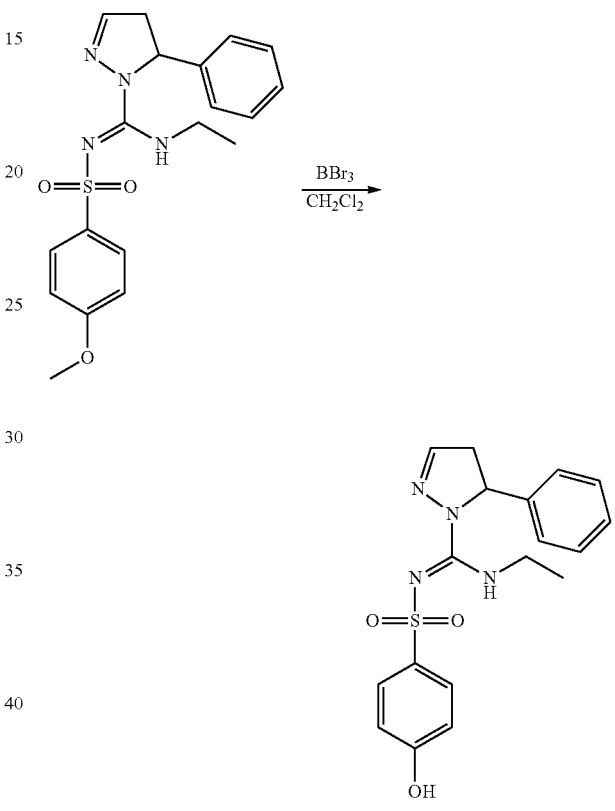

Under N₂ atmosphere, to a solution of 1.05 g N-[ethylamino-(5-phenyl-4,5-dihydro-pyrazol-1-yl)-methylene]-4-methoxy-benzenesulfonamide in 25 mL DCM, 12.91 mL of a 1M solution of boron tribromide in DCM was added. The mixture was stirred overnight at room temperature under N₂ atmosphere, quenched with water, and stirred for another 30 minutes. The solids were filtered off and the filtrate was extracted with water. The organic layer was dried over MgSO₄ and evaporated to dryness. The residue was purified by flash chromatography (stepwise gradient DCM→DCM/MeOH 95:5). The pure fractions were concentrated and triturated with Et₂O. The solids were filtered off and dried in vacuo to give 0.34 g (34%) of N-[ethylamino-(5-phenyl-4,5-dihydro-pyrazol-1-yl)-methylene]-4-hydroxy-benzenesulfonamide as a grey crystalline material, m.p. 158-160° C. ¹H NMR (400 MHz, DMSO-d₆) δ 1.07 (t, J=7.2 Hz, 3H), 2.69-2.81 (m, 1H), 3.36-3.47 (m, 1H), 3.49-3.59 (m, 2H), 5.40-5.51 (m, 1H), 6.55 (d, J=8.7 Hz, 2H), 7.00 (d, J=8.4 Hz, 2H), 7.04-7.12 (m, 3H), 7.22-7.29 (m, 3H), 9.71 (s, 1H) [guanidine NH invisible].

N-[(2,3-Diaza-spiro[4.4]non-3-en-2-yl)-ethylamino-methylene]-4-hydroxymethyl-benzenesulfonamide
(Compound 40)

4-Sulfamoyl-benzoic acid methyl ester

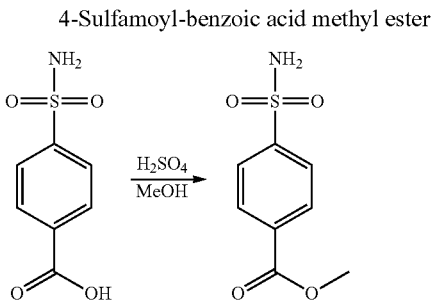

To a mixture of 5.16 g 4-carboxylbenzenesulfonamide in 150 mL methanol was added 6.84 mL sulfuric acid. The mixture was refluxed overnight and cooled to room temperature. The mixture was evaporated to dryness and the residue was triturated with Et$_2$O. The formed precipitation was filtered off, washed with Et$_2$O and dried to give 5.2 gram (92%) of a white solid. $^1$H NMR (400 MHz, CDCl$_3$) δ 3.90 (s, 3H), 7.59 (s, 2H), 7.97 (d, J=5.84 Hz, 2H), 8.15 (d, J=5.84 Hz, 2H).

4-Hydroxymethyl-benzenesulfonamide

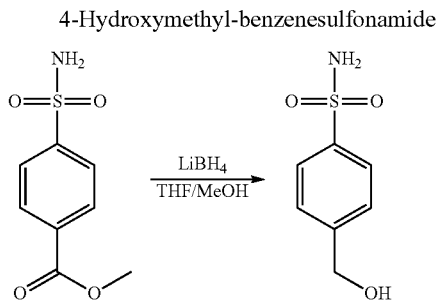

To a solution of 5.2 g 4-sulfamoyl-benzoic acid methyl ester in 100 mL THF and 1.44 mL MeOH, 0.77 g lithium borohydride was added portion-wise over a period of 10 minutes. The mixture was heated at reflux overnight, cooled to room temperature, and poured onto ice containing 100 mL 1N HCl. The mixture was extracted with EtOAc, and the organic layer was dried over MgSO$_4$ and concentrated under reduced pressure. The residue was purified by automated flash chromatography (EtOAc/Hexane 1:1) to give 0.75 gram (17%) of product. $^1$H NMR (400 MHz, DMSO-d$_6$) δ 4.57 (d, J=5.81 Hz, 1H), 5.38 (t, J=5.81 Hz, 1H), 7.48 (d, J=8.34 Hz, 2H), 7.78 (d, J=8.34 Hz, 2H).

4-(tert-Butyl-diphenyl-silanyloxymethyl)-benzenesulfonamide

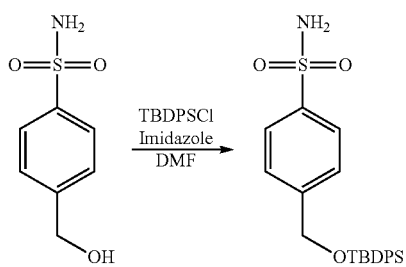

To a mixture of 750 mg 4-hydroxymethyl-benzenesulfonamide in 50 mL DMF were added 1.55 mL tert-butylchlorodiphenylsilane and 539 mg imidazole. The mixture was stirred overnight at room temperature, diluted with EtOAc and extracted with water. The organic phase was dried over MgSO$_4$ and concentrated under reduced pressure. The crude product was purified by automated flash chromatography (DCM) to give 0.5 gram of pure product and 0.6 gram of material from contaminated product fractions. $^1$H NMR (400 MHz, CDCl$_3$) δ 1.07 (s, 3H), 1.11 (s, 6H), 4.75 (s, 2H), 4.82 (s, 2H), 7.35-7.47 (m, 6H), 7.49 (d, J=5.68 Hz, 2H), 7.64-7.74 (m, 4H), 7.90 (d, J=5.68 Hz, 2H).

N-(Bis-methylsulfanyl-methylene)-4-(tert-butyl-diphenyl-silanyloxymethyl)-benzenesulfonamide

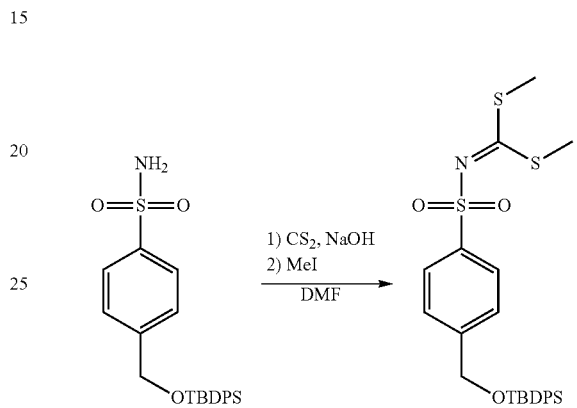

To a mixture of 500 mg 4-(tert-butyl-diphenyl-silanyloxymethyl)-benzenesulfonamide in 50 mL DMF was added 0.11 mL carbon disulfide, and the mixture was cooled to 10° C. Under stirring, 0.14 mL 50% aqueous NaOH was added dropwise and the mixture was stirred for one hour at room temperature. Subsequently, 0.16 mL iodomethane was added dropwise and stirring at room temperature was continued for 30 minutes. After addition of 10 mL of water, the mixture was stirred overnight at room temperature. The precipitation was filtered off, washed with water and dried to give 0.4 gram of product. $^1$H NMR (400 MHz, DMSO-d$_6$) δ 1.04-1.08 (m, 9H), 2.57 (s, 6H), 4.88 (s, 2H), 7.40-7.50 (m, 6H), 7.59 (d, J=8.34 Hz, 2H), 7.63-7.68 (m, 4H), 7.90 (d, J=8.34 Hz, 2H).

4-(tert-Butyl-diphenyl-silanyloxymethyl)-N-[(2,3-diaza-spiro[4.4]non-3-en-2-yl)-methylsulfanyl-methylene]-benzenesulfonamide

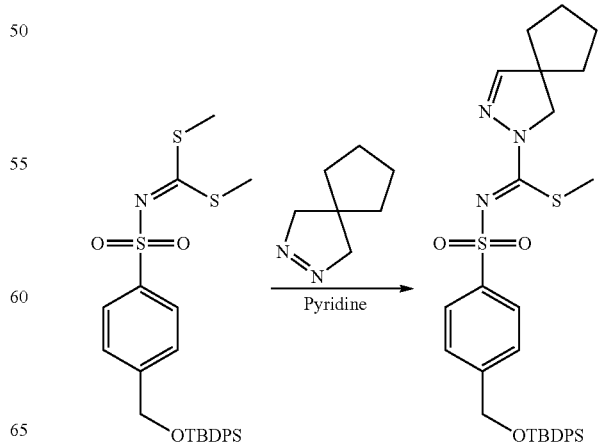

To 15 mL pyridine, 400 mg N-(bis-methylsulfanyl-methylene)-4-(tert-butyl-diphenyl-silanyloxymethyl)-benzenesulfonamide and 111 mg 2,3-diaza-spiro[4.4]non-2-ene were added. The mixture was heated for two nights at 90° C. degrees, concentrated under reduced pressure and dried in vacuo to provide 700 mg of product (LC-MS R$_t$ 3.91 min) which was used in the subsequent step without purification. $^1$H NMR (400 MHz, CDCl$_3$) δ ppm 1.10-1.12 (m, 9H), 1.63-1.94 (m, 8H), 4.82 (s, 2H), 7.01 (s, 1H), 7.65-7.71 (m, 4H), 7.92-7.96 (m, 2H).

4-(tert-Butyl-diphenyl-silanyloxymethyl)-N-[(2,3-diaza-spiro[4.4]non-3-en-2-yl)-ethylamino-methylene]-benzenesulfonamide

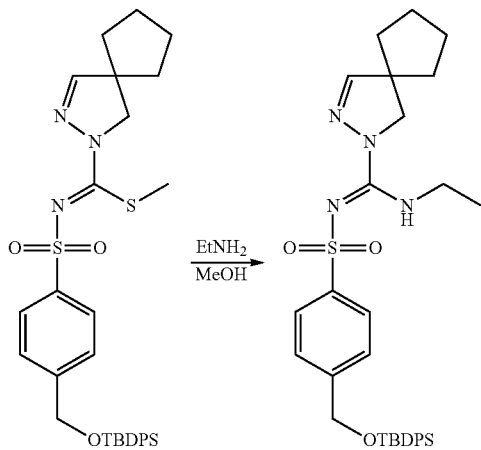

To a solution of 700 mg 4-(tert-butyl-diphenyl-silanyloxymethyl)-N-[(2,3-diaza-spiro[4.4]non-3-en-2-yl)-methylsulfanyl-methylene]-benzenesulfonamide in 50 mL methanol was added 1.84 mL of a 70% aqueous solution of ethylamine. The mixture was stirred for one hour at room temperature and concentrated under reduced pressure. The residue was purified by automated flash chromatography (DCM→DCM/MeOH 97:3) to give 730 mg of product. $^1$H NMR (400 MHz, CDCl$_3$) δ ppm 1.10 (s, 9H), 1.15 (t, J=7.21 Hz, 3H), 1.66-1.75 (m, 8H), 3.48 (dd, J=7.21, 5.38 Hz, 2H), 3.85 (s, 2H), 4.80-4.81 (m, 2H), 6.80 (s, 1H), 7.35-7.47 (m, 6H), 7.65-7.70 (m, 4H), 7.65-7.70 (m, 2H), 7.88-7.91 (m, 2H).

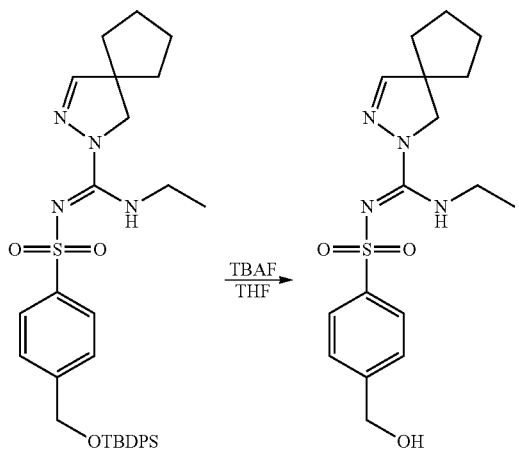

694 mg 4-(tert-Butyl-diphenyl-silanyloxymethyl)-N-[(2,3-diaza-spiro[4.4]non-3-en-2-yl)-ethyl-amino-methylene]-benzenesulfonamide was taken up in 40 mL THF, and 1.04 mL of a 1 M solution of tetrabutylammonium fluoride was added dropwise. The mixture was stirred at room temperature for 4 hours. The mixture was diluted with EtOAc and extracted 3 times with 5% aqueous NaHCO$_3$. The organic phase was dried over MgSO$_4$ and concentrated under reduced pressure. The residue was subjected to automated flash chromatography (DCM/MeOH 95:5), and the resulting crude product was taken up in EtOAc and extracted twice with 2N aqueous NaOH. After drying and concentration, the residue was stirred with 5 mL MTBE, and the resulting white solid was filtered off and dried to give 40 mg product. $^1$H NMR (400 MHz, CDCl$_3$) δ 1.15 (t, J=7.20 Hz, 3H), 1.62-1.86 (m, 8H), 3.41-3.52 (m, 2H), 3.84 (br.s., 1H), 4.77 (d, J=5.31 Hz, 2H), 6.80 (s, 1H), 7.45 (d, J=8.34 Hz, 2H), 7.93 (d, J=8.34 Hz, 2H).

4-Amino-N-[ethylamino-(2,3,8-triaza-spiro[4.5]dec-3-en-2-yl)-methylene]-benzenesulfonamide (Compound 47)

4-Amino-N-[(8-benzyl-2,3,8-triaza-spiro[4.5]dec-3-en-2-yl)-methylsulfanyl-methylene]-benzenesulfonamide

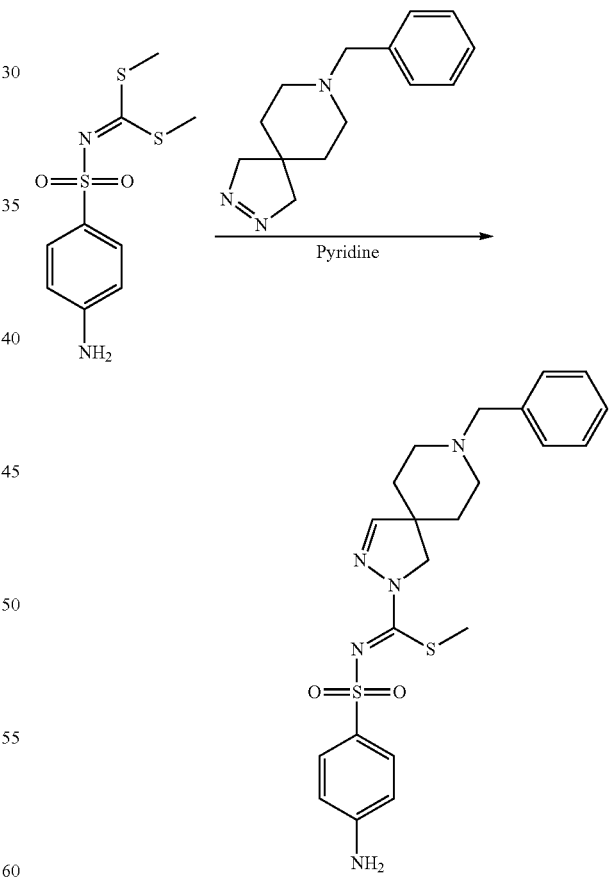

In a 25 mL microwave vial, 1.50 g 4-amino-N-(bis-methylsulfanyl-methylene) benzenesulfonamide and 1.37 g 8-benzyl-2,3,8-triaza-spiro[4.5]dec-2-ene were suspended in 20 mL pyridine. The vial was capped and heated for 1 hour at 180° C. (6 bar) in the microwave. The reaction mixture was concentrated on silica. Purification with flash column chromatography (DCM→DCM/MeOH 99:1→DCM/MeOH 98:2) yielded 1.03 g (41%) of a beige amorph. ¹H NMR (400 MHz, CDCl₃) δ 1.57-1.72 (m, 2H), 1.78-1.92 (m, 2H), 2.17-2.32 (m, 5H), 2.66-2.81 (m, 2H), 3.51 (s, 2H), 4.04 (s, 2H), 4.28 (s, 2H), 6.64-6.71 (m, 2H), 6.98 (s, 1H), 7.20-7.37 (m, 5H), 7.72-7.79 (m, 2H).

4-Amino-N-[(8-benzyl-2,3,8-triaza-spiro[4.5]dec-3-en-2-yl)-ethylamino-methylene]-benzenesulfonamide

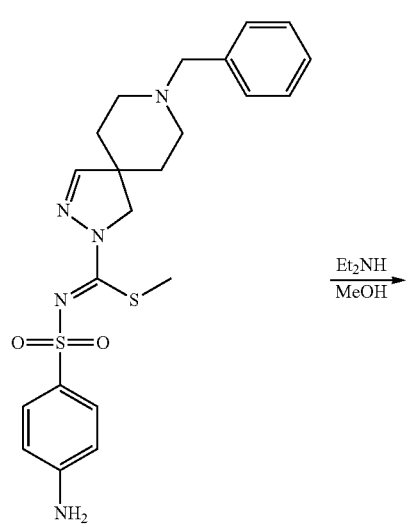

3.41-3.53 (m, 2H), 3.79 (s, 2H), 3.98 (s, 2H), 6.62-6.70 (m, 2H), 6.76 (s, 1H), 6.97 (br s, 1H), 7.22-7.36 (m, 5H), 7.67-7.75 (m, 2H).

(4-{[(8-Benzyl-2,3,8-triaza-spiro[4.5]dec-3-en-2-yl)-ethylamino-methylene]-sulfamoyl}-phenyl)-carbamic acid tert-butyl ester

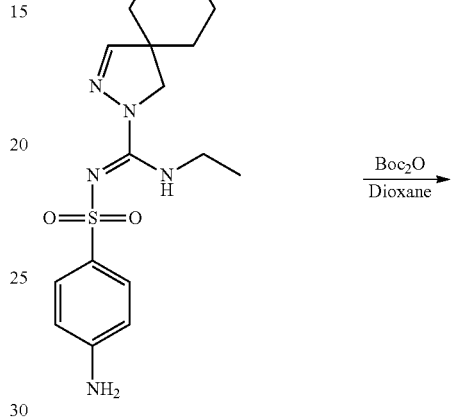

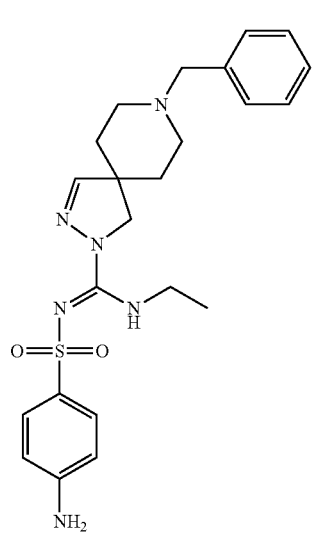

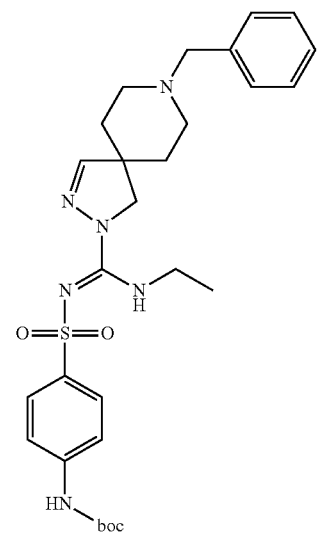

To a solution of 1.35 g 4-amino-N-[(8-benzyl-2,3,8-triaza-spiro[4.5]dec-3-en-2-yl)-methylsulfanyl-methylene]-benzenesulfonamide in 30 mL MeOH was added 2.26 mL (10 equiv.) of a 70% aqueous solution of ethylamine. The mixture was stirred for a weekend at room temperature and concentrated on silica. Purification with flash column chromatography (DCM→DCM/MeOH 99:1→DCM/MeOH 95:5) yielded 1.16 g (87%) of a pale yellow glass. ¹H NMR (400 MHz, CDCl₃) δ 1.14 (t, J=7 Hz, 3H), 1.50-1.60 (m, 2H), 1.73-1.84 (m, 2H), 2.11-2.26 (m, 2H), 2.63-2.76 (m, 2H), To a solution of 510 mg 4-amino-N-[(8-benzyl-2,3,8-triaza-spiro[4.5]dec-3-en-2-yl)-ethylamino-methylene]-benzenesulfonamide in 10 mL 1,4-dioxane was added 490 mg (2 equiv.) di-tert-butyl dicarbonate. The mixture was stirred at reflux overnight, cooled down and concentrated on silica. Purification with flash column chromatography (DCM/MeOH 99:1→95:5) yielded 550 mg (87%) of a yellow glass. ¹H NMR (400 MHz, CDCl₃) δ 1.14 (t, J=7 Hz, 3H), 1.47-1.61 (m, 11H), 1.73-1.86 (m, 2H), 2.11-2.26 (m, 2H), 2.64-2.76 (m, 2H), 3.41-3.54 (m, 2H), 3.80 (s, 2H), 6.66 (s, 1H), 6.78 (s, 1H), 6.94 (br s, 1H), 7.21-7.37 (m, 5H), 7.41-7.48 (m, 2H), 7.82-7.89 (m, 2H).

(4-{[Ethylamino-(2,3,8-triaza-spiro[4.5]dec-3-en-2-yl)-methylene]-sulfamoyl}-phenyl)-carbamic acid tert-butyl ester

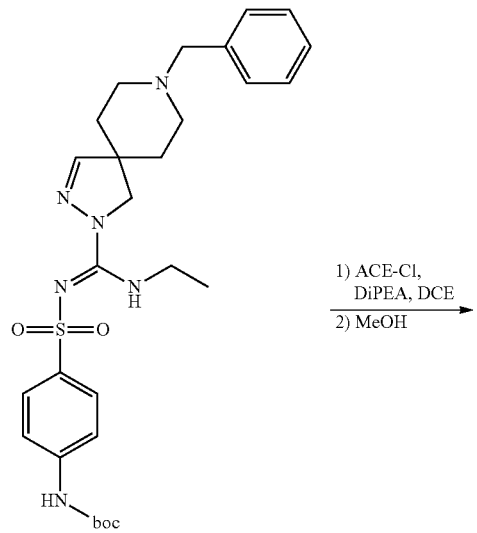

1) ACE-Cl, DiPEA, DCE
2) MeOH

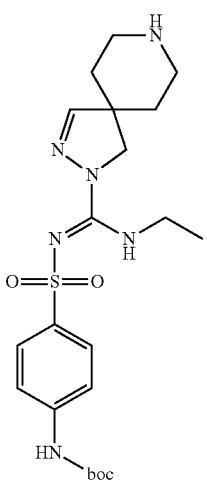

A solution of 550 mg (4-{[(8-Benzyl-2,3,8-triaza-spiro[4.5]dec-3-en-2-yl)-ethylamino-methylene]-sulfamoyl}-phenyl)-carbamic acid tert-butyl ester in 10 mL 1,2-dichloroethane was cooled in an ice bath, and 0.12 mL (1.1 equiv.) 1-chloroethyl chloroformate and 0.03 mL DiPEA were added dropwise. After 15 minutes the ice bath was removed and the mixture was stirred for 30 minutes at room temperature. The mixture was concentrated in vacuo and co-evaporated 3 times with toluene. The residue was taken up in 10 mL MeOH and stirred overnight at room temperature. The mixture was concentrated. The residue was taken up in EA and extracted with 2 M NaOH. The organic layer was dried over $Na_2SO_4$, filtered and concentrated on silica. Purification with flash column chromatography (EtOAc/MeOH/$Et_3N$ 50:45:5) yielded 360 mg (72%) of an orange glass. $^1$H NMR (400 MHz, DMSO-$d_6$) δ 0.96 (t, J=7 Hz, 3H), 1.33-1.43 (m, 2H), 1.48 (s, 9H), 1.53-1.64 (m, 2H), 2.44-2.56 (m, 2H), 2.76-2.88 (m, 2H), 3.21-3.33 (m, 2H), 3.68 (s, 2H), 7.29 (s, 1H), 7.50-7.59 (m, 2H), 7.60-7.74 (m, 3H), 9.70 (s, 1H).

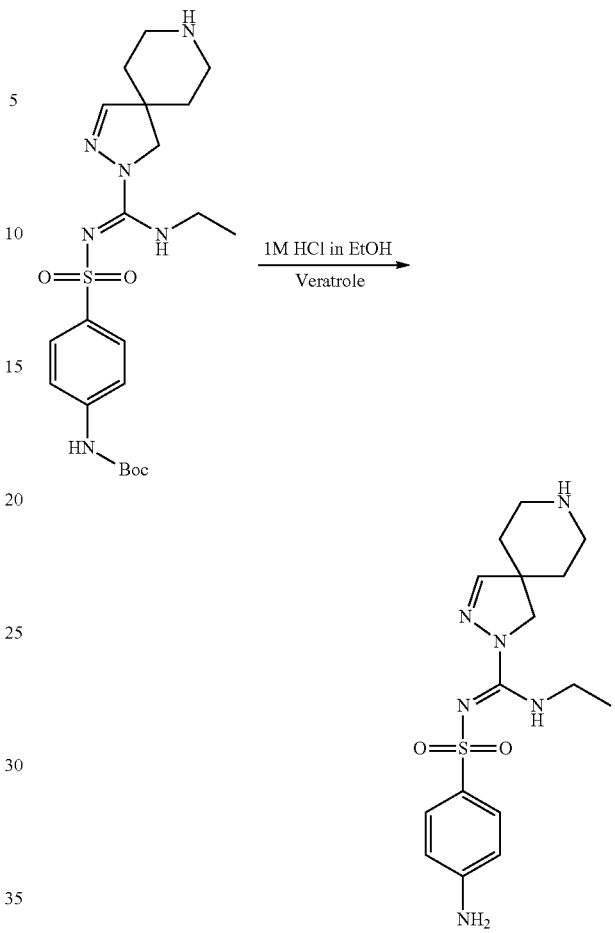

1M HCl in EtOH
Veratrole 360 mg (4-{[ethylamino-(2,3,8-triaza-spiro[4.5]dec-3-en-2-yl)-methylene]-sulfamoyl}-phenyl)-carbamic acid tert-butyl ester was suspended in 10 mL ethanol; 0.44 mL (5 equiv.) of veratrole was added, and subsequently 3.49 mL of 1 M HCl in ethanol (5 equiv.). The mixture was stirred at 60° C. overnight. After cooling down, the mixture was purified with SPE (Isolute Flash SCX-2, conditioning, sampling and washing with MeOH, elution with 1 M $NH_3$ in MeOH) to yield 150 mg (53%) of a yellow glass. $^1$H NMR (400 MHz, DMSO-$d_6$) δ 0.97 (t, J=7 Hz, 3H), 1.33-1.45 (m, 2H), 1.52-1.66 (m, 2H), 2.46-2.60 (m, 2H), 2.76-2.90 (m, 2H), 3.20-3.40 (m, 2H), 3.66 (s, 2H), 5.71 (s, 2H), 6.50-6.61 (m, 2H), 7.26 (s, 1H), 7.37-7.52 (m, 3H).

Compounds Prepared by this Synthetic Route are Marked 'Route 1' in the Table Below.

4-Amino-N-[(4,4-dimethyl-4,5-dihydro-pyrazol-1-yl)-ethylamino-methylene]-benzenesulfonamide (Compound 3)

1-ethyl-2-methyl-isothiourea hydroiodide

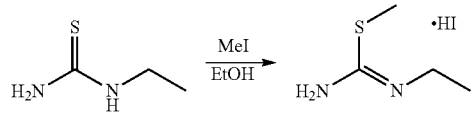

20.5 g Ethyl-thiourea was dissolved in 100 mL EtOH. The mixture was cooled with an ice bath and 13.5 mL (1.1 eq.) MeI was added dropwise. The mixture was stirred for 1 hour at room temperature and concentrated in vacuo to yield 48.3 g of a light-yellow oil. $^1$H NMR (400 MHz, DMSO-$d_6$) δ 1.17 (t, J=7.5 Hz, 3H), 2.61 (s, 3H), 3.34 (q, J=7.5 Hz, 2H), 9.10 (br s, 2H).

N-Ethyl-4,4-dimethyl-4,5-dihydro-pyrazole-1-carboxamidine hydrochloride

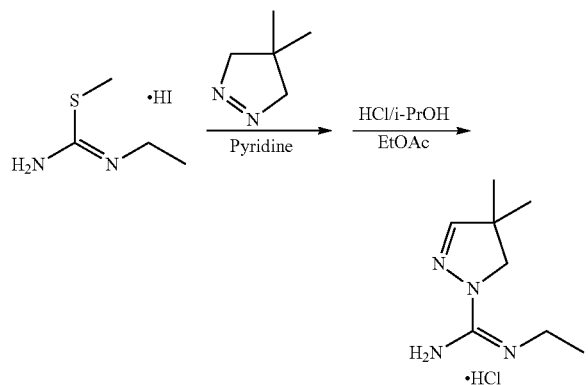

12.0 g 4,4-dimethyl-4,5-dihydro-3H-pyrazole was dissolved in 100 mL pyridine. A solution of 30.0 g 1-Ethyl-2-methyl-isothiourea hydroiodide in 50 mL pyridine was added and the mixture was refluxed for 20 hours. The mixture was cooled to room temperature and concentrated under reduced pressure, and the residue was taken up in DCM (120 mL). The organic phase was extracted with 2N NaOH (2×120 mL), washed with water (120 mL), dried over $Na_2SO_4$ and evaporated under reduced pressure to yield 16.3 g (79%) of an orange oil. The oil (10.0 g) was taken up in EtOAc (50 mL) and heated to 60° C. After removal of the heat source, a 5-6N solution of HCl in isopropanol (20 mL) was dosed over a period of 4 minutes. After cooling to room temperature, EtOAc (50 mL) was added over a period of 4 minutes, and the mixture was stirred at 20° C. for 90 minutes. The formed crystals were collected by filtration and washed with EtOAc (20 mL), followed by drying under reduced pressure at mild heating, to give 6.52 g (54%) of the desired product as a yellow solid. $^1$H NMR (400 MHz, DMSO-$d_6$) δ 1.13 (t, J=7 Hz, 3H), 1.24 (s, 6H), 3.27-3.34 (m, 2H), 3.64 (s, 2H), 7.26 (s, 1H), 8.03 (br s, 2H), 8.13 (br s, 1H).

N-(4-{[(4,4-dimethyl-4,5-dihydro-pyrazol-1-yl)-ethylamino-methylene]-sulfamoyl}-phenyl)acetamide

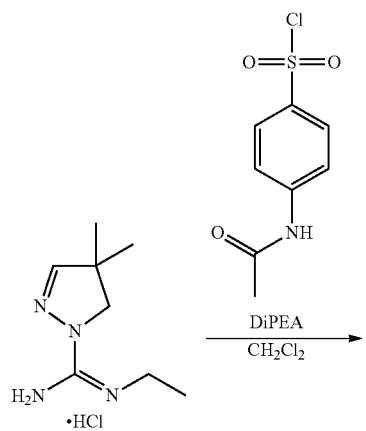

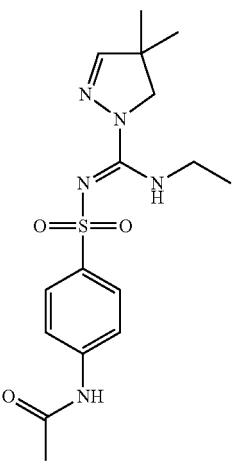

500 mg N-Ethyl-4,4-dimethyl-4,5-dihydro-pyrazole-1-carboxamidine hydrochloride was suspended in 10 mL DCM, 0.88 mL of DiPEA was added, followed by 571 mg 4-acetylamino-benzenesulfonyl chloride. The mixture was stirred overnight at room temperature. Conversion was taken further by reacting overnight after adding another 0.44 mL of base and 290 mg of sulfonyl chloride. The mixture was extracted subsequently with 5% aqueous $NaHCO_3$ and 2M NaOH solution, the organic layer was dried over $Na_2SO_4$, and evaporated to dryness and the crude product (900 mg of a purple oil, containing >95% of anticipated product based on LC-MS) was used in the subsequent step. LC-MS: $R_t$ 1.34 min (MH+ 366).

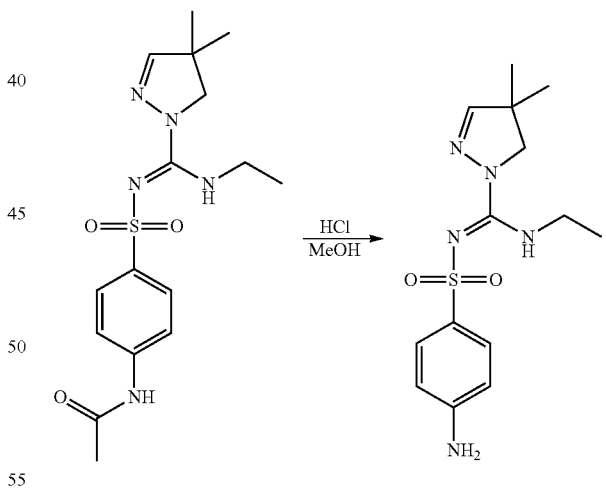

900 mg N-(4-{[(4,4-Dimethyl-4,5-dihydro-pyrazol-1-yl)-ethylamino-methylene]-sulfamoyl}-phenyl) acetamide was dissolved in 5 mL MeOH, and 5 mL of concentrated HCl was added. The mixture was stirred overnight at room temperature. The mixture was basified with 2M NaOH, and extracted twice with DCM. The combined organic layers were dried over $Na_2SO_4$ and evaporated to dryness. The residue was purified by flash chromatography (DCM/MeOH 99:1) to give 400 mg (50%) of 4-Amino-N-[(4,4-dimethyl-4,5-dihydro-pyrazol-1-yl)-ethylamino-methylene]-benzenesulfonamide as an amorphous solid. $^1$H NMR (400 MHz, $CDCl_3$) δ 1.15 (t, J=7 Hz, 3H), 1.20 (s, 6H), 3.42-3.51 (m, 2H), 3.74 (br.s., 2H), 4.00 (br.s., 2H), 6.62-6.68 (m, 2H), 6.71 (s, 1H), 6.90 (br.s., 1H), 7.67-7.73 (m, 2H).

4-Amino-3-chloro-N-[(4,4-dimethyl-4,5-dihydro-pyrazol-1-yl)-ethylamino-methylene]-benzenesulfonamide (Compound 13)

N-(2-Chloro-4-{[(4,4-dimethyl-4,5-dihydro-pyrazol-1-yl)-ethylamino-methylene]-sulfamoyl}-phenyl)-acetamide

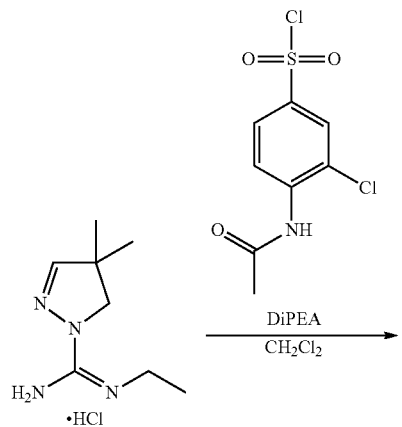

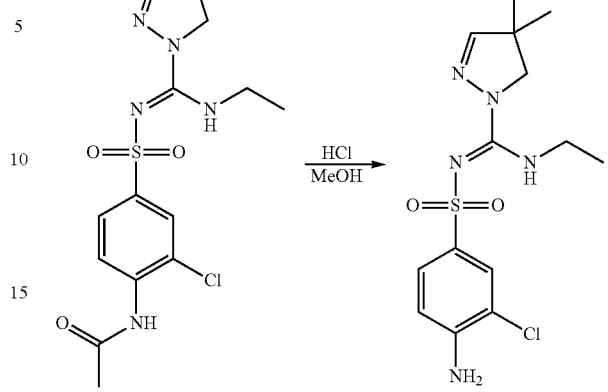

500 mg N-Ethyl-4,4-dimethyl-4,5-dihydro-pyrazole-1-carboxamidine hydrochloride was suspended in 10 mL DCM, 0.88 mL of DiPEA was added, followed by 655 mg 4-acetylamino-3-chloro-benzenesulfonyl chloride. The mixture was stirred overnight at room temperature. Conversion was taken further by reacting overnight after adding another 0.44 mL of base and 290 mg of sulfonyl chloride. The mixture was extracted subsequently with 5% aqueous NaHCO$_3$ and 2M NaOH solution, the organic layer was dried over Na$_2$SO$_4$, and evaporated to dryness and the crude product (680 mg containing 85% of anticipated product based on LC-MS) was used in the subsequent step. LC-MS: R$_t$ 1.46 min (MH+400).

680 mg N-(2-Chloro-4-{[(4,4-dimethyl-4,5-dihydro-pyrazol-1-yl)-ethylamino-methylene]-sulfamoyl}-phenyl)-acetamide was dissolved in 5 mL MeOH, and 5 mL of concentrated HCl was added. The mixture was stirred overnight at room temperature. The mixture was basified with 2M NaOH, and extracted twice with DCM. The combined organic layers were dried over Na$_2$SO$_4$ and evaporated to dryness. The residue was purified by flash chromatography (DCM/MeOH 99:1) to give 240 mg (40%) of 4-Amino-3-chloro-N-[(4,4-dimethyl-4,5-dihydro-pyrazol-1-yl)-ethylamino-methylene]-benzenesulfonamide as an orange oil. $^1$H NMR (400 MHz, CDCl$_3$) δ 1.17 (t, J=7 Hz, 3H), 1.21 (s, 6H), 3.43-3.52 (m, 2H), 3.75 (br.s., 2H), 4.37 (br.s., 2H), 6.73 (s, 1H), 6.76 (d, J=8 Hz, 1H), 6.86 (br.s., 1H), 7.62 (dd, J=2 and 8 Hz, 1H), 7.83 (d, J=2 Hz, 1H).

2,3-Dihydro-1H-indole-5-sulfonic acid ethylamino-(4-ethyl-4,5-dihydro-pyrazol-1-yl)-methyleneamide (Compound 16)

4,N-Diethyl-4,5-dihydro-pyrazole-1-carboxamidine hydrochloride

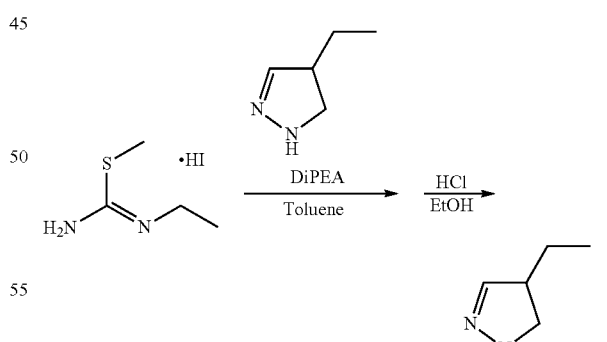

19.36 g 4-Ethyl-4,5-dihydro-1H-pyrazole was dissolved in 100 mL toluene. 48.5 g 1-Ethyl-2-methyl-isothiourea hydroiodide and 33.8 mL DiPEA were added and the mixture was refluxed for 48 hours. The mixture was concentrated, 2 M NaOH was added, followed by extraction with DCM (three times). The combined organic layers were dried over Na₂SO₄ and the solvent was evaporated in vacuo to yield 32.7 g (99%) of a red oil containing 75% of the desired product according to NMR. The oil was dissolved in EtOH and 194 mL 1 M HCl in EtOH was added dropwise. The mixture was stirred at room temperature for 30 minutes and concentrated in vacuo. Crystallization from CH₃CN:MTBE=1:1 gave 11.52 g (29%) of the desired product as a beige solid. ¹H NMR (400 MHz, DMSO-d₆) δ 0.96 (t, J=7.5 Hz, 3H), 1.16 (t, J=7 Hz, 3H), 1.46-1.72 (m, 2H), 3.32 (q, J=7 Hz, 2H), 3.35-3.45 (m, 1H), 3.55 (dd, J=10.5 and 7 Hz, 1H), 3.96 (t, J=10.5 Hz, 1H), 7.34 (d, J=2 Hz, 1H), 8.00 (br s, 2H).

1-Acetyl-2,3-dihydro-1H-indole-5-sulfonic acid ethylamino-(4-ethyl-4,5-dihydro-pyrazol-1-yl)-methyleneamide

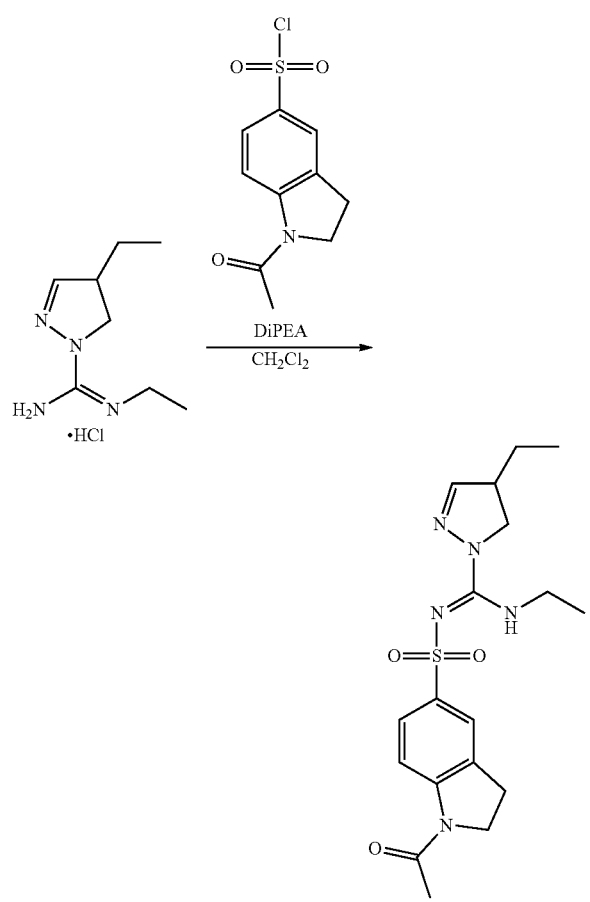

5.76 g 4,N-Diethyl-4,5-dihydro-pyrazole-1-carboxamidine hydrochloride was suspended in 100 mL DCM, 13.10 mL of DiPEA was added, followed by 5.00 g 1-acetyl-2,3-dihydro-1H-indole-5-sulfonyl chloride. The mixture was stirred overnight at room temperature. The mixture was extracted subsequently with 5% aqueous NaHCO₃ and 2M NaOH solution, the organic layer was dried over Na₂SO₄, and evaporated to dryness. The residue was purified by flash chromatography (DCM/EA 3:1→EA) to give 1.85 g (25%) of a yellow oil. ¹H NMR (400 MHz, CDCl₃) δ 0.97 (t, J=7.52 Hz, 3H), 1.15 (t, J=7.37 Hz, 3H), 1.45-1.69 (m, 2H), 2.25 (s, 3H), 3.01-3.16 (m, 1H), 3.24 (t, J=8.58 Hz, 2H), 3.42-3.52 (m, 2H), 3.64-3.75 (m, 1H), 4.02-4.21 (m, 3H), 6.90 (d, J=1.20 Hz, 1H), 7.72-7.82 (m, 2H), 8.24 (d, J=8.43 Hz, 1H) [guanidine NH invisible].

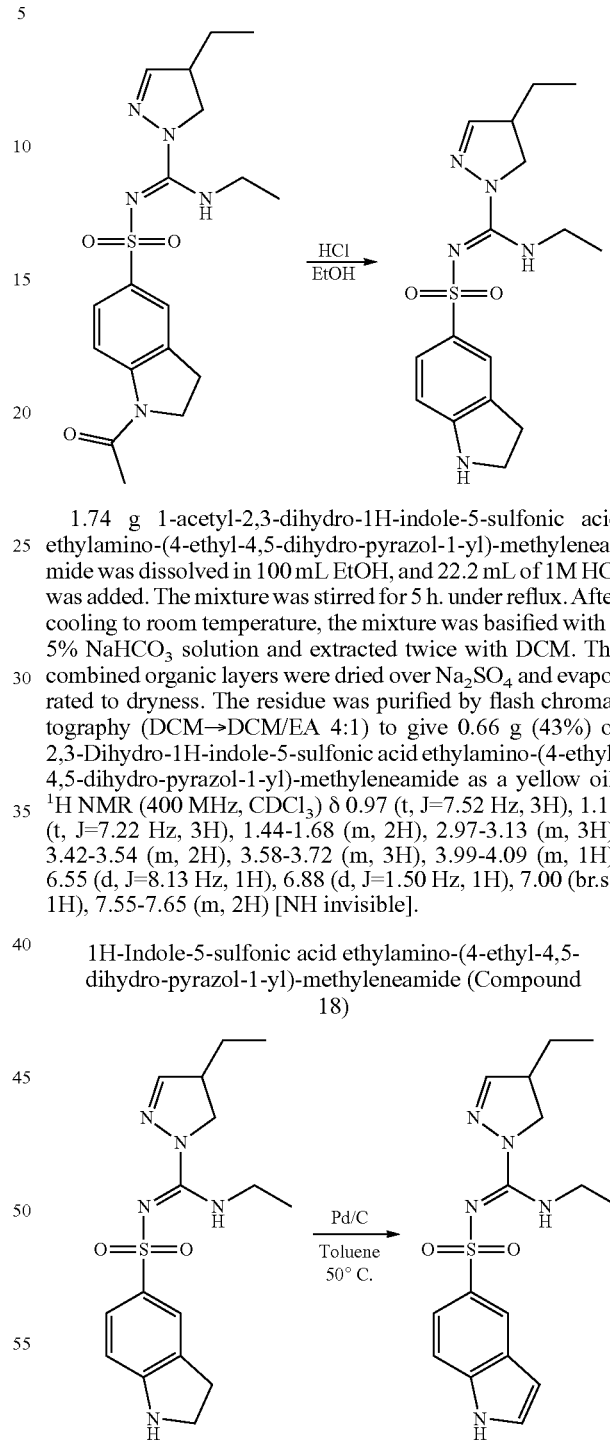

1.74 g 1-acetyl-2,3-dihydro-1H-indole-5-sulfonic acid ethylamino-(4-ethyl-4,5-dihydro-pyrazol-1-yl)-methyleneamide was dissolved in 100 mL EtOH, and 22.2 mL of 1M HCl was added. The mixture was stirred for 5 h. under reflux. After cooling to room temperature, the mixture was basified with a 5% NaHCO₃ solution and extracted twice with DCM. The combined organic layers were dried over Na₂SO₄ and evaporated to dryness. The residue was purified by flash chromatography (DCM→DCM/EA 4:1) to give 0.66 g (43%) of 2,3-Dihydro-1H-indole-5-sulfonic acid ethylamino-(4-ethyl-4,5-dihydro-pyrazol-1-yl)-methyleneamide as a yellow oil. ¹H NMR (400 MHz, CDCl₃) δ 0.97 (t, J=7.52 Hz, 3H), 1.15 (t, J=7.22 Hz, 3H), 1.44-1.68 (m, 2H), 2.97-3.13 (m, 3H), 3.42-3.54 (m, 2H), 3.58-3.72 (m, 3H), 3.99-4.09 (m, 1H), 6.55 (d, J=8.13 Hz, 1H), 6.88 (d, J=1.50 Hz, 1H), 7.00 (br.s., 1H), 7.55-7.65 (m, 2H) [NH invisible].

1H-Indole-5-sulfonic acid ethylamino-(4-ethyl-4,5-dihydro-pyrazol-1-yl)-methyleneamide (Compound 18)

0.42 g 2,3-Dihydro-1H-indole-5-sulfonic acid ethylamino-(4-ethyl-4,5-dihydro-pyrazol-1-yl)-methyleneamide was dissolved in 25 mL toluene, and 10 mol % of palladium on carbon was added. The mixture was stirred at 50° C. for 5 days, with addition of fresh catalyst (10 mol %) after 2 days. The mixture was cooled to room temperature and filtered over Hyflo. The filtrate was evaporated to dryness and the residue was purified by flash chromatography (DCM→DCM/EA 9:1) to give 0.26 g (66%) of 1H-Indole-5-sulfonic acid ethylamino-(4-ethyl-4,5-dihydro-pyrazol-1-yl)-methyleneamide as a blue oil. $^1$H NMR (400 MHz, CDCl$_3$) δ 0.87 (t, J=7.37 Hz, 3H), 1.08 (t, J=7.22 Hz, 3H), 1.32-1.59 (m, 2H), 2.89-3.02 (m, 1H), 3.35-3.50 (m, 2H), 3.58 (dd, J=11.44, 7.52 Hz, 1H), 3.96 (t, J=11.29 Hz, 1H), 6.54-6.58 (m, 1H), 6.85 (d, J=1.50 Hz, 1H), 6.97 (br.s., 1H) 7.23-7.29 (m, 1H), 7.42 (d, J=8.73 Hz, 1H), 7.69 (dd, J=8.73, 1.81 Hz, 1H), 8.24 (d, J=1.20 Hz, 1H), 9.43 (br.s., 1H).

N-[Ethylamino-(4-ethyl-4,5-dihydro-pyrazol-1-yl)-methylene]-4-hydroxybenzenesulfonamide (Compound 19)

N-[Ethylamino-(4-ethyl-4,5-dihydro-pyrazol-1-yl)-methylene]-4-methoxy-benzenesulfonamide

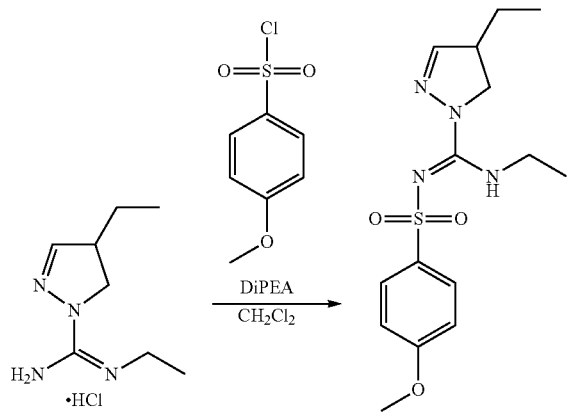

Under N$_2$ atmosphere, 0.50 g 4,N-Diethyl-4,5-dihydro-pyrazole-1-carboxamidine hydrochloride was suspended in 50 mL DCM, 0.43 mL of DiPEA was added, followed by 0.61 g 4-methoxy-benzenesulfonyl chloride. The mixture was stirred over weekend at room temperature. The mixture was extracted subsequently with 5% aqueous NaHCO$_3$ and 2M NaOH solution, the organic layer was dried over MgSO$_4$, and evaporated to dryness. The residue was purified by flash chromatography (stepwise gradient DCM→DCM/MeOH 95:5) to yield 0.28 g (28%) of product. TLC: R$_f$ 0.33 (DCM/MeOH 99:1). LC-MS: R$_t$ 1.58 min (MH+339).

In 20 mL DCM, 0.28 g N-[Ethylamino-(4-ethyl-4,5-dihydro-pyrazol-1-yl)-methylene]-4-methoxy-benzenesulfonamide was dissolved, and 3.32 mL of a 1M solution of BBr$_3$ in DCM was added. The mixture was stirred overnight at room temperature, extracted with 5% aqueous NaHCO$_3$, dried over MgSO$_4$ and evaporated to dryness. The residue was purified by flash chromatography (stepwise gradient DCM→DCM/MeOH 95:5) to yield 0.186 g (59%) of N-[Ethylamino-(4-ethyl-4,5-dihydro-pyrazol-1-yl)-methylene]-4-hydroxy-benzenesulfonamide. $^1$H NMR (400 MHz, CDCl$_3$) δ 0.95 (t, J=7.52 Hz, 3H), 1.13 (t, J=7.22 Hz, 3H), 1.50 (dq, J=14.20, 7.00 Hz, 1H), 1.60 (dq, J=14.22, 7.00 Hz, 1H), 3.01-3.16 (m, 1H), 3.43-3.50 (m, 2H), 3.66 (dd, J=11.44, 7.52 Hz, 1H), 4.05 (t, J=11.29 Hz, 1H), 6.80 (br.s., 1H), 6.87 (d, J=8.73 Hz, 2H), 6.91 (d, J=1.50 Hz, 1H), 7.78 (d, J=8.73 Hz, 2H) [guanidine NH invisible].

3-Chloro-N-[ethylamino-(4-ethyl-4,5-dihydro-pyrazol-1-yl)-methylene]-4-hydroxy-benzenesulfonamide (Compound 26)

3-Chloro-4-methoxy-benzenesulfonyl chloride

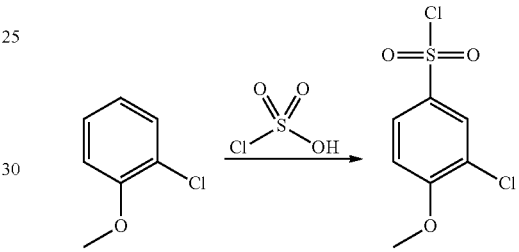

Under N$_2$ atmosphere, 41.25 mL chlorosulfonic acid was cooled in an ice bath, and under stirring 22.26 mL 2-chloroanisole was added dropwise. The mixture was heated to 55° C.; after 10 min. the heat source was removed and the mixture was stirred overnight at room temperature. The mixture was poured into ice water and extracted twice with DCM. The combined organic layers were dried over MgSO$_4$ and evaporated to dryness. The residue was purified by flash chromatography (PA/EA 9:1) to give 24.94 g (50%) of a beige oil. $^1$H NMR (400 MHz, CDCl$_3$) δ 4.03 (s, 3H), 7.08 (d, J=8.73 Hz, 1H), 7.94 (dd, J=9.03, 2.41 Hz, 1H), 8.06 (d, J=2.41 Hz, 1H).

3-Chloro-N-[ethylamino-(4-ethyl-4,5-dihydro-pyrazol-1-yl)-methylene]-4-methoxy-benzenesulfonamide

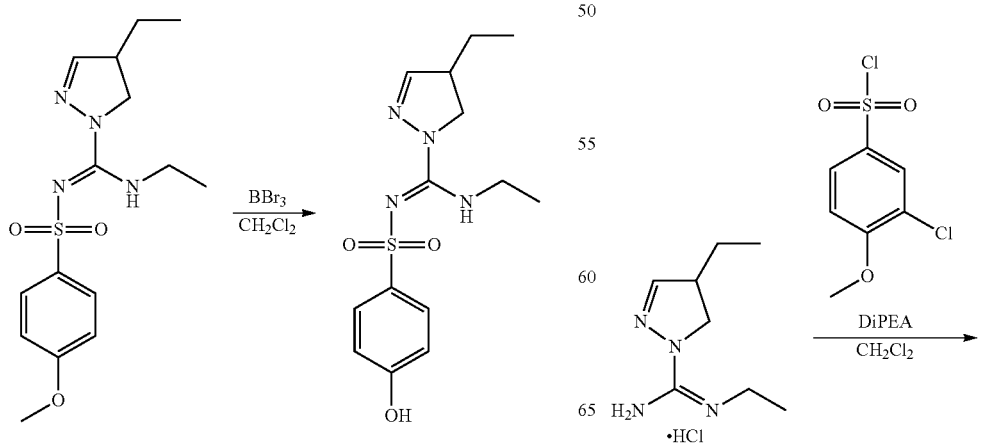

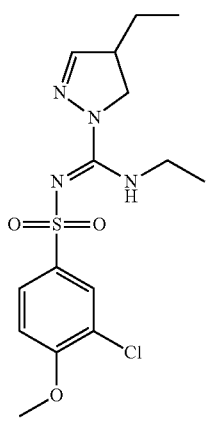

2.00 g 4,N-Diethyl-4,5-dihydro-pyrazole-1-carboxamidine hydrochloride was suspended in 100 mL DCM, 10.76 mL of DiPEA was added, followed by 3.79 g 3-Chloro-4-methoxy-benzenesulfonyl chloride. The mixture was stirred over weekend at room temperature and subsequently evaporated to dryness. The residue was purified by flash chromatography (stepwise gradient DCM→DCM/EA 9:1 followed by DCM/MeOH 98:2) to yield 1.38 g (24%) of a colorless oil. $^1$H NMR (400 MHz, CDCl$_3$) δ 0.98 (t, J=7.52 Hz, 3H), 1.17 (t, J=7.22 Hz, 3H), 1.45-1.69 (m, 2H), 3.05-3.16 (m, 1H), 3.43-3.53 (m, 2H), 3.70 (dd, J=11.29, 7.67 Hz, 1H), 3.95 (s, 3H), 4.04-4.13 (m, 1H), 6.80 (br.s., 1H), 6.92 (d, J=1.50 Hz, 1H), 6.95 (d, J=8.43 Hz, 1H), 7.82 (dd, J=8.73, 2.41 Hz, 1H), 7.95 (d, J=2.11 Hz, 1H).

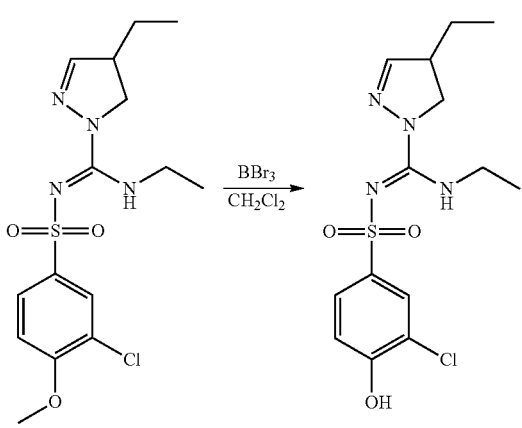

In 25 mL DCM, 1.09 g 3-chloro-N-[ethylamino-(4-ethyl-4,5-dihydro-pyrazol-1-yl)-methylene]-4-methoxy-benzenesulfonamide was dissolved, and 11.69 mL of a 1M solution of BBr$_3$ in DCM was added. The mixture was stirred overnight at room temperature, extracted with 5% aqueous NaHCO$_3$, dried over MgSO$_4$ and evaporated to dryness. The residue was purified by flash chromatography (DCM/EA 95:5) to yield 0.89 g (84%) of 3-Chloro-N-[ethylamino-(4-ethyl-4,5-dihydro-pyrazol-1-yl)-methylene]-4-hydroxy-benzenesulfonamide as a yellow oil. $^1$H NMR (400 MHz, CDCl$_3$) δ 0.97 (t, J=7.52 Hz, 3H), 1.16 (t, J=7.22 Hz, 3H), 1.46-1.70 (m, 2H), 3.05-3.18 (m, 1H), 3.43-3.54 (m, 2H), 3.69 (dd, J=11.14, 7.52 Hz, 1H), 4.04-4.12 (m, 1H), 6.05 (br.s., 1H), 6.83 (br.s., 1H), 6.93 (d, J=1.50 Hz, 1H), 7.06 (d, J=8.43 Hz, 1H), 7.75 (dd, J=8.73, 2.11 Hz, 1H), 7.94 (d, J=2.11 Hz, 1H).

3-Amino-N-[(4,4-dimethyl-4,5-dihydro-pyrazol-1-yl)-ethylamino-methylene]-benzenesulfonamide (Compound 30)

N-[(4,4-Dimethyl-4,5-dihydro-pyrazol-1-yl)-ethylamino-methylene]-3-nitro-benzenesulfonamide

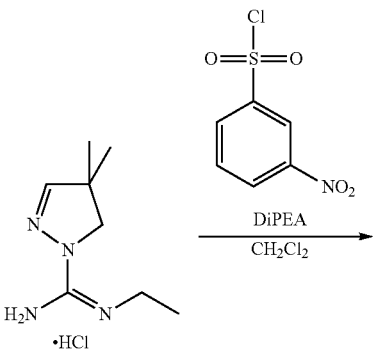

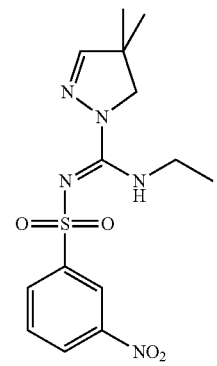

1.50 g N-Ethyl-4,4-dimethyl-4,5-dihydro-pyrazole-1-carboxamidine hydrochloride was suspended in 50 mL DCM, 5.02 mL of DiPEA was added, followed by 1.95 g 3-nitro-benzenesulfonyl chloride. The mixture was stirred overnight at room temperature and extracted with 5% aqueous NaHCO$_3$. The water layer was acidified with 1M HCl and extracted with DCM. The organic phase was dried over MgSO$_4$ and evaporated to dryness to give 2.18 g (84%) of a brown oil. $^1$H NMR (400 MHz, CDCl$_3$) δ 1.19 (t, J=7.22 Hz, 3H), 1.25 (s, 6H), 3.44-3.53 (m, 2H), 3.83 (br.s., 2H), 6.80 (s, 1H), 7.66 (t, J=7.98 Hz, 1H), 8.28 (d, J=7.82 Hz, 1H), 8.34 (dd, J=8.13, 1.20 Hz, 1H).

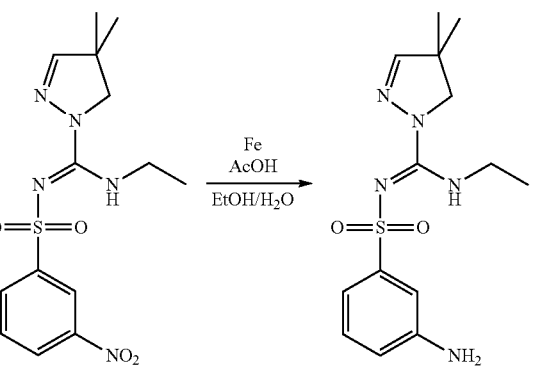

In a mixture of 50 mL EtOH and 25 mL water, 1.11 g N-[(4,4-Dimethyl-4,5-dihydro-pyrazol-1-yl)-ethylamino-methylene]-3-nitro-benzenesulfonamide was dissolved. Subsequently, 1.05 g iron and 1.08 mL acetic acid were added, and the mixture was refluxed for 4 h. After cooling to room temperature, the mixture was filtered over Hyflo and the Hyflo was rinsed with MeOH. The alcohols were evaporated from the filtrate, and 5% aqueous NaHCO$_3$ and DCM were added. The material insoluble in these phases was filtered off, the organic phase was separated and the aqueous phase extracted once more with DCM. The combined organic layers were dried over MgSO$_4$ and evaporated to dryness to give 1.02 g (100%) of 3-amino-N-[(4,4-dimethyl-4,5-dihydro-pyrazol-1-yl)-ethylamino-methylene]-benzenesulfonamide as a brown foam. $^1$H NMR (400 MHz, CDCl$_3$) δ 1.14 (t, J=7.22 Hz, 3H), 1.19 (s, 6H), 3.42-3.51 (m, 2H), 3.73 (s, 2H), 3.93 (br.s., 2H), 6.71-6.79 (m, 2H), 6.90 (br.s., 1H), 7.20 (t, J=7.83 Hz, 1H), 7.24-7.31 (m, 2H).

5-Bromo-2,3-dihydro-1H-indole-6-sulfonic acid ethylamino-(4-ethyl-4,5-dihydro-pyrazol-1-yl)-methyleneamide (Compound 32)

1-Acetyl-5-bromo-2,3-dihydro-1H-indole-6-sulfonyl chloride

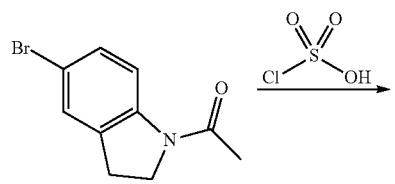

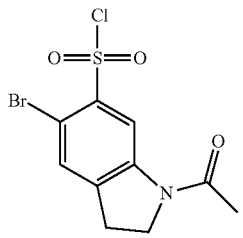

Under N$_2$ atmosphere, 25.00 mL chlorosulfonic acid was cooled in an ice bath, and under stirring 5.00 g 1-acetyl-5-bromoindoline was added portionwise. Stirring was continued for 20 min. after which the ice bath was removed and the mixture was heated to 70° C. After cooling to room temperature, the mixture was cautiously poured into ice water and extracted twice with DCM. The combined organic layers were dried over MgSO$_4$ and evaporated to dryness to give 6.57 g (93%) of a beige solid. $^1$H NMR (400 MHz, DMSO-d$_6$) δ 2.16 (s, 3H), 3.15 (t, J=8.58 Hz, 2H), 4.11 (t, J=8.58 Hz, 2H), 7.37 (s, 1H), 8.66 (s, 1H).

1-Acetyl-5-bromo-2,3-dihydro-1H-indole-6-sulfonic acid ethylamino-(4-ethyl-4,5-dihydro-pyrazol-1-yl)-methyleneamide

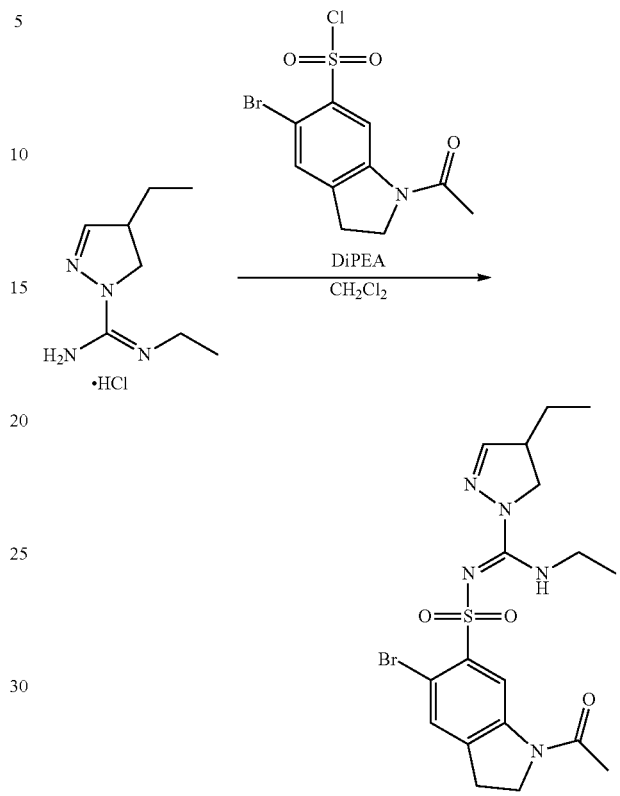

1.94 g 4,N-Diethyl-4,5-dihydro-pyrazole-1-carboxamidine hydrochloride was suspended in 50 mL DCM, 4.58 mL of DiPEA was added, followed by 2.34 g 1-acetyl-5-bromo-2,3-dihydro-1H-indole-6-sulfonyl chloride. The mixture was stirred overnight at room temperature and subsequently evaporated to dryness. The residue was purified by flash chromatography (gradient DCM/EA 95:5→75:25) to yield 0.65 g (16%) of a brown oil. $^1$H NMR (400 MHz, CDCl$_3$) δ 0.98 (t, J=7.37 Hz, 3H), 1.13-1.21 (m, 3H), 1.43-1.80 (m, 2H), 2.22 (s, 3H), 3.11 (br.s., 1H), 3.17-3.27 (m, 2H), 3.48-3.58 (m, 2H), 3.73-3.84 (m, 1H), 4.04-4.27 (m, 3H), 6.91 (s, 1H), 7.47 (s, 1H), 8.99 (s, 1H). [guanidine NH invisible].

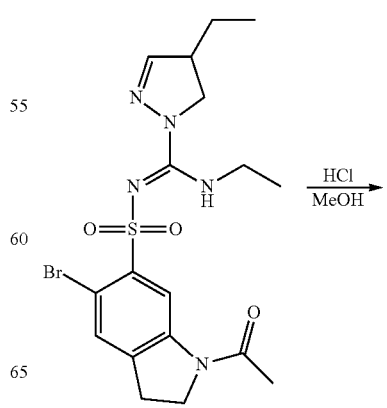

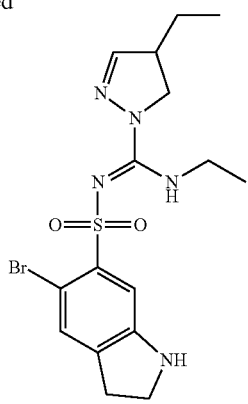

0.65 g 1-Acetyl-5-bromo-2,3-dihydro-1H-indole-6-sulfonic acid ethylamino-(4-ethyl-4,5-dihydro-pyrazol-1-yl)-methyleneamide was dissolved in 20 mL MeOH and 20.7 mL of 1M HCl in MeOH was added. The mixture was stirred overnight under reflux. After cooling to room temperature, the mixture was basified with a 5% NaHCO₃ solution and extracted twice with DCM. The combined organic layers were dried over Na₂SO₄ and evaporated to dryness. The residue was purified by flash chromatography (DCM/EA 9:1→8:2) to give 0.35 g (64%) of 5-Bromo-2,3-dihydro-1H-indole-6-sulfonic acid ethylamino-(4-ethyl-4,5-dihydro-pyrazol-1-yl)-methyleneamide as a yellow oil. ¹H NMR (400 MHz, CDCl₃) δ 0.96 (t, J=7.37 Hz, 3H), 1.17 (t, J=7.22 Hz, 3H), 1.45-1.68 (m, 2H), 3.00-3.15 (m, 3H), 3.48-3.57 (m, 2H), 3.62 (t, J=8.43 Hz, 2H), 3.71 (dd, J=11.14, 7.52 Hz, 1H), 3.91 (br.s., 1H), 4.08-4.17 (m, 1H), 6.76 (br.s., 1H), 6.90 (d, J=1.50 Hz, 1H), 7.34 (s, 1H), 7.46 (s, 1H).

2,3-Dihydro-1H-indole-6-sulfonic acid ethylamino-(4-ethyl-4,5-dihydro-pyrazol-1-yl)-methyleneamide (Compound 33)

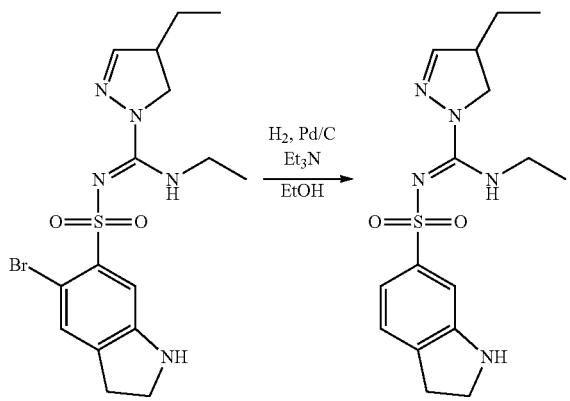 [SMILES: "EtOH" ; CCN/C(=N\S(=O)(=O)c1cc2c(cc1Br)CCN2)N1CC(CC)C=N1 ; CCN/C(=N\S(=O)(=O)c1ccc2c(c1)NCC2)N1CC(CC)C=N1]

To a solution of 0.30 g 5-Bromo-2,3-dihydro-1H-indole-6-sulfonic acid ethylamino-(4-ethyl-4,5-dihydro-pyrazol-1-yl)-methyleneamide in 50 mL EtOH was added 0.94 mL of triethylamine. The mixture was degassed thoroughly, and 10 mol % of palladium on carbon was added. The mixture was hydrogenated overnight at a H₂ pressure of 1 atm. The mixture was filtered over Hyflo, the Hyflo was washed with EtOH, and the filtrate was concentrated in vacuo. The residue was purified by flash chromatography (DCM→DCM/EA 95:5→DCM/EA 9:1) to give 0.20 g (76%) of 2,3-Dihydro-1H-indole-6-sulfonic acid ethylamino-(4-ethyl-4,5-dihydro-pyrazol-1-yl)-methyleneamide as a red oil. ¹H NMR (400 MHz, CDCl₃) δ 0.96 (t, J=7.52 Hz, 3H), 1.14 (t, J=7.22 Hz, 3H), 1.43-1.67 (m, 2H), 3.04 (t, J=8.43 Hz, 3H), 3.42-3.52 (m, 2H), 3.60 (t, J=8.43 Hz, 2H), 3.66 (dd, J=11.44, 7.83 Hz, 1H), 4.06 (t, J=11.29 Hz, 1H), 6.89 (d, J=1.50 Hz, 1H), 7.10-7.15 (m, 2H), 7.24-7.27 (m, 1H). [NH's invisible].

1H-Indole-6-sulfonic acid ethylamino-(4-ethyl-4,5-dihydro-pyrazol-1-yl)-methyleneamide (Compound 34)

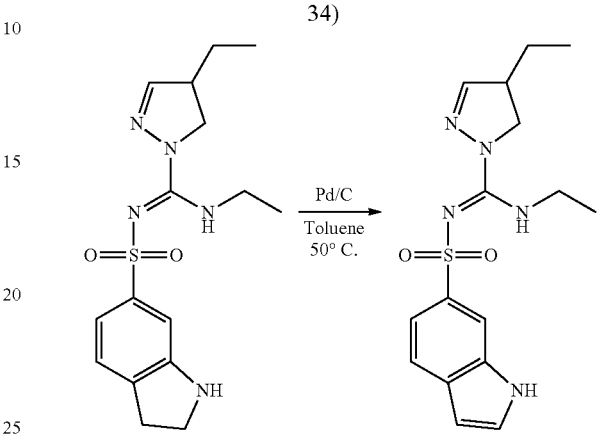

0.14 g 2,3-Dihydro-1H-indole-6-sulfonic acid ethylamino-(4-ethyl-4,5-dihydro-pyrazol-1-yl)-methyleneamide was dissolved in 25 mL toluene, the mixture was degassed, and 10 mol % of palladium on carbon was added. The mixture was stirred overnight at 50° C. The mixture was cooled to room temperature and filtered over Hyflo, and the Hyflo was washed with toluene. The filtrate was evaporated to dryness and the residue was purified by flash chromatography (DCM→DCM/EA 95:5→DCM/EA 8:2) to give 70 mg of 1H-Indole-6-sulfonic acid ethylamino-(4-ethyl-4,5-dihydro-pyrazol-1-yl)-methyleneamide as a white amorphous solid. ¹H NMR (400 MHz, CDCl₃) δ 0.86 (t, J=7.52 Hz, 3H), 1.06 (t, J=7.22 Hz, 3H), 1.32-1.57 (m, 2H), 2.89-3.00 (m, 1H), 3.35-3.54 (m, 3H), 3.89 (t, J=11.44 Hz, 1H), 6.54 (br.s., 1H), 6.84 (d, J=1.50 Hz, 1H), 6.96 (br.s., 1H), 7.36 (t, J=2.86 Hz, 1H), 7.59-7.70 (m, 2H), 8.26 (d, J=1.20 Hz, 1H), 9.55 (br.s., 1H).

N-[(4,4-Dimethyl-4,5-dihydro-pyrazol-1-yl)-ethylamino-methylene]-3-hydroxy-benzenesulfonamide (Compound 36)

N-[(4,4-Dimethyl-4,5-dihydro-pyrazol-1-yl)-ethylamino-methylene]-3-methoxybenzenesulfonamide

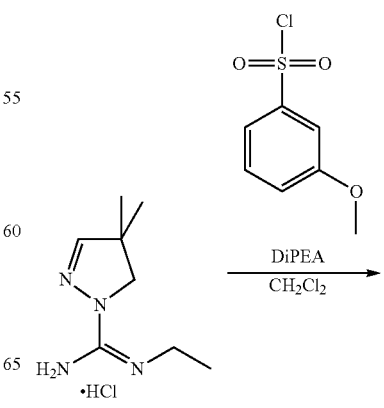

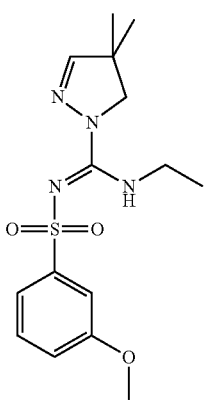

2.5 g N-Ethyl-4,4-dimethyl-4,5-dihydro-pyrazole-1-carboxamidine hydrochloride was suspended in 20 mL DCM, 4.39 mL of DiPEA was added, followed by 2.52 g 3-methoxy-benzenesulfonyl chloride. The mixture was stirred over weekend at room temperature. The mixture was extracted subsequently with 5% aqueous NaHCO$_3$ and 2M NaOH solution, the organic layer was dried over Na$_2$SO$_4$, and evaporated to dryness. The residue was purified by flash chromatography (DCM/MeOH 99.5:0.5→99:1) to give 2.95 g (71%) of an orange oil. $^1$H NMR (400 MHz, CDCl$_3$) δ 1.16 (t, J=7 Hz, 3H), 1.22 (s, 6H), 3.43-3.52 (m, 2H), 3.79 (br.s., 2H), 3.85 (s, 3H), 6.74 (s, 1H), 6.85 (br.s., 1H), 7.01 (dd, J=8 and 2.5 Hz, 1H), 7.35 (t, J=8 Hz, 1H), 7.46-7.50 (m, 1H), 7.53 (br d, J=8 Hz, 1H).

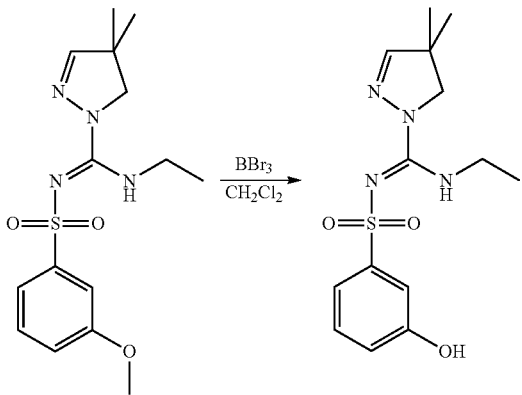

In 20 mL DCM, 2.32 g N-[(4,4-Dimethyl-4,5-dihydro-pyrazol-1-yl)-ethylamino-methylene]-3-methoxy-benzenesulfonamide was dissolved, and 13.7 mL of a 1M solution of BBr$_3$ in DCM was added. The mixture was stirred over weekend at room temperature. A 5% aqueous NaHCO$_3$ solution was added to quench the mixture that contained a sticky precipitate; after quenching, this was dissolved by gently heating the mixture. The organic layer was separated and the aqueous layer was extracted once more with DCM. The combined organic layers were dried over Na$_2$SO$_4$ and evaporated to dryness. The residue was purified by flash chromatography (DCM/MeOH 99:1→98:2) to yield 1.24 g (56%) N-[(4,4-Dimethyl-4,5-dihydro-pyrazol-1-yl)-ethylamino-methylene]-3-hydroxybenzenesulfonamide as of a beige powder. $^1$HNMR (400 MHz, CDCl$_3$) δ 1.09 (t, J=7 Hz, 3H), 1.14 (s, 6H), 3.40-3.50 (m, 2H), 3.58 (br.s., 2H), 6.72 (s, 1H), 6.79 (br.s., 1H), 6.97-7.03 (m, 1H), 7.25-7.34 (m, 2H), 7.46 (br d, J=8 Hz, 1H), 7.66 (br s, 1H).

3-Chloro-N-[(4,4-dimethyl-4,5-dihydro-pyrazol-1-yl)-ethylamino-methylene]-5-hydroxy-benzenesulfonamide (Compound 38)

3-Bromo-5-chloro-phenol

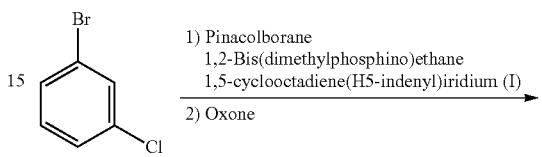

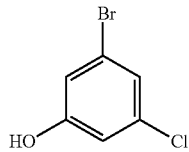

Under an atmosphere of dry nitrogen, 103 mg 1,5-cyclooctadiene(H5-indenyl)iridium (I) was put in a 25 mL Pyrex bottle. Subsequently were added 0.04 mL 1,2-bis(dimethylphosphino)ethane, 0.61 mL 3-bromochlorobenzene and 1.52 mL pinacolborane. The mixture was stirred at 150° C. for 3.5 h. After cooling to room temperature, the borane adduct was taken up in 17 mL acetone to give a clear solution. This solution was added slowly to 17.41 mL of a 0.30 M solution of oxone in water cooled in an ice bath. The mixture was stirred vigorously for 15 min. at room temperature and extracted three times with DCM. The combined organic phases were dried over Na$_2$SO$_4$ and evaporated to dryness. The residue was purified by flash chromatography (DCM) to yield 750 mg (62%) of a beige solid. $^1$H NMR complies with known data (compound (1), Maleczka, 2003).

1-Benzyloxy-3-bromo-5-chloro-benzene

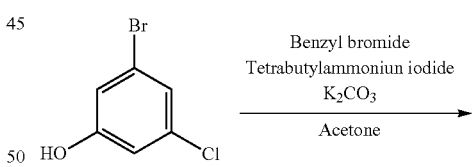

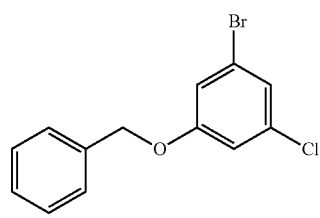

2.54 g 3-Bromo-5-chloro-phenol was dissolved in 50 mL acetone. Subsequently were added 8.04 g potassium carbonate, 1.52 mL benzyl bromide and 0.86 g tetrabutylammonium iodide. The mixture was refluxed for 2 h., cooled to room temperature and filtrated, and the filtrate was concentrated to dryness. The residue was chromatographed over a short column of silica, eluting with DCM/PA 1:4, and the pink color of the product fractions (at the front) was removed with active carbon. After filtration and evaporation, 3.11 g (90%) of a pale yellow oil was obtained. ¹H NMR (400 MHz, CDCl₃) δ 5.03 (s, 2H), 6.92 (t, J=2 Hz, 1H), 7.03 (t, J=2 Hz, 1H), 7.12 (t, J=1.5 Hz, 1H), 7.31-7.45 (m, 5H).

3-Benzyloxy-5-chloro-benzenesulfonyl chloride

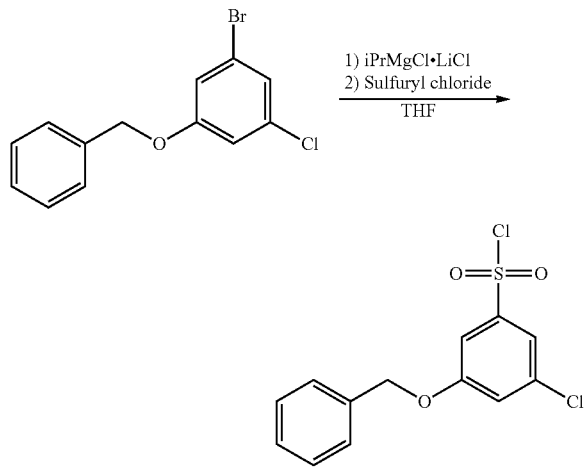

Under N₂ atmosphere, 2.23 g 1-benzyloxy-3-bromo-5-chloro-benzene was dissolved in 50 mL dry THF, and the mixture was cooled in an ice bath. Dropwise, 14.84 mL of a 1M solution of isopropyl magnesium chloride—lithium chloride complex was added, and the mixture was stirred at room temperature overnight. After cooling to −40° C., 2.41 mL of sulfuryl chloride was added in one portion (T raised to 10° C.), and the mixture was stirred for 15 minutes at room temperature. After cooling with an ice bath, the mixture was quenched with water and acidified with 1M aqueous HCl. The mixture was extracted with MTBE, and the organic phase was dried over Na₂SO₄ and evaporated to dryness. The residue was purified by flash chromatography (PA→PA/Et₂O 95:5) to yield 1.53 g (62%) of a colorless oil. ¹H NMR (400 MHz, CDCl₃) δ 5.14 (s, 2H), 7.30 (t, J=2 Hz, 1H), 7.34-7.47 (m, 5H), 7.50 (t, J=2 Hz, 1H), 7.62 (t, J=1.5 Hz, 1H).

3-Benzyloxy-5-chloro-N-[(4,4-dimethyl-4,5-dihydro-pyrazol-1-yl)-ethylamino-methylene]-benzenesulfonamide

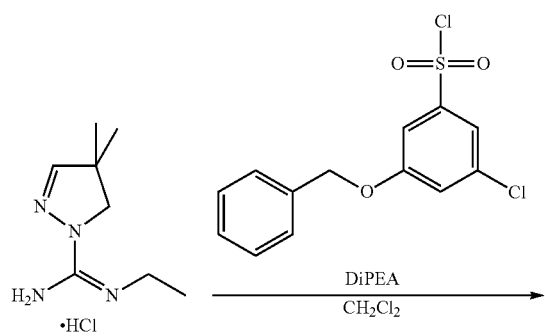

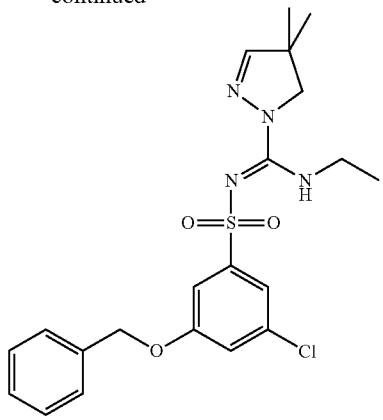

0.93 g N-Ethyl-4,4-dimethyl-4,5-dihydro-pyrazole-1-carboxamidine hydrochloride was suspended in 10 mL DCM, 1.71 mL of DiPEA was added, followed by 1.52 g 3-benzyloxy-5-chloro-benzenesulfonyl chloride. The mixture was stirred over weekend at room temperature. The mixture was extracted subsequently with 5% aqueous NaHCO₃ and 2M NaOH solution, the organic layer was dried over Na₂SO₄, and evaporated to dryness. The residue was purified by flash chromatography (DCM/acetone 99:1) to give 1.28 g (62%) of an orange oil. ¹H NMR (400 MHz, CDCl₃) δ 1.16 (t, J=7 Hz, 3H), 1.23 (s, 6H), 3.40-3.50 (m, 2H), 3.77 (br.s., 2H), 5.09 (s, 2H), 6.77 (s, 1H), 6.80 (br.s., 1H), 7.07 (t, J=2 Hz, 1H), 7.31-7.48 (m, 6H), 7.51-7.55 (m, 1H).

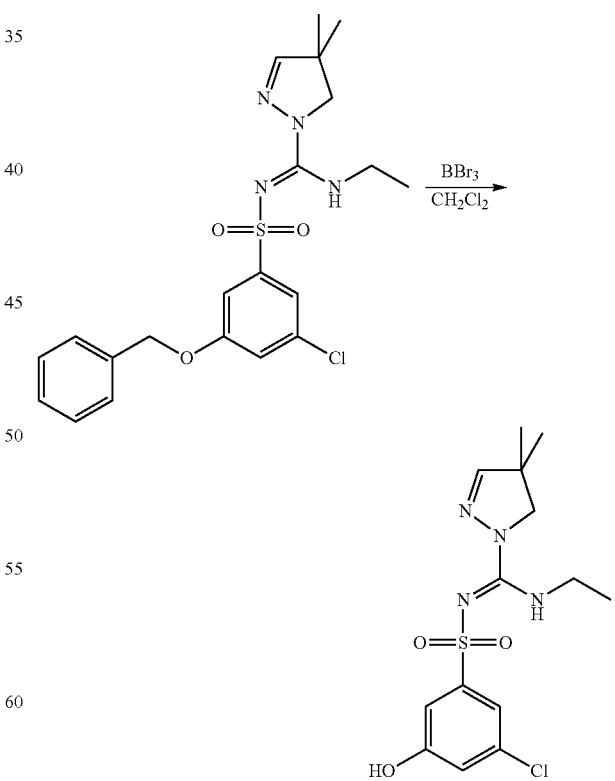

In 10 mL DCM, 1.28 g 3-benzyloxy-5-chloro-N-[(4,4-dimethyl-4,5-dihydro-pyrazol-1-yl)-ethyl-amino-methylene]-benzenesulfonamide was dissolved, and after cooling in an ice bath 5.64 mL of a 1M solution of BBr₃ in DCM was added dropwise. The mixture was stirred at room temperature for 1 h. and quenched with a 5% aqueous NaHCO₃ solution. The organic layer was separated and the aqueous layer was extracted once more with DCM. The combined organic layers were dried over Na₂SO₄ and evaporated to dryness. The residue was purified by flash chromatography (DCM/MeOH 99:1→98:2) to yield 0.93 g (92%) of 3-Chloro-N-[(4,4-dimethyl-4,5-dihydro-pyrazol-1-yl)-ethylamino-methylene]-5-hydroxy-benzenesulfonamide as a white amorphous solid. ¹H NMR (400 MHz, CDCl₃) δ 1.13 (t, J=7 Hz, 3H), 1.16 (s, 6H), 3.41-3.51 (m, 2H), 3.56 (br.s., 2H), 6.75 (br.s., 1H), 6.76 (s, 1H), 6.99 (t, J=2 Hz, 1H), 7.44 (t, J=1.75 Hz, 1H), 7.54 (dd, J=2 and 1.75 Hz, 1H), 7.72 (br.s., 1H).

4-Aminomethyl-N-[(2,3-diaza-spiro[4.4]non-3-en-2-yl)-ethylamino-methylene]-benzenesulfonamide
(Compound 39)

N-Ethyl-2,3-diaza-spiro[4.4]non-3-ene-2-carboxamidine

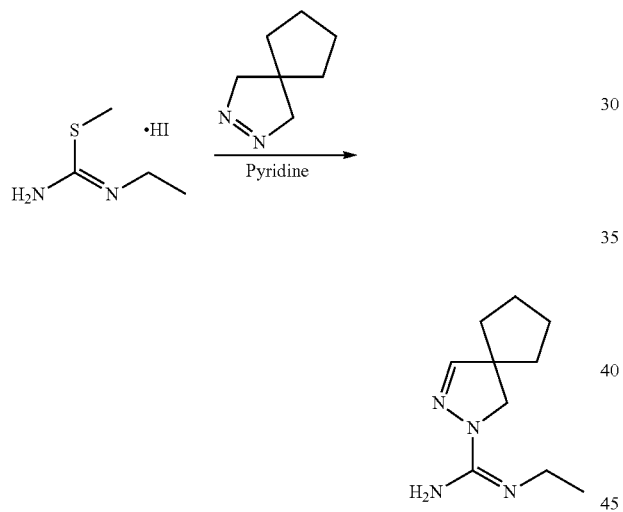

40.89 g 1-Ethyl-2-methyl-isothiourea hydroiodide was dissolved in 150 mL pyridine at 40° C. Subsequently, 20.00 g 2,3-diaza-spiro[4.4]non-2-ene was added and the mixture was stirred overnight under reflux. The mixture was cooled to 60° C. and concentrated under reduced pressure, and the orange residue was taken up in DCM (250 mL). The organic phase was extracted 3 times with water, dried over Na₂SO₄ and evaporated under reduced pressure. Residual pyridine was removed by azeotropic destillation with water under reduced pressure at 60° C., and residual water was removed by azeotropic destillation with isopropanol under reduced pressure at 60° C. This yielded 31.5 g of a yellow/brown oil containing ~80% of anticipated product which was used in subsequent steps without further purification. ¹H NMR (400 MHz, CDCl₃) δ 1.35 (t, J=7.22 Hz, 3H), 1.57-1.99 (m, 8H), 3.60 (q, J=7.22 Hz, 2H), 4.04 (s, 2H), 7.03 (s, 1H) [guanidine NH₂ invisible].

4-(1,3-Dioxo-1,3-dihydro-isoindol-2-ylmethyl)-benzenesulfonyl chloride

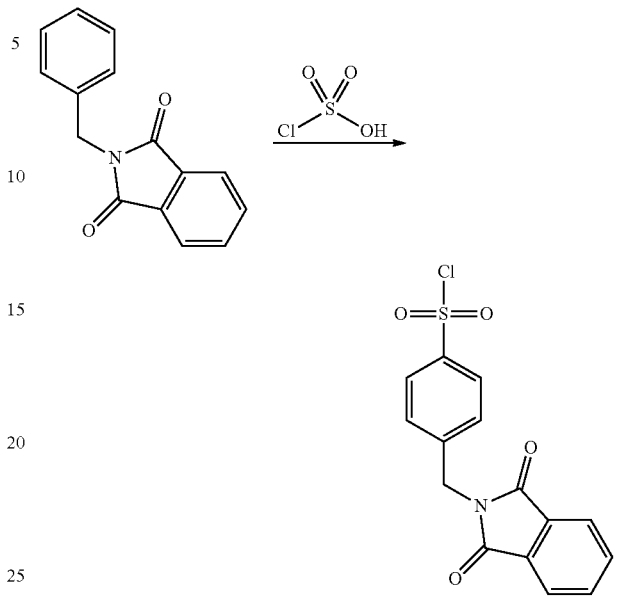

Under N₂ atmosphere, 11.26 mL chlorosulfonic acid was cooled in an ice bath, and under stirring 10.00 g n-benzylphthalimide was added portionwise over a period of 20 min. The ice bath was removed and the mixture was heated to 60° C. for 30 min. After cooling to room temperature, the mixture was cautiously poured into ice water and extracted twice with chloroform. The combined organic layers were dried over MgSO₄ and concentrated to a small volume. The product was obtained by trituration of the concentrate with PA to give 10.44 g (73%) of a white powder. ¹H NMR (400 MHz, CDCl₃) δ 4.95 (s, 2H), 7.67 (d, J=8.43 Hz, 2H), 7.73-7.78 (m, 2H), 7.85-7.90 (m, 2H), 8.00 (d, J=8.43 Hz, 2H).

N-[(2,3-Diaza-spiro[4.4]non-3-en-2-yl)-ethylaminomethylene]-4-(1,3-dioxo-1,3-dihydro-isoindol-2-ylmethyl)-benzenesulfonamide

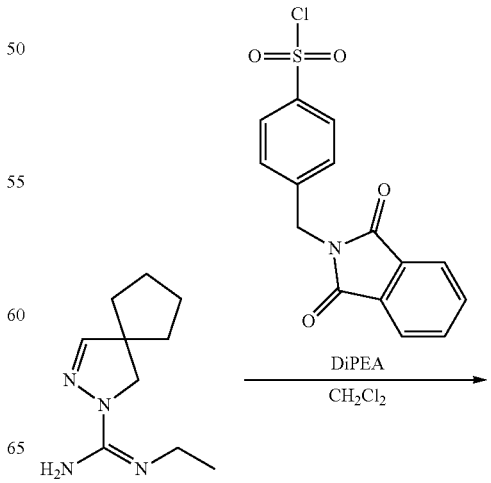

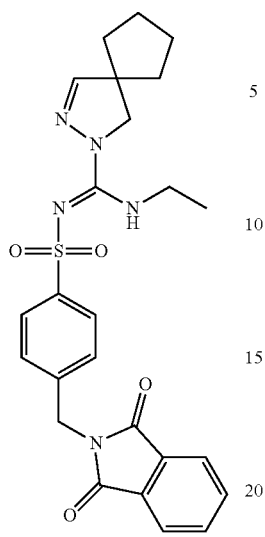

3.07 g N-Ethyl-2,3-diaza-spiro[4.4]non-3-ene-2-carboxamidine was taken up in 200 mL DCM, 10.83 mL of DiPEA was added, followed by 5.00 g 4-(1,3-Dioxo-1,3-dihydro-isoindol-2-ylmethyl)-benzenesulfonyl chloride. The mixture was stirred overnight at room temperature. The mixture was extracted subsequently with 5% aqueous NaHCO$_3$ and 2M NaOH solution, the organic layer was dried over Na$_2$SO$_4$, and evaporated to dryness. The residue was purified by flash chromatography (PA/EA 1:1) to give 2.51 g (38%) of a brown oil. $^1$H NMR (400 MHz, CDCl$_3$) δ 1.13 (t, J=7.22 Hz, 3H), 1.60-1.82 (m, 8H), 3.41-3.50 (m, 2H), 3.81 (br.s., 2H), 4.89 (s, 2H), 6.79 (s, 1H), 7.49 (d, J=8.43 Hz, 2H), 7.70-7.76 (m, 2H), 7.81-7.87 (m, 2H), 7.88 (d, J=8.43 Hz, 2H) [guanidine NH invisible].

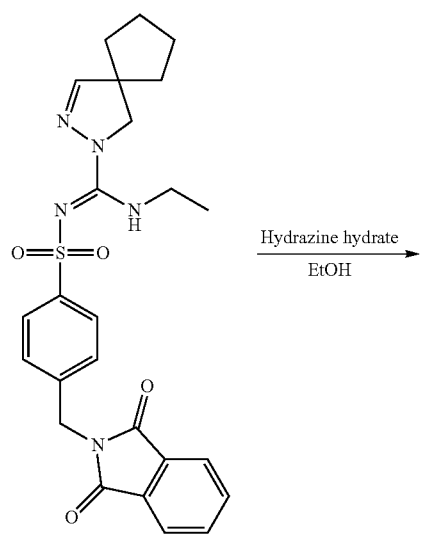

Hydrazine hydrate
EtOH

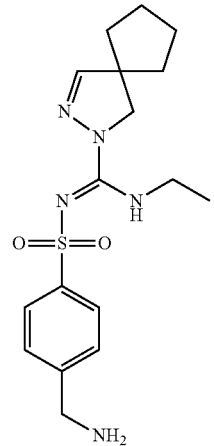

2.51 g N-[(2,3-Diaza-spiro[4.4]non-3-en-2-yl)-ethylamino-methylene]-4-(1,3-dioxo-1,3-dihydro-isoindol-2-ylmethyl)-benzenesulfonamide was taken up in 50 mL EtOH. After addition of 0.70 mL hydrazine hydrate, the mixture was refluxed for 2 h. After cooling to room temperature, the formed precipitate was filtered off. The filtrate was concentrated, and the residue was triturated with DCM. The solids were filtered off, and the filtrate was evaporated to dryness to give 1.20 g (67%) of 4-Aminomethyl-N-[(2,3-diaza-spiro[4.4]non-3-en-2-yl)-ethylamino-methylene]benzenesulfonamide as a red oil. $^1$H NMR (400 MHz, CDCl$_3$) δ 1.14 (t, J=7.22 Hz, 3H), 1.59-1.83 (m, 8H), 3.46 (q, 2H), 3.82 (br.s., 2H), 3.92 (br.s., 2H), 6.82 (s, 1H), 7.40 (d, J=8.13 Hz, 2H), 7.88 (d, J=8.13 Hz, 2H) [NH$_2$ & guanidine NH invisible].

4-{[(4,4-Dimethyl-4,5-dihydro-pyrazol-1-yl)-ethylamino-methylene]-sulfamoyl}-benzamidine (Compound 41)

4-Cyano-N-[(4,4-dimethyl-4,5-dihydro-pyrazol-1-yl)-ethylamino-methylene]-benzenesulfonamide

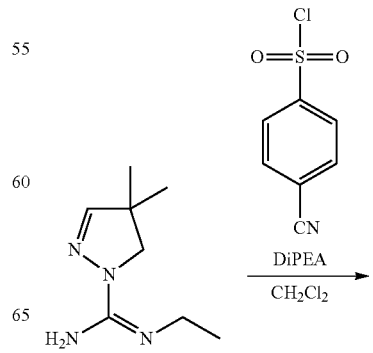

DiPEA
CH$_2$Cl$_2$

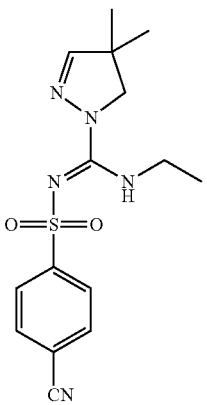

500 mg N-Ethyl-4,4-dimethyl-4,5-dihydro-pyrazole-1-carboxamidine was suspended in 10 mL dichloromethane; 0.92 mL (2.2 equiv.) DiPEA was added and subsequently 0.49 g (1.0 equiv.) 4-cyanobenzenesulfonyl chloride. The mixture was stirred overnight at room temperature. The reaction mixture was extracted with 5% aqueous NaHCO$_3$ and 2 M aqueous NaOH, dried over Na$_2$SO$_4$ and concentrated under reduced pressure to yield 680 mg (82%) of a brown oil. $^1$H NMR (400 MHz, CDCl$_3$) δ 1.16 (t, J=7 Hz, 3H), 1.25 (s, 6H), 3.39-3.50 (m, 2H), 3.81 (s, 2H), 6.71 (br s, 1H), 6.79 (s, 1H), 7.73-7.79 (m, 2H), 8.02-8.09 (m, 2H).

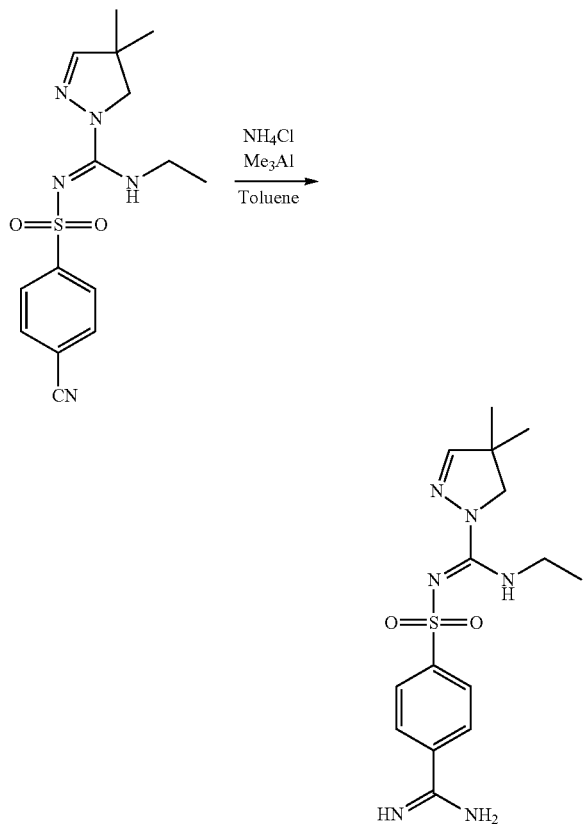

1.08 g (10 equiv.) ammonium chloride was suspended in 10 mL toluene and the mixture was cooled in an ice bath. Dropwise, 10.12 mL of a 2 M solution of trimethylaluminium (10 equiv.) was added, the ice bath was removed and the mixture was stirred at room temperature for 30 minutes. Subsequently, a solution of 0.71 g 4-cyano-N-[(4,4-dimethyl-4,5-dihydro-pyrazol-1-yl)-ethylamino-methylene]-benzenesulfonamide in 10 mL toluene was added dropwise, and the mixture was stirred at 80° C. overnight. After cooling down, the mixture was diluted with ethyl acetate and extracted with 2 M NaOH. The combined organic layers were dried over Na$_2$SO$_4$, filtered and concentrated under reduced pressure. Purification with flash column chromatography (MeOH/Et$_3$N 97:3) yielded 310 mg (43%) of an off-white amorph. $^1$H NMR (400 MHz, CDCl$_3$) δ 1.17 (t, J=7 Hz, 3H), 1.23 (s, 6H), 3.41-3.53 (m, 2H), 3.80 (s, 2H), 6.77 (s, 1H), 6.80 (br s, 1H), 7.66-7.74 (m, 2H), 7.94-8.02 (m, 2H).

3-{[(4,4-Dimethyl-4,5-dihydro-pyrazol-1-yl)-ethylamino-methylene]-sulfamoyl}-benzamidine (Compound 42)

3-Cyano-N-[(4,4-dimethyl-4,5-dihydro-pyrazol-1-yl)-ethylamino-methylene]-benzenesulfonamide

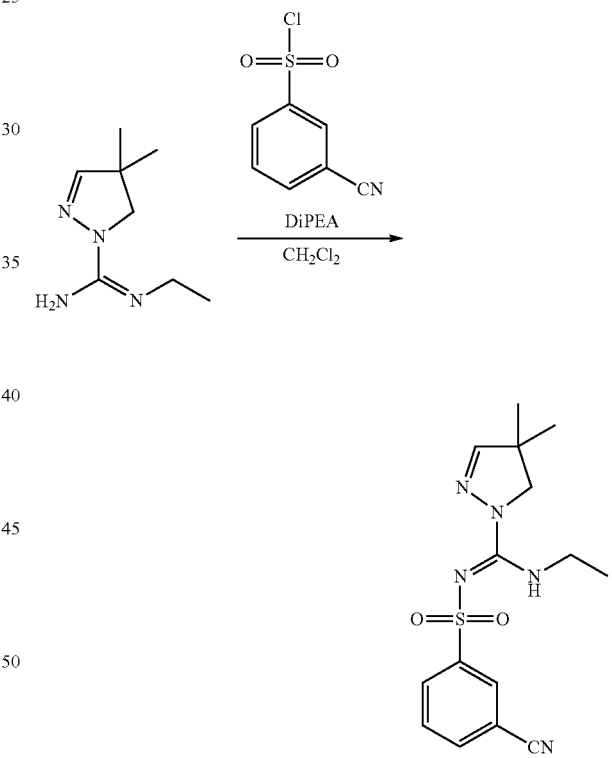

500 mg N-Ethyl-4,4-dimethyl-4,5-dihydro-pyrazole-1-carboxamidine was suspended in 10 mL dichloromethane; 0.92 mL (2.2 equiv.) DiPEA was added and subsequently 0.49 g (1.0 equiv.) 3-cyanobenzenesulfonyl chloride. The mixture was stirred overnight at room temperature. The reaction mixture was extracted with 5% aqueous NaHCO$_3$ and 2 M aqueous NaOH, dried over Na$_2$SO$_4$ and concentrated under reduced pressure to yield 680 mg (82%) of a brown oil. $^1$H NMR (400 MHz, CDCl$_3$) δ 1.18 (t, J=7 Hz, 3H), 1.25 (s, 6H), 3.41-3.52 (m, 2H), 3.81 (s, 2H), 6.71 (br s, 1H), 6.80 (s, 1H), 7.59 (t, J=8 Hz, 1H), 7.73-7.79 (m, 1H), 8.15-8.21 (m, 1H), 8.22-8.26 (m, 1H).

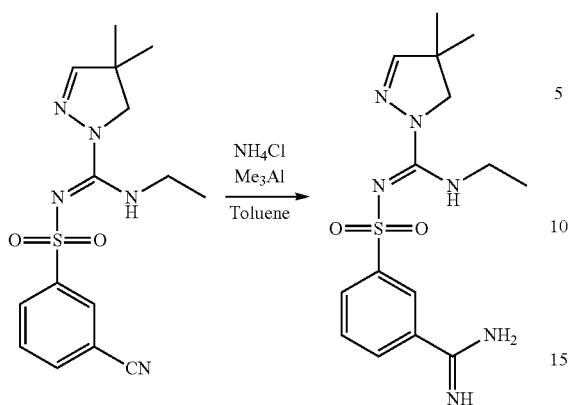
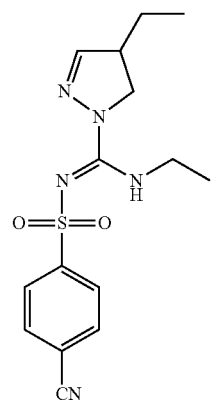

535 mg (10 equiv.) Ammonium chloride was suspended in 10 mL toluene. The mixture was cooled in an ice bath. Dropwise, 5.00 mL of a 2 M solution of trimethylaluminium (10 equiv.) was added, the ice bath was removed and the mixture was stirred at room temperature for 30 minutes. Subsequently, a solution of 340 mg 3-Cyano-N-[(4,4-dimethyl-4,5-dihydro-pyrazol-1-yl)-ethylamino-methylene]-benzenesulfonamide in 5 mL toluene was added dropwise, and the mixture was stirred at 80° C. overnight. After cooling down, the mixture was diluted with chloroform and filtered over Hyflo. The Hyflo was washed with MeOH and the filtrate was purified with SPE (Isolute Flash SCX-2, conditioning, sampling and washing with MeOH, elution with 1 M $NH_3$ in MeOH) to yield 280 mg of a yellow oil after evaporation. This was further purified with flash column chromatography (MeOH/$Et_3N$ 97:3) to yield 210 mg (59%) of an off-white amorph. $^1$H NMR (400 MHz, $CDCl_3$) δ 1.17 (t, J=7 Hz, 3H), 1.23 (s, 6H), 3.41-3.53 (m, 2H), 3.79 (s, 2H), 6.77 (s, 1H), 6.80 (br s, 1H), 7.53 (t, J=8 Hz, 1H), 7.74-7.81 (m, 1H), 8.00-8.07 (m, 1H), 8.15-8.20 (m, 1H).

4-{[Ethylamino-(4-ethyl-4,5-dihydro-pyrazol-1-yl)-methylene]-sulfamoyl}-benzamide (Compound 43)

4-Cyano-N-[ethylamino-(4-ethyl-4,5-dihydro-pyrazol-1-yl)-methylene]-benzenesulfonamide

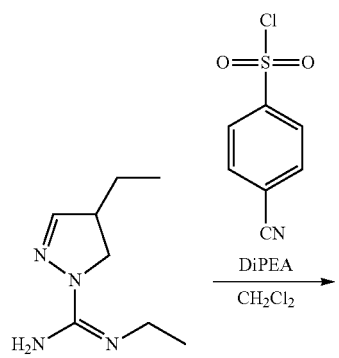

Under $N_2$ atmosphere, 2.50 g 4,N-diethyl-4,5-dihydro-pyrazole-1-carboxamidine was dissolved in 30 mL dry DCM, and 5.69 mL DiPEA and 3.0 g 4-cyanobenzene-1-sulfonylchloride were added. The mixture was stirred overnight at room temperature. The mixture was extracted twice with 5% aqueous $NaHCO_3$, dried over $MgSO_4$ and evaporated to dryness. The residue was purified by flash chromatography (DCM/acetone 97:3) to yield 1.47 g (30%) of a brown oil. $^1$H NMR (400 MHz, $CDCl_3$) δ 0.98 (t, J=7.5 Hz, 3H), 1.16 (t, J=7.2 Hz, 3H), 1.45-1.73 (m, 2H), 3.09-3.24 (m, 1H), 3.38-3.51 (m, 2H), 3.72 (dd, J=11.0, 7.4 Hz, 1H), 4.12 (t, J=11.0 Hz, 2H), 6.74 (br. s., 1H), 6.96 (d, J=1.5 Hz, 1H), 7.75 (d, J=8.1 Hz, 2H), 8.05 (d, J=8.1 Hz, 2H).

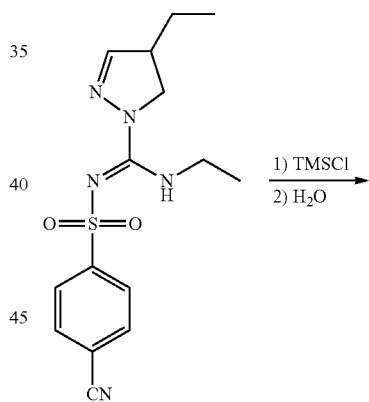

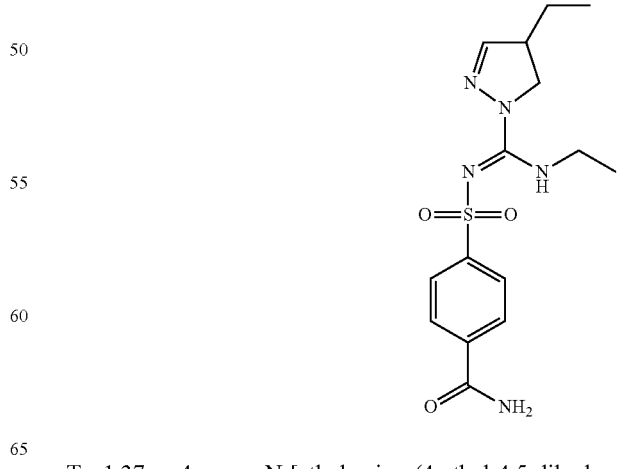

To 1.37 g 4-cyano-N-[ethylamino-(4-ethyl-4,5-dihydro-pyrazol-1-yl)-methylene]-benzenesulfonamide was added 2.08 mL of TMSCl. The mixture was cooled to 0-5° C. and at this temperature 0.3 mL of water was added slowly. The solution was allowed to slowly warm to room temperature (~3 h.) The mixture was basified with solid NaHCO$_3$ and then extracted twice with DCM. The combined organic layers were dried over MgSO$_4$ and evaporated to dryness. The residue was purified by flash chromatography (DCM/MeOH 95:5) to yield 0.79 g (52%) of a yellow oil that solidified upon standing; m.p. 146-149° C. $^1$H NMR (400 MHz, CDCl$_3$) δ 0.97 (t, J=7.5 Hz, 3H), 1.15 (t, J=7.2 Hz, 3H), 1.42-1.79 (m, 2H), 3.07-3.18 (m, 1H), 3.39-3.53 (m, 2H), 3.70 (dd, J=11.3, 7.4 Hz, 1H), 4.09 (t, J=11.3 Hz, 1H), 5.79 (br. s., 1H), 6.34 (br. s., 1H), 6.79 (br. s., 1H), 6.94 (d, J=1.5 Hz, 1H) 7.88 (d, J=8.1 Hz, 2H), 7.98 (d, J=8.1 Hz, 2H).

3-{[Ethylamino-(4-ethyl-4,5-dihydro-pyrazol-1-yl)-methylene]-sulfamoyl}-benzamide (Compound 44)

3-Cyano-N-[ethylamino-(4-ethyl-4,5-dihydro-pyrazol-1-yl)-methylene]-benzenesulfonamide

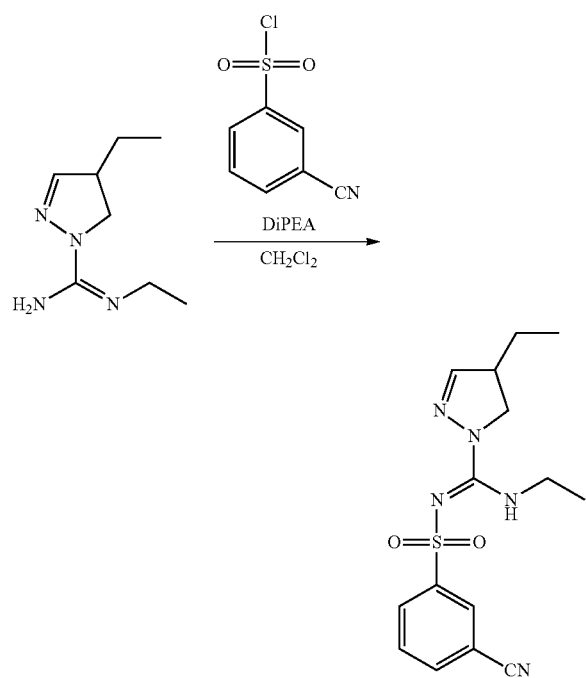

Under N$_2$ atmosphere, 3.0 g 4,N-diethyl-4,5-dihydro-pyrazole-1-carboxamidine was dissolved in 35 mL dry DCM, and 6.83 mL DiPEA and 3.6 g of 3-cyanobenzene-1-sulfonyl-chloride were added. The mixture was stirred overnight at room temperature. The mixture was extracted twice with 5% aqueous NaHCO$_3$, dried over MgSO$_4$ and evaporated to dryness. The residue was purified by flash chromatography (DCM/acetone 98:2) to yield 1.78 g (27%) of a brown oil. $^1$H NMR (400 MHz, CDCl$_3$) δ 0.98 (t, J=7.5 Hz, 3H), 1.17 (t, J=7.2 Hz, 3H), 1.43-1.76 (m, 2H), 3.08-3.27 (m, 1H), 3.40-3.54 (m, 2H), 3.73 (dd, J=11.3, 7.4 Hz, 1H), 4.13 (t, J=11.3 Hz, 1H), 6.74 (br. s., 1H), 6.96 (d, J=1.2 Hz, 1H), 7.59 (t, J=8.1 Hz, 1H), 7.75 (d, J=8.1 Hz, 1H), 8.18 (d, J=8.1 Hz, 1H), 8.23 (m, 1H).

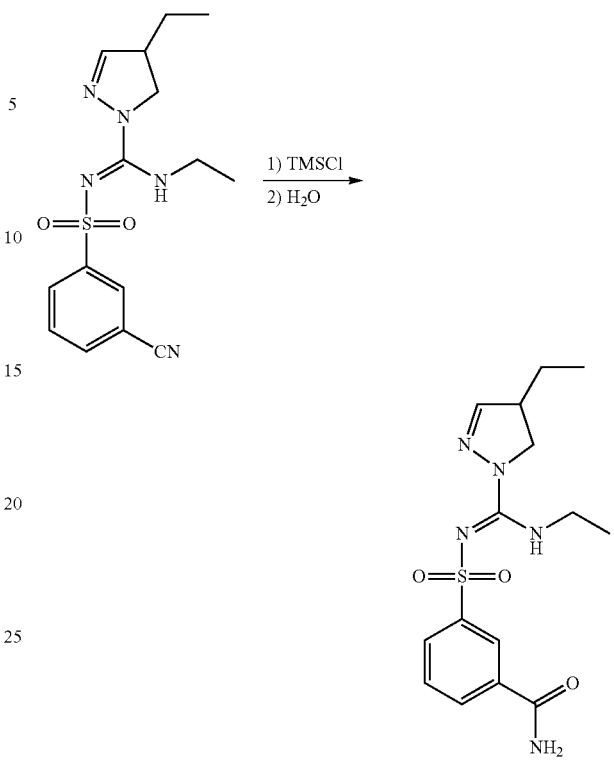

To 1.78 g 3-cyano-N-[ethylamino-(4-ethyl-4,5-dihydro-pyrazol-1-yl)-methylene]-benzenesulfonamide was added 4.86 mL of TMSCl. The mixture was cooled to 0-5° C. and at this temperature 0.35 mL of water was added slowly. The solution was allowed to slowly warm to room temperature (~3 h.) The mixture was basified with solid NaHCO$_3$ and then extracted twice with DCM. The combined organic layers were dried over MgSO$_4$ and evaporated to dryness. The residue was purified by flash chromatography (DCM/MeOH/Acetic acid 96:3.75:0.25 to yield 1.39 g (74%) of an off-white powder; m.p. 164-168° C. $^1$H NMR (400 MHz, DMSO-d$_6$) δ 0.96 (t, J=7.4 Hz, 3H), 1.11 (t, J=7.2 Hz, 3H), 1.44-1.71 (m, 2H), 3.06-3.24 (m, 1H), 3.39-3.49 (m, 2H), 3.66 (dd, J=11.3, 7.4 Hz, 1H), 4.05 (t, J=11.3 Hz, 1H), 6.58 (br. s., 1H), 7.01 (d, J=1.5 Hz, 1H), 7.07 (br. s., 1H), 7.54 (t, J=7.8 Hz, 1H), 7.86 (br. s., 1H), 8.02 (d, J=7.8 Hz, 1H), 8.06 (d, J=7.8 Hz, 1H), 8.47 (m, 1H).

4-{[Ethylamino-(4-ethyl-4,5-dihydro-pyrazol-1-yl)-methylene]-sulfamoyl}-benzoic acid (Compound 45)

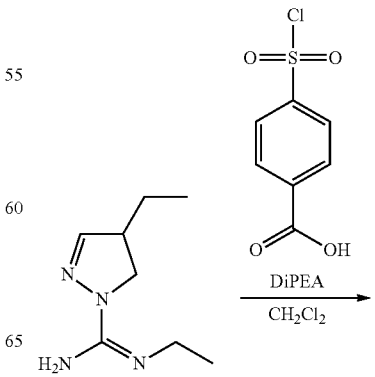

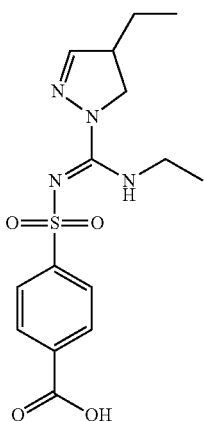

Under N₂ atmosphere, 2.27 g 4,N-diethyl-4,5-dihydro-pyrazole-1-carboxamidine was dissolved in 30 mL dry DCM, and 5.17 ml DiPEA and 2.98 g of 4-(chlorosulfonyl)benzoic acid were added. The mixture was stirred overnight at room temperature and evaporated to dryness. The residue was purified by flash chromatography (first column with DCM/MeOH/NH₄OH 92:7.5:0.5; second column with DCM/MeOH/Acetic acid 92:7.5:0.5) to yield 0.26 g (4%) of product (mono-DiPEA salt) as an off-white amorphous powder. ¹H NMR (400 MHz, CDCl₃) δ 0.98 (t, J=7.4 Hz, 3H), 1.27 (t, J=7.2 Hz, 3H), 1.53-1.81 (m, 2H), 3.15-3.30 (broad peak, 1H), 3.43-3.66 (broad peak, 3H), 4.01-4.20 (broad peak, 1H), 6.97 (br. s., 1H), 7.90 (d, J=8.1 Hz, 2H), 8.14 (d, J=8.1 Hz, 2H), 9.69 (br. s., 1H).

3-{[Ethylamino-(4-ethyl-4,5-dihydro-pyrazol-1-yl)-methylene]-sulfamoyl}-benzoic acid (Compound 46)

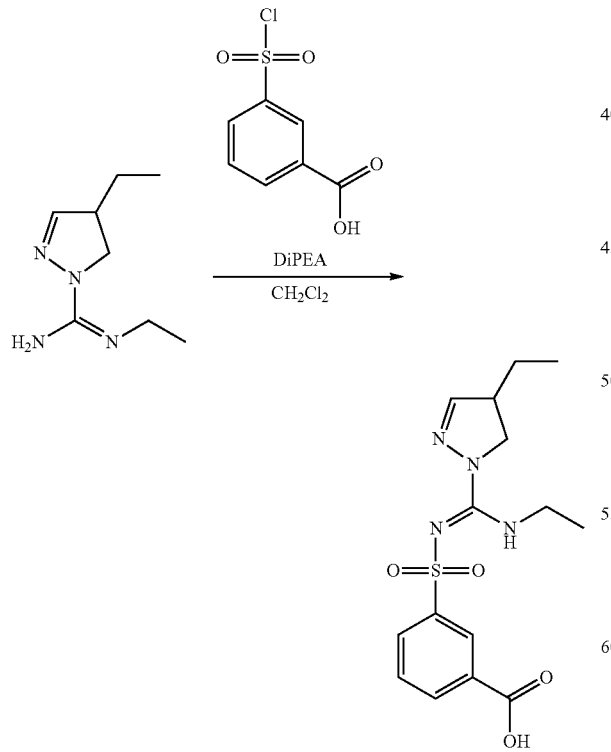

Under N₂ atmosphere, 1.0 g 4,N-diethyl-4,5-dihydro-pyrazole-1-carboxamidine was dissolved in 15 mL dry DCM, and 1.14 mL DiPEA and 1.31 g of 3-(chlorosulfonyl)benzoic acid were added. The mixture was stirred overnight at room temperature and evaporated to dryness. The residue was purified by flash chromatography (first column with DCM/MeOH/acetic acid 84:15:1; second column with DCM/MeOH/NH₄OH 84:15:1) to yield 0.08 g (4%) of an off-white powder. ¹H NMR (400 MHz, CDCl₃) δ 0.90 (t, J=7.4 Hz, 3H), 1.14 (t, J=7.2 Hz, 3H), 1.38-1.62 (m, 2H), 3.02-3.18 (m, 1H), 3.27-3.62 (m, 3H), 3.89-4.17 (m, 1H), 6.94 (s, 1H), 7.26 (t, J=7.8 Hz, 1H), 7.89 (d, J=7.8 Hz, 1H), 8.05 (d, J=7.8 Hz, 1H), 8.49 (s, 1H).

3-Aminomethyl-N-[(2,3-diaza-spiro[4.4]non-3-en-2-yl)-ethylamino-methylene]-benzenesulfonamide (Compound 61)

3-Cyano-N-[(2,3-diaza-spiro[4.4]non-3-en-2-yl)-ethylamino-methylene]-benzenesulfonamide

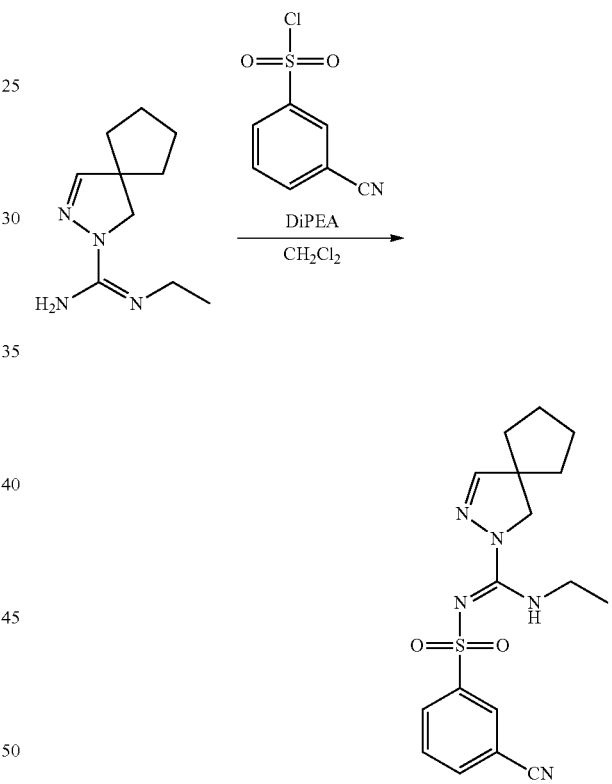

To a solution of 3.50 g 3-cyanobenzenesulfonyl chloride in 150 mL DCM were added 17.69 mL (6.0 equiv.) DiPEA and 4.00 g (1.0 equiv.) N-ethyl-2,3-diaza-spiro[4.4]non-3-ene-2-carboxamidine. The reaction mixture was stirred overnight at room temperature and extracted with water. The organic phase was dried over Na₂SO₄ and evaporated, and the residue was purified by automated flash chromatography (EtOAc/PA 1:1) to give 3.54 g (57%) of a pale yellow oil. ¹H NMR (400 MHz, CDCl₃) δ 1.17 (t, J=8 Hz, 3H), 1.65-1.86 (m, 8H), 3.41-3.50 (m, 2H), 3.87 (br.s., 2H), 6.70-6.80 (br.s., 1H), 6.87 (s, 1H), 7.60 (t, J=8 Hz, 1H), 7.77 (d, J=8 Hz, 1H), 8.17 (d, J=8 Hz, 1H), 8.23 (br.s., 1H).

3-Aminomethyl-N-[(2,3-diaza-spiro[4.4]non-2-yl)-ethylamino-methylene]-benzenesulfonamide

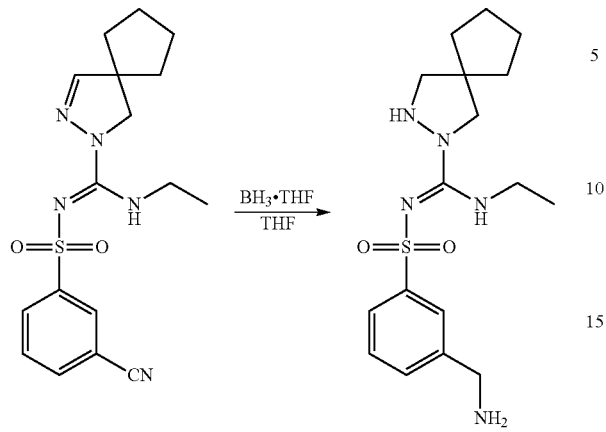

3.54 g 3-cyano-N-[(2,3-diaza-spiro[4.4]non-3-en-2-yl)-ethylamino-methylene]-benzenesulfonamide was dissolved in 50 mL THF, and 49.24 mL of a 1 M solution of borane-THF complex was added dropwise. The mixture was stirred for 1 hour at 30° C., quenched with 3 M aqueous HCl (3.6 equiv.) and stirred for another hour. The reaction mixture was cooled in an ice bath, basified with aqueous NaOH (7 equiv.) and extracted with DCM. The organic phase was dried over $Na_2SO_4$ and evaporated, and the residue was purified by automated flash chromatography (DCM/MeOH/$NH_4OH$ 92:7.5: 0.5) to give 0.80 g (22%) of a yellow oil. $^1$H NMR (400 MHz, $CDCl_3$) δ 1.13 (t, J=8 Hz, 3H), 1.50-1.76 (m, 8H), 2.76 (m, 2H), 3.17-3.27 (m, 2H), 3.78 (s, 2H), 3.91 (s, 2H), 4.40-4.50 (br.m., 1H), 6.88 (br.t., J=6 Hz, 1H), 7.37-7.44 (m, 2H), 7.78-7.83 (m, 1H), 7.88 (br.s., 1H).

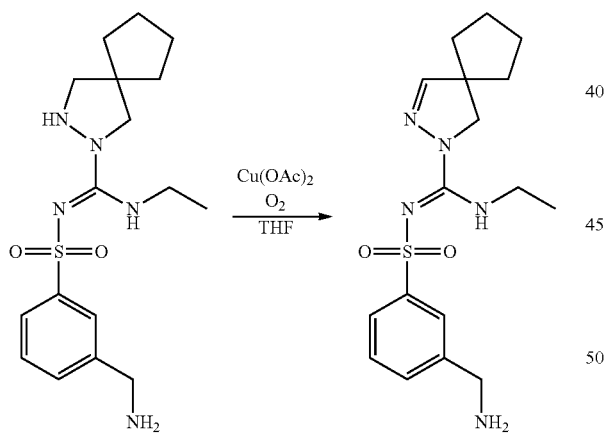

0.1 g 3-Aminomethyl-N-[(2,3-diaza-spiro[4.4]non-2-yl)-ethylamino-methylene]-benzenesulfonamide was dissolved in 10 mL THF, and 0.5 mg copper(II)acetate was added. Over a period of 20 seconds, $O_2$ was bubbled through the stirred solution at room temperature, and stirring was continued for 10 minutes. The mixture was concentrated under reduced pressure, and the residue was purified by automated flash chromatography (DCM/MeOH/$NH_4OH$ 92:7.5:0.5) to give 50 mg (50%) of a pale yellow oil. $^1$H NMR (400 MHz, $CDCl_3$) δ 1.15 (t, J=8 Hz, 3H), 1.52-1.84 (br.m., 10H), 3.43-3.53 (m, 2H), 3.84 (br.s., 2H), 3.94 (s, 2H), 6.81 (s, 1H), 6.90 (br.s., 1H), 7.42 (t, J=8 Hz, 1H), 7.47 (d, J=8 Hz, 1H), 7.80 (d, J=8 Hz, 1H), 7.87 (s, 1H).

N-[(2,3-Diaza-spiro[4.4]non-3-en-2-yl)-ethylamino-methylene]-3-hydroxymethyl-benzenesulfonamide (Compound 62)

3-{[(2,3-Diaza-spiro[4.4]non-3-en-2-yl)-ethylamino-methylene]-sulfamoyl}-benzoic acid methyl ester

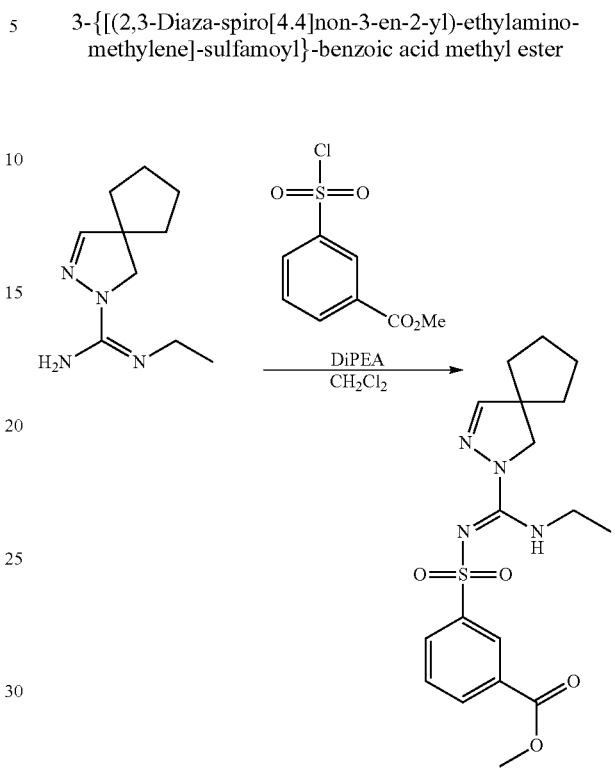

To a solution of 4.07 g 3-chlorosulfonyl-benzoic acid methyl ester in 150 mL DCM were added 17.69 mL (6.0 equiv.) DiPEA and 4.00 g (1.0 equiv.) N-ethyl-2,3-diaza-spiro[4.4]non-3-ene-2-carboxamidine. The reaction mixture was stirred overnight at room temperature under $N_2$ atmosphere, and extracted with water. The organic phase was dried over $Na_2SO_4$ and evaporated, and the residue was purified by automated flash chromatography (EtOAc/PA 1:1) to give 4.80 g (71%) of a yellow solid. $^1$H NMR (400 MHz, $CDCl_3$) δ 1.16 (t, J=8 Hz, 3H), 1.62-1.86 (m, 8H), 3.42-3.53 (m, 2H), 3.87 (s, 2H), 3.95 (s, 3H), 6.83 (s, 1H), 6.83-6.95 (broad peak, 1H), 7.56 (t, J=8 Hz, 1H), 8.13-8.18 (m, 2H), 8.61 (s, 1H).

N-[(2,3-Diaza-spiro[4.4]non-2-yl)-ethylamino-methylene]-3-hydroxymethyl-benzenesulfonamide

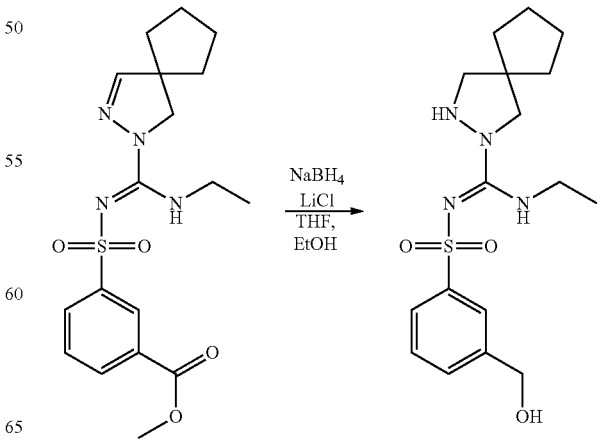

To a solution of 0.50 g 3-{[(2,3-Diaza-spiro[4.4]non-3-en-2-yl)-ethylamino-methylene]-sulfamoyl}-benzoic acid methyl ester in 3.0 mL dry THF were added 0.11 g (2.0 equiv.) dry LiCl and subsequently 0.10 g (2.0 equiv.) NaBH$_4$, followed by addition of 5.0 mL EtOH. The mixture was stirred overnight at room temperature under N$_2$ atmosphere, cooled in an ice bath, and acidified to pH 4.0 by addition of 10% aqueous citric acid. The mixture was concentrated, the residue was dissolved in 6 mL water, and the aqueous phase was extracted 3 times with DCM. The combined organic phases were washed with saturated aqueous NaHCO$_3$, dried over Na$_2$SO$_4$ and evaporated on silica. Purifixation by automated flash chromatography (DCM/MeOH/NH$_4$OH 96:3.75:0.25) gave 0.24 g (51%) of a white solid, m.p. 142-144° C. $^1$H NMR (400 MHz, DMSO-d$_6$) δ 0.93 (t, J=8 Hz, 3H), 1.50-1.69 (m, 8H), 2.72 (d, J=8 Hz, 2H), 3.07-3.16 (m, 2H), 3.50 (s, 2H), 4.56 (d, J=8 Hz, 2H), 5.30 (t, J=6 Hz, 1H), 5.76 (t, J=8 Hz, 1H), 7.39 (d, J=4 Hz, 2H), 7.53-7.65 (m, 2H), 7.76 (s, 1H).

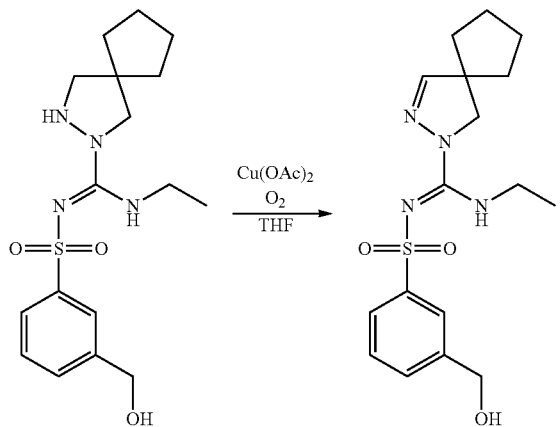 [SMILES: CCN/C(=N\S(=O)(=O)c1cccc(CO)c1)N1CC2(CCCC2)CN1 ; CCN/C(=N\S(=O)(=O)c1cccc(CO)c1)N1CC2(C=N1)CCCC2 ; "Cu(OAc)2O2" ; "THF"]

0.1 g N-[(2,3-Diaza-spiro[4.4]non-2-yl)-ethylamino-methylene]-3-hydroxymethyl-benzenesulfonamide was dissolved in 10 mL THF, and 0.1 mg copper(II)acetate was added. Over a period of 5 seconds, O$_2$ was bubbled through the stirred solution at room temperature, and stirring was continued for 10 minutes. The mixture was concentrated under reduced pressure, and the residue was purified by automated flash chromatography (DCM/MeOH 99:1) to give 80 mg (80%) of a colorless oil. $^1$H NMR (400 MHz, CDCl$_3$) δ 1.13 (t, J=8 Hz, 3H), 1.60-1.83 (m, 8H), 2.58 (br.s., 1H), 3.41-3.51 (m, 2H), 3.82 (br.s., 2H), 4.73 (br.s., 2H), 6.81 (s, 1H), 6.80-7.00 (br.s., 1H), 7.42 (t, J=8 Hz, 1H), 7.49 (d, J=8 Hz, 1H), 7.83 (d, J=8 Hz, 1H), 7.92 (s, 1H).

1H-Indazole-5-sulfonic acid (2,3-diaza-spiro[4.4]non-3-en-2-yl)-ethylamino-methyleneamide (Compound 63)

2,2,2-Trifluoro-N-o-tolyl-acetamide

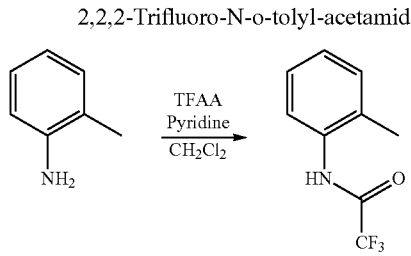

A solution of 48.75 mL o-toluidine and 45.90 mL (1.25 equiv.) dry pyridine in 600 mL DCM was cooled to −5-0° C. in an ice/aceton bath, and 69.46 mL (1.10 equiv.) trifluoroacetic anhydride was added dropwise over a period of 1 hour, keeping the reaction mixture temperature below 5° C. The ice-bath was removed, the mixture was stirred at room temperature overnight, subsequently poured into 2 L of water and extracted three times with DCM. The combined organic layers were washed with 500 ml 0.5N HCl, water and brine, then dried over Na$_2$SO$_4$, filtered and evaporated to give 90.3 g (97%) of a pale yellow solid which was used without purification in the next reaction. $^1$H NMR (400 MHz, CDCl$_3$) δ 2.28 (s, 3H), 7.15-7.31 (m, 3H), 7.73 (d, J=7.83 Hz, 1H), 7.79 (br.s., 1H).

3-Methyl-4-(2,2,2-trifluoro-acetylamino)-benzenesulfonyl chloride

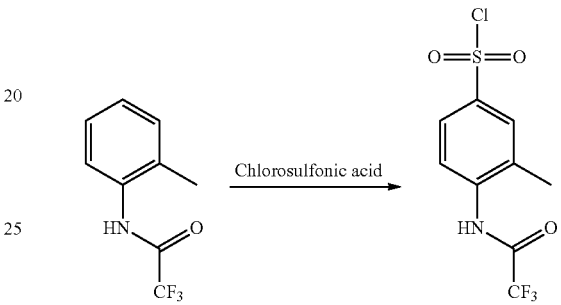

16.43 mL (5.00 equiv.) Chlorosulfonic acid was cooled in an aceton/ice-bath and 10.00 g 2,2,2-trifluoro-N-o-tolyl-acetamide was added in three portions, keeping the reaction mixture temperature below 5° C. The ice-bath was removed, the pale yellow mixture was allowed to warm to room temperature and then heated on an oil bath of 70° C. for 5.5 hours. The oil bath was removed and at about 30-35° C. the brown mixture was poured very carefully into a beaker with ice (exotermic, copious amounts of HCl evolve), giving a thick, gummy and very sticky precipitate. The mixture was extracted three times with DCM and the combined organic layers were washed with brine, dried over Na$_2$SO$_4$, filtered and evaporated onto silica. Purification with flash chromatography (EtOAc/PA 1:9→1:4) yielded 10.3 g (69%) of a white solid. $^1$H NMR (400 MHz, CDCl$_3$) δ 2.46 (s, 3H), 7.90 (br.s., 1H), 7.94 (s, 1H), 7.98 (dd, J=8.6, 2.15 Hz, 1H), 8.35 (d, J=8.6 Hz, 1H).

N-(4-{[(2,3-Diaza-spiro[4.4]non-3-en-2-yl)-ethylamino-methylene]-sulfamoyl}-2-methyl-phenyl)-2,2,2-trifluoro-acetamide

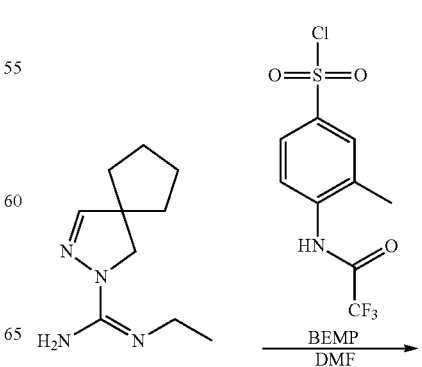

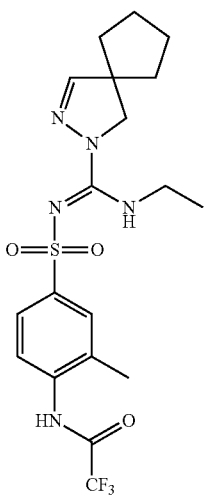

To a solution of 0.23 g N-ethyl-2,3-diaza-spiro[4.4]non-3-ene-2-carboxamidine in 5 mL dry DMF was added 0.87 mL (3.0 equiv.) BEMP and the light brown mixture was stirred for 10 minutes at room temperature. Subsequently, 0.33 g (1.1 equiv.) 3-methyl-4-(2,2,2-trifluoro-acetylamino)-benzenesulfonyl chloride was added in one portion and the resulting bright yellow solution was stirred overnight at room temperature. The mixture was cooled in an ice bath, acidified with 1 N HCl, and then extracted three times with EtOAc/Et$_2$O 1:1. The combined organic layers were washed once with water, then with brine, dried over Na$_2$SO$_4$ and evaporated onto silica. Purification with flash chromatography (EtOAc/PA 4:6→5:5) yielded 0.18 g (39%) of a white solid. $^1$H NMR (400 MHz, CDCl$_3$) δ 1.16 (t, J=7.2 Hz, 3H), 1.63-1.86 (m, 8H), 2.33 (s, 3H), 3.43-3.52 (m, 2H), 3.83 (s, 2H), 6.77-6.85 (br.s., 1H), 6.83 (s, 1H), 7.73-7.79 (m, 2H), 7.86 (d, J=8.3 Hz, 1H), 8.10 (br.s., 1H).

4-Amino-N-[(2,3-diaza-spiro[4.4]non-2-yl)-ethylamino-methylene]-3-methyl-benzenesulfonamide

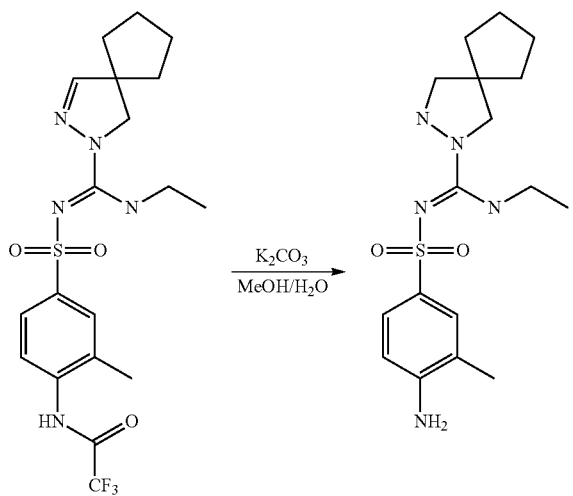

0.36 g N-(4-{[(2,3-Diaza-spiro[4.4]non-3-en-2-yl)-ethylamino-methylene]-sulfamoyl}-2-methyl-phenyl)-2,2,2-trifluoro-acetamide was added to 15.00 mL MeOH and the mixture was stirred until all the solids were dissolved (~5-10 min). Then 2.00 mL water and 0.54 g (5.0 equiv.) K$_2$CO$_3$ were added, and the resulting suspension was refluxed for 4.5 hours. The mixture was allowed to cool, concentrated under reduced pressure, taken up in DCM/H$_2$O and extracted three times with DCM. The combined organic layers were washed with brine, dried over Na$_2$SO$_4$, filtered and evaporated onto silica. Purification using flash chromatography (EtOAc/PA 1:1→3:1) yielded 0.16 g (56%) of a pale yellow oil. $^1$H NMR (400 MHz, CDCl$_3$) δ 1.15 (t, J=7.33 Hz, 3H), 1.57-1.82 (m, 8H), 2.18 (s, 3H), 3.42-3.53 (m, 2H), 3.79 (s, 2H), 3.92 (br.s., 2H) 6.65 (d, J=8.0 Hz, 1H), 6.77 (s, 1H), 6.94 (br.s., 1H), 7.58 (dd, J=8.0, 2.0 Hz, 1H), 7.62 (d, J=2.0 Hz, 1H).

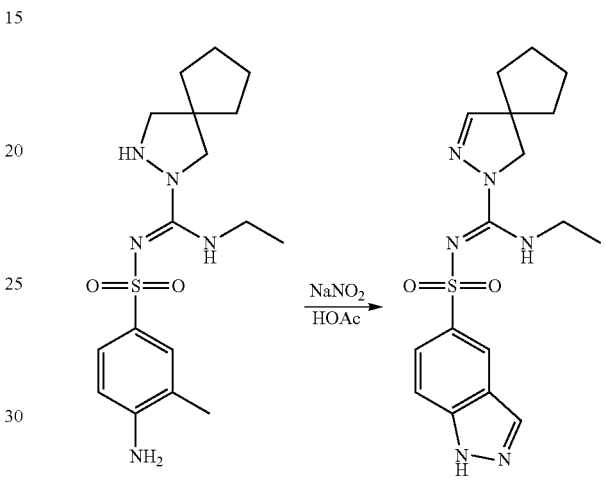

0.16 g 4-Amino-N-[(2,3-diaza-spiro[4.4]non-2-yl)-ethylamino-methylene]-3-methyl-benzenesulfonamide was dissolved in 2.50 mL acetic acid, and a solution of 30.37 mg (1.0 equiv.) sodium nitrite in 0.2 mL water was added in one portion. The resulting yellow/orange mixture was stirred for 3 hours at room temperature, poured into a 5% NaHCO$_3$-solution (excessive foaming occurs) and extracted three times with EtOAc. The combined organic layers were washed once with brine, dried over Na$_2$SO$_4$, filtered and evaporated onto silica. Purification with flash chromatography (DCM/MeOH 97:3) yielded 10 mg (6%) of a yellow oil. $^1$H NMR (400 MHz, CDCl$_3$) δ 1.15 (t, J=7.0 Hz, 3H), 1.59-1.82 (m, 8H), 3.41-3.53 (m, 2H), 3.83 (br.s., 2H), 6.80 (s, 1H), 6.90 (br.s., 1H), 7.58 (d, J=8.8 Hz, 1H), 7.94 (dd, J=8.8, 1.52 Hz, 1H), 8.17 (s, 1H), 8.40 (s, 1H).

2-Trifluoromethyl-1H-indole-5-sulfonic acid (4,4-dimethyl-4,5-dihydro-pyrazol-1-yl)-ethylamino-methyleneamide (Compound 64)

N-(2-Bromo-phenyl)-2,2,2-trifluoro-acetamide

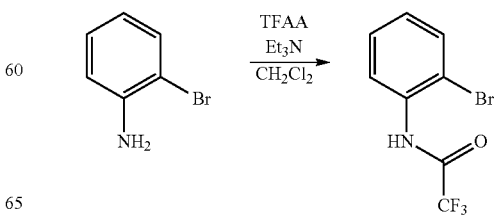

24.9 g 2-Bromoaniline was dissolved in 200 mL DCM. 28.0 mL (1.4 equiv.) triethylamine was added and the reaction mixture was cooled to 0° C. Then, 24.0 mL (1.2 equiv.) trifluoroacetic anhydride was added dropwise, keeping the temperature of the reaction mixture below 10° C.). The mixture was allowed to warm to room temperature, stirred for 2 hours and quenched with water. The organic layer was separated, dried over $Na_2SO_4$, filtered and evaporated under reduced pressure. Purification by flash chromatography ($Et_2O$/PA 1:6) afforded 34.6 g (89%) of a white crystalline compound. $^1H$ NMR (400 MHz, $CDCl_3$) δ 7.12 (dt, J=7.8, 1.3 Hz, 1H), 7.39 (dt, J=7.8, 1.3 Hz, 1H), 7.61 (dd, J=8.0, 1.3 Hz, 1H), 8.31 (dd, J=8.0, 1.3 Hz, 1H), 8.45 (br.s., 1H).

3-Bromo-4-(2,2,2-trifluoro-acetylamino)-benzene-sulfonyl chloride

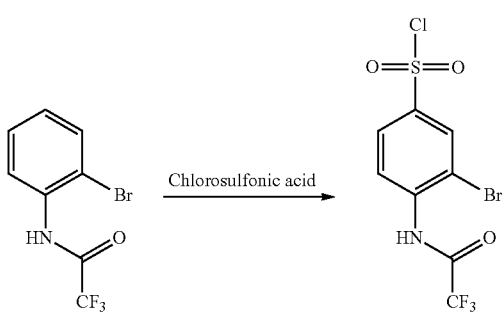 [SMILES: O=C(Nc1ccccc1Br)C(F)(F)F ; O=C(Nc1ccc(S(=O)(=O)Cl)cc1Br)C(F)(F)F]

3.0 g N-(2-Bromo-phenyl)-2,2,2-trifluoro-acetamide was added in three portions to 3.74 mL (5.0 equiv.) chlorosulfonic acid under cooling in an ice-bath. The ice-bath was removed, the mixture was warmed to room temperature, and subsequently stirred for 1 hour at 80° C. After cooling, the clear brown reaction mixture was poured into ice and extracted with DCM. The organic phase was dried over $Na_2SO_4$, filtered, and evaporated to dryness to give 3.36 g (80%) of an oil that solidified upon standing. $^1H$ NMR (400 MHz, $CDCl_3$) δ 8.09 (dd, J=9.0, 2.0 Hz, 1H), 8.30 (d, J=2.0 Hz, 1H), 8.69 (d, J=9.0 Hz, 1H), 8.71 (br.s., 1H).

N-(2-Bromo-4-{[(4,4-dimethyl-4,5-dihydro-pyrazol-1-yl)-ethylamino-methylene]-sulfamoyl}-phenyl)-2,2,2-trifluoro-acetamide

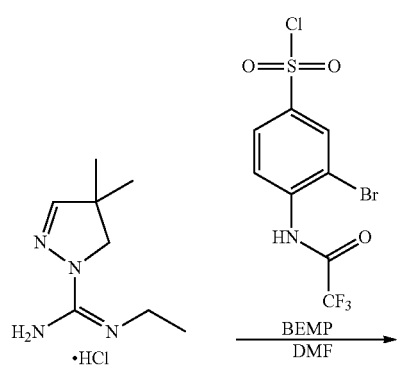

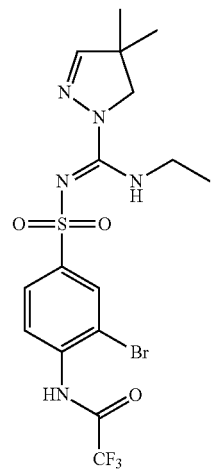

To a solution of 1.20 g N-ethyl-4,4-dimethyl-4,5-dihydro-pyrazole-1-carboxamidine hydrochloride in 35 mL dry THF was added 5.1 mL (3.0 equiv.) BEMP and the reaction mixture was stirred for 10 minutes at room temperature. 2.15 g (1.0 equiv.) 3-Bromo-4-(2,2,2-trifluoro-acetylamino)-benzenesulfonyl chloride was added in one portion and the resulting bright yellow solution was stirred overnight at room temperature. The reaction mixture was acidified with 1N HCl and extracted twice with EA. The combined organic layers were dried over $Na_2SO_4$, filtered and evaporated under reduced pressure. Purification by flash chromatography ($Et_2O$/PA 1:1→$Et_2O$) afforded 2.29 g (78%) of product. $^1H$ NMR (400 MHz, $CDCl_3$) δ 1.18 (t, J=7.3 Hz, 3H), 1.24 (s, 6H), 3.43-3.51 (m, 2H), 3.79 (br.s, 2H), 6.78 (s, 1H), 7.93 (dd, J=8.6, 2.0 Hz, 1H), 8.19 (d, J=2.0 Hz, 1H), 8.39 (d, J=8.6 Hz, 1H), 8.61 (br.s., 1H).

4-Amino-3-bromo-N-[(4,4-dimethyl-pyrazolidin-1-yl)-ethylamino-methylene]-benzenesulfonamide

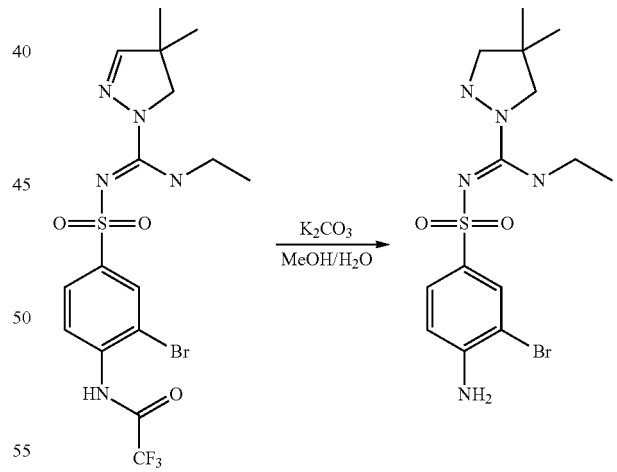

2.18 g N-(2-Bromo-4-{[(4,4-dimethyl-4,5-dihydro-pyrazol-1-yl)-ethylamino-methylene]-sulfamoyl}-phenyl)-2,2,2-trifluoro-acetamide was dissolved in 75 mL MeOH. 3.0 g (5.0 equiv.) Potassium carbonate and 10 mL water were added and the reaction mixture was refluxed for 2.5 hours. Volatiles were removed under reduced pressure, and the residue was taken up in EA and extracted with 2N aqueous NaOH. The organic layer was dried over $Na_2SO_4$, filtered and concentrated on silica. Purification by flash chromatography ($Et_2O$) afforded 1.54 g (83%) of product. $^1H$ NMR (400 MHz, $CDCl_3$) δ 1.17 (t, J=7.3 Hz, 3H), 1.19-1.23 (m, 6H), 3.43-3.52 (m, 2H), 3.74

(br.s, 2H), 4.45 (br.s, 2H), 6.73 (s, 1H), 6.75 (d, J=8.4 Hz, 1H), 6.88 (br.s., 1H), 7.65 (dd, J=8.4, 2.0 Hz, 1H) 7.99 (d, J=2.0 Hz, 1H).

To a Pyrex-glass test tube with a screw stopper equipped with a magnetic stirring bar, containing 22 mg (0.10 equiv.) palladium(II) acetate, 71.5 mg (0.15 equiv.) X-Phos (71.5 mg; 0.15 eq.) and 0.39 g (1.2 euiv.) cesium carbonate, was added 2.0 mL degassed toluene. After the addition of 0.42 g 4-amino-3-bromo-N-[(4,4-dimethyl-pyrazolidin-1-yl)-ethylamino-methylene]-benzenesulfonamide and 0.21 g (1.2 equiv.) 2-bromo-3,3,3-trifluoropropene, the closed reactor was heated for 15 hours at 125° C. The mixture was taken up in EA and extracted with 5% aqueous $NaHCO_3$. The organic layer was dried over $Na_2SO_4$, filtered and concentrated. Purification by thick layer chromatography on silicagel plates ($Et_2O$) afforded 10 mg (1.6%) of product. HR-MS: $[M+H]^+$ 416.1346 (calculated for $C_{17}H_{21}F_3N_5O_2S$: 416.1368). $^1H$ NMR (400 MHz, $CDCl_3$) δ 1.15 (t, J=7.3 Hz, 3H), 1.21 (br.s., 6H), 3.43-3.51 (m, 2H), 3.76 (br.s., 2H), 5.83 (br.s., 1H), 6.73 (s, 1H), 7.01 (s, 1H), 7.50 (d, J=8.7 Hz, 1H), 7.88 (dd, J=8.7, 1.5 Hz, 1H), 8.31 (br.s, 1H), 9.39 (br.s., 1H).

Compounds Prepared by the Same Synthetic Route are Marked 'Route 2' in the Table Below.

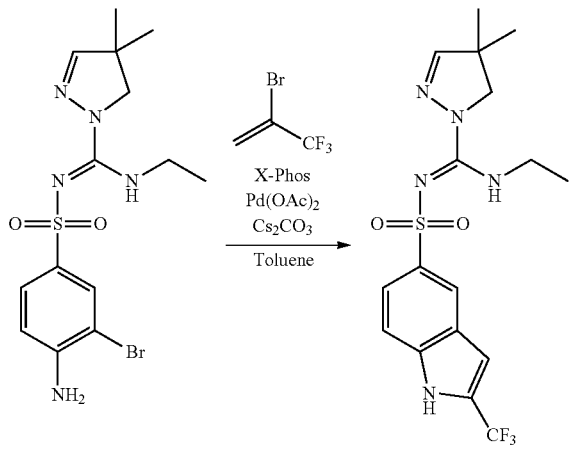

| Comp | structure | S* | Physico-chemical prop. | | | pharmacology 5-HT$_6$ | |
|---|---|---|---|---|---|---|---|
| | | | TLC R$_f$(X) | LCMS R$_t$ | m.p. ° C. | pA$_2$ | pK$_i$ |
| 1 (+)-enantiomer +130° (1%, CHCl$_3$) | | 2 | 0.20 (A) | 1.66 | | 8.7 | 8.5 |
| 2 (−)-enantiomer −136° (1%, CHCl$_3$) | | 2 | 0.20 (a) | 1.66 | | 8.2 | 8.0 |
| 3 | | 2 | 0.08 (b) | 1.35 | | 7.6 | 7.9 |
| 4 | | 1 | 0.28 (a) | 1.55 | 141-142 | 8.3 | 8.0 |
| 5 | | 1 | 0.28 (a) | 1.45 | | 7.1 | 7.0 |

-continued

| Comp | structure | S* | TLC R_f(X) | LCMS R_t | m.p. °C. | 5-HT_6 pA_2 | pK_i |
|---|---|---|---|---|---|---|---|
| 6 | | 1 | | | 148-150 | | |
| 7 | | 1 | 0.19 (c) | | | 7.6 | 7.2 |
| 8 | | 1 | 0.17 (c) | | | 6.8 | 6.7 |
| 9 | | 1 | 0.16 (c) | | | 6.7 | 6.6 |
| 10 | | 1 | | 1.58 | | | |
| 11 (+)-enantiomer +131° (1%, CHCl_3) | | 2 | 1.31 (a) | 1.43 | | 9.3 | 9.0 |
| 12 (−)-enantiomer −131° (1%, CHCl_3) | | 2 | 0.31 (a) | 1.43 | | 9.0 | 8.8 |

-continued

| Comp | structure | S* | TLC $R_f(X)$ | LCMS $R_t$ | m.p. °C. | 5-HT$_6$ pA$_2$ | pK$_i$ |
|---|---|---|---|---|---|---|---|
| 13 | | 2 | 0.13 (b) | 1.52 | | 8.5 | 8.2 |
| 14 | | 1 | 0.22 (a) | 1.82 | | 9.0 | 8.8 |
| 15 | | 1 | | 1.71 | | | |
| 16 | | 2 | | 1.38 | | 8.0 | 7.9 |
| 17 | | 1 | | 1.61 | | | |
| 18 | | 2 | | 1.62 | | | 8.4 |
| 19 | | 2 | 0.35 (d) | 1.34 | | 8.6 | 8.5 |
| 20 (+)-enantiomer +120° (1%, MeOH) | | 2 | 0.35 (d) | | | 9.0 | 8.7 |

| Comp | structure | S* | TLC $R_f(X)$ | LCMS $R_t$ | m.p. °C. | 5-HT$_6$ pA$_2$ | pK$_i$ |
|---|---|---|---|---|---|---|---|
| 21 (−)-enantiomer −104° (1%, MeOH) | | 2 | 0.35 (d) | | | 8.2 | 8.0 |
| 22 | | 2 | | 1.47 | | 8.3 | 7.9 |
| 23 | | 1 | | 1.59 | | | |
| 24 | | 1 | | | 140-142 | | |
| 25 | | 1 | | 1.60 | 158-160 | | |
| 26 | | 2 | | 1.61 | | 7.7 | 8.0 |
| 27 | | 2 | | 1.61 | | 7.6 | 7.8 |
| 28 | | 1 | 0.32 (e) | | | | |

-continued
| Comp | structure | S* | TLC R_f(X) | LCMS R_t | m.p. °C. | 5-HT_6 pA_2 | pK_i |
|---|---|---|---|---|---|---|---|
| 29 | 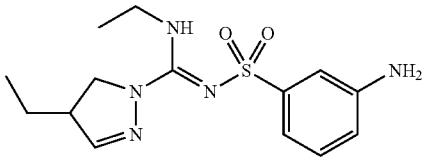 [SMILES: CCN/C(=N\S(=O)(=O)c1cccc(N)c1)N1CC(CC)C=N1] | 2 | | 1.36 | | 7.0 | 7.2 |
| 30 | 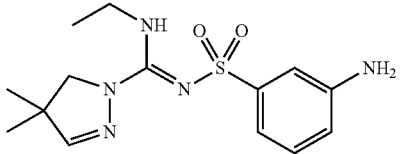 [SMILES: CCN/C(=N\S(=O)(=O)c1cccc(N)c1)N1CC(C)(C)C=N1] | 2 | | 1.31 | | 6.9 | 6.6 |
| 31 | 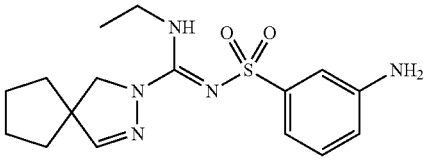 [SMILES: CCN/C(=N\S(=O)(=O)c1cccc(N)c1)N1CC2(C=N1)CCCC2] | 2 | | 1.54 | | | |
| 32 | 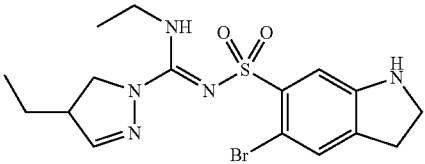 [SMILES: CCN/C(=N\S(=O)(=O)c1cc2c(cc1Br)CCN2)N1CC(CC)C=N1] | 2 | | 1.62 | | | |
| 33 | 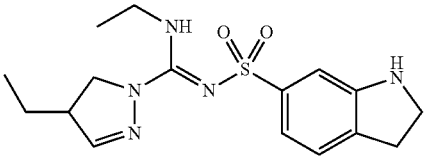 [SMILES: CCN/C(=N\S(=O)(=O)c1ccc2c(c1)NCC2)N1CC(CC)C=N1] | 2 | | 1.22 | | | 6.3 |
| 34 | 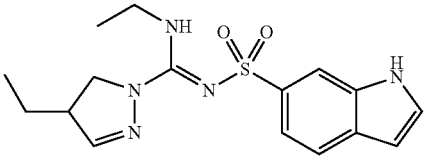 [SMILES: CCN/C(=N\S(=O)(=O)c1ccc2cc[nH]c2c1)N1CC(CC)C=N1] | 2 | | 1.70 | | | |
| 35 | 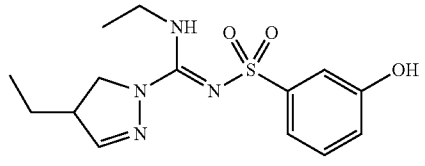 [SMILES: CCN/C(=N\S(=O)(=O)c1cccc(O)c1)N1CC(CC)C=N1] | 2 | | 1.49 | | 7.9 | 7.7 |
| 36 | 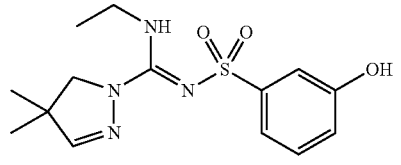 [SMILES: CCN/C(=N\S(=O)(=O)c1cccc(O)c1)N1CC(C)(C)C=N1] | 2 | 0.15 (a) | 1.49 | | 7.5 | 7.3 |

-continued

| Comp | structure | S* | TLC R_f(X) | LCMS R_t | m.p. °C. | 5-HT_6 pA_2 | pK_i |
|---|---|---|---|---|---|---|---|
| 37 | | 2 | | 1.64 | | | |
| 38 | | 2 | 0.10 (b) | | | | |
| 39 | | 2 | | 1.00 | | | |
| 40 | | 1 | | 1.54 | | | 6.2 |
| 41 | | 2 | | 0.84 | | | |
| 42 | | 2 | 0.09 (j) | 0.93 | | | |
| 43 | | 2 | | 1.32 | 146-149 | | |
| 44 | | 2 | | 1.37 | 164-168 | | |

-continued
| Comp | structure | S* | TLC R_f(X) | LCMS R_t | m.p. °C. | 5-HT$_6$ pA$_2$ | pK$_i$ |
|---|---|---|---|---|---|---|---|
| 45 | 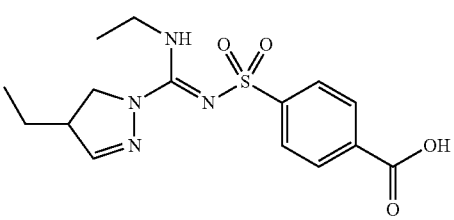 [SMILES: CCN/C(=N\S(=O)(=O)c1ccc(C(=O)O)cc1)N1CC(CC)C=N1] | 2 | | 1.09 | | | |
| 46 | 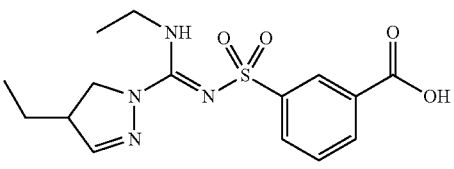 [SMILES: CCN/C(=N\S(=O)(=O)c1cccc(C(=O)O)c1)N1CC(CC)C=N1] | 2 | | 1.14 | | | |
| 47 | 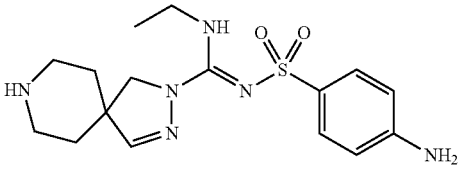 [SMILES: CCN/C(=N\S(=O)(=O)c1ccc(N)cc1)N1CC2(C=N1)CCNCC2] | 1 | | 0.80 | | 8.6 | |
| 48 | 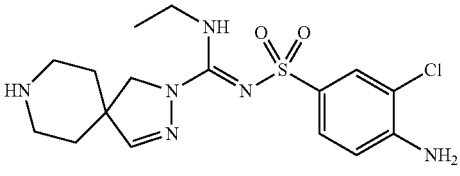 [SMILES: CCN/C(=N\S(=O)(=O)c1ccc(N)c(Cl)c1)N1CC2(C=N1)CCNCC2] | 1 | | 0.90 | | | |
| 49 | 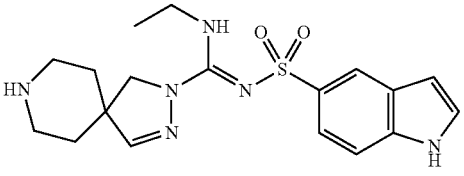 [SMILES: CCN/C(=N\S(=O)(=O)c1ccc2[nH]ccc2c1)N1CC2(C=N1)CCNCC2] | 1 | 0.15 (h) | 0.89 | | 8.8 | |
| 50 | 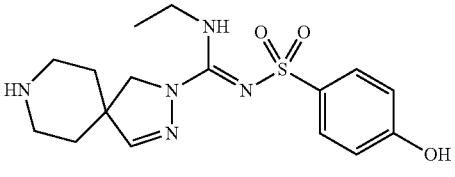 [SMILES: CCN/C(=N\S(=O)(=O)c1ccc(O)cc1)N1CC2(C=N1)CCNCC2] | 1 | 0.34 (i) | 0.84 | | | 7.9 |
| 51 | 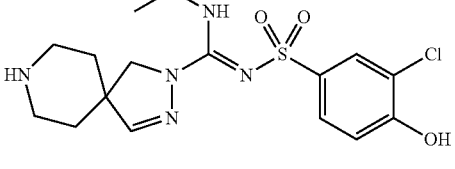 | 1 | 0.48 (i) | 1.00 | | | |

-continued

| Comp | structure | S* | TLC R_f(X) | LCMS R_t | m.p. °C. | 5-HT_6 pA_2 | pK_i |
|---|---|---|---|---|---|---|---|
| 52 | | 1 | 0.20 (f) | 1.04 | 112-114 | | 8.1 |
| 53 | | 2 | | 1.71 | 146-147 | | 8.3 |
| 54 | | 2 | | 1.84 | 157-158 | | |
| 55 | | 1 | | 1.94 | | 9.7 | |
| 56 | | 1 | | 1.48 | | | 7.8 |
| 57 | | 1 | 0.12 (g) | 1.61 | | 8.6 | 8.1 |
| 58 | | 1 | 0.20 (g) | 1.75 | | | |

-continued

| Comp | structure | S* | TLC R_f(X) | LCMS R_t | m.p. °C. | 5-HT_6 pA_2 | pK_i |
|---|---|---|---|---|---|---|---|
| 59 | | 1 | | 1.76 | | | 8.1 |
| 60 | | 1 | 0.50 (d) | 1.85 | | | 8.5 |
| 61 | | 2 | 0.40 (k) | | | | |
| 62 | | 2 | 0.20 (b) | | | | |
| 63 | | 2 | 0.33 (c) | 1.56 | | | |
| 64 | | 2 | 0.21 (l) | 1.89 | | | |

S* = synthetic route; either 'route 1' or 'route 2' as described above.

$R_f(x)$ = $R_f$-value (x) between brackets: TLC mobile phase: (a) = DCM:MeOH = 98:2; (b) = DCM:MeOH = 99:1; (c) = EA; (d) = DCM:MeOH = 95:5; (e) = EA:PA = 2:1; (f) = DCM:MeOH:NH_4OH = 85:15:1; (g) = EA:PA = 1:1; (h) = EA:MeOH:Et_3N = 45:50:5; (i) = MeOH:Et_3N = 95:5; (j) = MeOH:Et_3N = 97:3; (k) = DCM/MeOH/NH_4OH = 92:7.5:0.5; (l) = Et_2O.

$R_t$ = retention time (in minutes) in LC-MS analysis

The specific compounds of which the synthesis is described above are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

EXAMPLE 5

Pharmacological Methods

In Vitro Affinity for Human 5-HT$_6$ Receptors

Affinity for human 5-HT$_6$ receptors was measured in a membrane preparation of CHO-cells transfected with human 5-HT$_6$ receptors by binding studies using [$^3$H]-N-Methyl-Lysergic acid diethylamide ([$^3$H]-LSD) as ligand. The membrane preparation was prepared from cells supplied by Euroscreen (Brussels). CHO/Gα16/mtAEQ/h5HT6-A1 cells were grown in T-flasks in CHO-S-SFM II medium (Gibco BRL), supplemented with 1% dialysed FCS, 2 mM L-glutamine, Geneticin 500 µg/ml and Zeocin 200 µg/ml. Cells were harvested using 0.25% Trypsin (1 ml/T175-flask), centrifuged and subsequently suspended in CHO-S-SFM II medium and frozen at −80° C. After thawing cells were centrifuged during 3 minutes at 1500 g at 4° C. From the pellet, cell membranes were prepared by two cycles of homogenization (Potter-Elvehjem 10 strokes, 600 rpm) and centrifugation (40,000 g for 15 min, 4° C.). The assay was established so as to achieve steady state conditions and to optimize specific binding. For the 5-HT$_6$ receptor, membranes from $5 \cdot 10^5$ cells were incubated with 5.0 nM [$^3$H]-LSD at 37° C. for 30 minutes. Nonspecific binding was determined using $10^{-5}$ M serotonin. Assays were terminated by vacuum filtration through glass fibre filters (GF/B) which had been pretreated with 0.5% polyethyleneimine. Total and bound radioactivity was determined by liquid scintillation counting. Greater than 80% specific binding was achieved in each of these assays. Compounds were tested at a 4 log concentration range; all determinations were performed as triplicates. IC$_{50}$ values were determined by non-linear regression analysis using Hill equation curve fitting. The inhibition constants (K$_i$-values) were calculated from the Cheng-Preushoff equation:

$$K_i = IC_{50} : (1 + L/K_d)$$

wherein L represents the concentration [$^3$H]-LSD in the assay, and K$_d$ its affinity for the receptor. Results are expressed as pK$_i$-values, means±SD of at least three separate experiments.

In Vitro Functional Activity ((Ant)Agonism) on Human 5-HT$_6$ Receptors

The CHO-human-5HT$_6$-Aeqorin assay was bought from Euroscreen, Brussels (Euroscreen, Technical dossier, Human recombinant serotonin 5-HT$_6$-A1 receptor, DNA clone and CHO AequoScreen™ recombinant cell line, catalog no: ES-316-A, February 2003). Human-5-HT$_6$-Aequorin cells express mitochondrial targeted apo-Aequorin. Cells have to be loaded with coelanterazine, in order to reconstitute active Aequorin. After binding of agonists to the human 5-HT$_6$ receptor the intracellular calcium concentration increases and binding of calcium to the apo-Aequorin/coelenterazine complex leads to an oxidation reaction of coelenterazine, which results in the production of apo-Aequorin, coelenteramide, CO$_2$ and light ($\lambda_{max}$ 469 nm). This luminescent response is dependent on the agonist concentration. Luminescence is measured using the MicroBeta Jet (Perkin Elmer). Agonistic effects of compounds are expressed as pEC$_{50}$. Antagonistic effects of compounds were determined as inhibition of $10^{-8}$ M α-methylserotonin induced luminescence and the pA$_2$ was calculated according to Cheng-Preushoff equation. Compounds were tested at a 5 log concentration range, and 3 independent experiments were performed in duplicate.

In Vitro Determination of Metabolic Stability in the Presence of Human/Rat Hepatocytes To obtain an in vitro estimate of biological half-life (t$_{1/2}$), compounds were incubated at 37° C., in 96-well plates, in WME-medium containing 5 µg/ml insulin, during 0, 10, 20, 40 or 60 minutes, with human or rat hepatocytes (50,000 per well), in waterbath, under an atmosphere of oxygen, containing 4-7% CO$_2$. Test compounds were dissolved in DMSO (1 mg/ml). Testconcentrations were 1 µg/ml. To avoid toxic effects on hepatocytes, test concentrations DMSO never exceeded 0.1% of the testvolume. After the incubation period, 96-well plates were put on ice, to each well 100 µl ice cold CAN was added, after which plates were vortexed and centrifuged at 2,500 rpm, at 4° C., for 5 minutes. Next, the supernatant from each well was pipetted off, and into a collection plate, put on ice, covered with a rubber cover, and stored at −80° C. until analysis by HPLC-MS.

HPLC-MS Analysis:

Possible reduction of the concentration of test compounds was measured using an Agilent series 1100 LC-MSD. Dependant of the structure of the test compound either MH$^+$ or (M−H)$^−$ was measured. Prior to analysis samples were allowed to warm (from −80° C.) to room temperature, after which they were homogenized by vortexing for a few seconds. Next, samples were centrifuged at 3,500 rpm, at 4° C., for 10 minutes. Samples were injected into a single quadrupole HPLC-MS system, using a gradient in order to achieve chromatographic separation. In the mass spectrometer, ionization was achieved by ESI, followed by analysis of the formed ions by SIM. For each compound a full scan (100-1000 m/z) was measured. The 'area's under the curve' at the different incubation times were integrated, and plotted against (incubation) time, yielding t$_{1/2}$. Experimental details were as follows:

Eluent A: 0.77 g ammoniumacetate+800 ml water+100 ml methanol+100 acetonitril
Eluent B: 0.77 g ammoniumacetate+100 ml water+100 ml methanol+800 acetonitril Pump Gradient Table:

| Time (min) | Eluent A (%) | Eluent B (%) | Flow (ml/min) |
|---|---|---|---|
| 0.00 | 100 | 0 | 1 |
| 3.60 | 0 | 100 | 1 |
| 7.20 | 0 | 100 | 1 |
| 8.50 | 100 | 0 | 1 |
| 11.00 | 100 | 0 | 1 |

| | |
|---|---|
| column: | Pre-column Chromsep Guard Column SS 10 × 2 mm (CP28141) |
| | Inertsil 5 ODS-3 100 × 3.0 mm (CP22234) |
| | Column temperature 25° C. |
| Injection: | Wellplate temperature 4° C. |
| | Injection volume: 20 µL |
| | Splitter (post column) 1:4 |
| | Total run time 11.0 min |
| Detection SIM: | MH$^+$, (M − H)$^−$, obtained from full scan recording |
| | ESI (pos/neg) spray 4.0 kV |
| | Fragmentor 70 |
| | Gain 2.0 |
| | Dwell 700 msec. |
| | Nebulizer pressure 42 psi. |
| | Drying Gas Temperature 325° C. |
| | Capillary temperature 325° C. |

EXAMPLE 6

Effect of H-Bond Donor on Activity and Metabolic Stability

| Compound | structure | pharmacology 5-HT$_6$ | | stability halflife (t½) minutes | |
|---|---|---|---|---|---|
| | | pA$_2$ | pK$_i$ | human | rat |
| 175 from WO 2008/034863 | | 6.9 | 7.2 | 1,028 | 34 |
| 3 | | 7.6 | 7.9 | >1,000 | 71 |
| 22 | | 8.3 | 7.9 | 1,444 | 33 |
| 33 from WO 2008/034863 | | 7.8 | 7.6 | 61 | 18 |
| 13 | | 8.5 | 8.2 | 700 | 22 |
| 49 from WO 2008/034863 | | 8.2 | 8.3 | 33 | 12 |
| 14 | | 9.0 | 8.8 | 51 | 17 |

-continued

| Compound | structure | pharmacology 5-HT$_6$ | | stability halflife (t½) minutes | |
|---|---|---|---|---|---|
| | | pA$_2$ | pK$_i$ | human | rat |
| 81 from WO 2008/034863 | [structure with NH, ethyl, pyrazole, sulfonyl, phenyl-OCH$_3$] | 7.0 | 7.2 | 68 | 16 |
| 19 | [structure with NH, ethyl, pyrazole, sulfonyl, phenyl-OH] | 8.6 | 8.5 | 354 | 19 |

The comparative data shown in table above clearly indicate that the compounds of the present invention, substituted in the phenyl ring with additional H-bond donating groups, such as —NH$_2$ or —OH, have higher half-life times in the presence of hepatocytes, and/or higher affinity and functional activity, than the structurally closely related compounds disclosed in WO 2008/034863, without H-bond donating groups.

EXAMPLE 8

Pharmaceutical Preparations

For clinical use, compounds of formula (1) are formulated into pharmaceutical compositions that are important and novel embodiments of the invention because they contain the compounds, more particularly specific compounds disclosed herein. Types of pharmaceutical compositions that may be used include, tablets, chewable tablets, capsules (including microcapsules), solutions, parenteral solutions, ointments (creams and gels), suppositories, suspensions, and other types disclosed herein, or apparent to a person skilled in the art from the specification and general knowledge in the art. The active ingredient for instance, may also be in the form of an inclusion complex in cyclodextrins, their ethers or their esters. The compositions are used for oral, intravenous, subcutaneous, tracheal, bronchial, intranasal, pulmonary, transdermal, buccal, rectal, parenteral or other ways to administer. The pharmaceutical formulation contains at least one compound of formula (1) in admixture with a pharmaceutically acceptable adjuvant, diluent and/or carrier. The total amount of active ingredients suitably is in the range of from about 0.1% (w/w) to about 95% (w/w) of the formulation, suitably from 0.5% to 50% (w/w) and preferably from 1% to 25% (w/w).

The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets. A tablet is prepared using the ingredients below:

| Ingredient | Quantity (mg/tablet) |
|---|---|
| COMPOUND No. 4 | 10 |
| Cellulose, microcrystalline | 200 |
| Silicon dioxide, fumed | 10 |
| Stearic acid | 10 |
| Total | 230 |

The components are blended and compressed to form tablets each weighing 230 mg.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol.

If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and 'kits of parts' comprising one or more containers filled with one or more of the ingredients of a pharmaceutical composition of the invention, for use in medical therapy. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human administration. The use of formulations of the present invention in the manufacture of medicaments for use in treating a condition in which antagonism of $5\text{-HT}_6$ receptors is required or desired, and methods of medical treatment or comprising the administration of a therapeutically effective total amount of at least one compound of formula (1) to a patient suffering from, or susceptible to, a condition in which antagonism of $5\text{-HT}_6$ receptors is required or desired.

By way of example and not of limitation, several pharmaceutical compositions are given, comprising preferred active compounds for systemic use or topical application. Other compounds of the invention or combinations thereof, may be used in place of (or in addition to) said compounds. The concentration of the active ingredient may be varied over a wide range as discussed herein. The amounts and types of ingredients that may be included are well known in the art.

BIBLIOGRAPHY

To the extend in which the following references are useful to one skilled in the art, or to more fully describe this invention, they are incorporated herein by reference. Neither these, nor any other documents or quotes cited herein, nor citations to any references, are admitted to be prior art documents or citations.

Bentley, J. C. et al. (1997) J. Psychopharmacol. Suppl. A64, 255
Bentley, J. C. et al. (1999$^a$) Br J Pharmacol. Suppl. 126, P66
Bentley, J. C., et al. (1999$^b$). Br J Pharmacol 126(7): 1537-42
Berge, S. M.: "*Pharmaceutical salts*", J. Pharmaceutical Science, 66, 1-19 (1977).
Bickel, M. H.: "*The pharmacology and Biochemistry of N-oxides*", Pharmacological Reviews, 21(4), 325-355, 1969.
Byrn et al., Pharmaceutical Research, 12(7), 945-954, 1995.
Kohen, R., et al. (1996). J Neurochem 66(1): 47-56
Maleczka Jr., R. E., Shi, F., Holmes, D. and Smith III, M. R., J. Am. Chem. Soc., 2003, 125, 7792-7793.
Martin, E. W. (Editor), "*Remington: The Science and Practice of Pharmacy*", Mack Publishing Company, 19$^{th}$ Edition, Easton, Pa., Vol 2., Chapter 83, 1447-1462, 1995.
Rogers, D. C., et al. (1999). Br J Pharamcol 127(suppl.). 22P
Roth, B. L., et al. (1994). J Pharmacol Exp Ther 268(3): 1403-10
Ruat, M. et al. (1993) Biochem. Biophys. Res. Commun. 193: 268-276
Sebben, M. et al. (1994) NeuroReport 5: 2553-2557
Sleight, A. J., et al. (1998). Br J Pharmacol 124(3): 556-62
Woolley M. L. et al. (2001) Neuropharmacology 41: 210-219
WO 2008/034863 (=PCT/EP2007/059944)

The invention claimed is:
1. A method of treating a condition in a patient in need thereof comprising administering to the patient a therapeutically effective amount of a compound of formula (1):

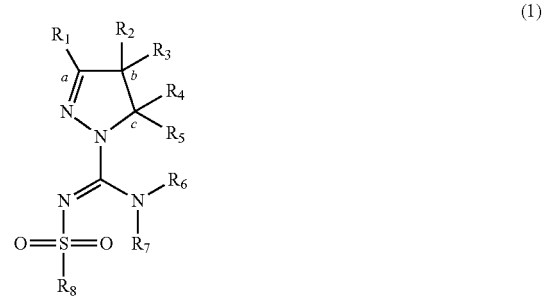

(1)

or a tautomer, stereoisomer, N-oxide, or a pharmacologically acceptable salt of any of the foregoing, wherein:
$R_1$ is chosen from hydrogen and an alkyl($C_{1-4}$) group optionally substituted with at least one substituent chosen from halogen and a hydroxyl group;
$R_2$ and $R_3$ are independently chosen from hydrogen, a hydroxyl group, and an alkyl($C_{1-4}$) group optionally substituted with at least one substituent Q, wherein each Q is independently chosen from: halogen, alkyl($C_{1-4}$), alkenyl($C_{1-4}$), alkynyl($C_{1-4}$), $CF_3$, $NH_2$, NHalkyl($C_{1-4}$), N[alkyl($C_{1-4}$)]$_2$, OH, =O, O-alkyl($C_{1-4}$), and $OCF_3$,
$R_1$ and $R_2$, together with the carbon atoms marked 'a' and 'b', form a $C_{5-8}$-cycloalkyl ring, optionally substituted with at least one substituent chosen from halogen, a hydroxyl group, and an alkyl($C_{1-4}$) group, or
$R_2$ and $R_3$, together with the carbon atom marked 'b', form a $C_{3-8}$-cycloalkyl or a $C_{4-8}$-heterocycloalkyl ring, optionally substituted with at least one substituent Q, as defined above;
$R_4$ and $R_5$ are independently chosen from hydrogen and an alkyl($C_{1-4}$) group optionally substituted with at least one substituent Q, as defined above,
$R_4$ and $R_5$ are independently chosen from a monocyclic or fused bicyclic aromatic or hetero-aromatic groups, optionally substituted with at least one substituent Q, as defined above, or
$R_3$ and $R_4$, together with the carbon atoms marked 'b' and 'c,' form a $C_{3-8}$-cycloalkyl or a $C_{5-8}$-heterocycloalkyl ring, optionally substituted with at least one substituent Q, as defined above;
$R_6$ and $R_7$ are independently chosen from hydrogen, an alkyl($C_{1-4}$) group optionally substituted with at least one substituent chosen from halogen atom, a hydroxyl group, and a dialkyl($C_{1-3}$)-amino-alkyl($C_{1-3}$) group,
$R_6$ and $R_7$ are independently chosen from a monocyclic or fused bicyclic aromatic or hetero-aromatic group optionally substituted with at least one substituent Q, as defined above, R<sub>6</sub> and R<sub>7</sub> are independently chosen from a $C_{5-8}$-cycloalkyl group and a $C_{5-8}$-heterocycloalkyl group optionally substituted with at least one substituent Q, as defined above, or R<sub>6</sub> and R<sub>7</sub>, together with the nitrogen atom to which they are attached, form a $C_{5-8}$-heterocycloalkyl group optionally substituted with at least one substituent Q, as defined above;

$R_8$ is chosen from:

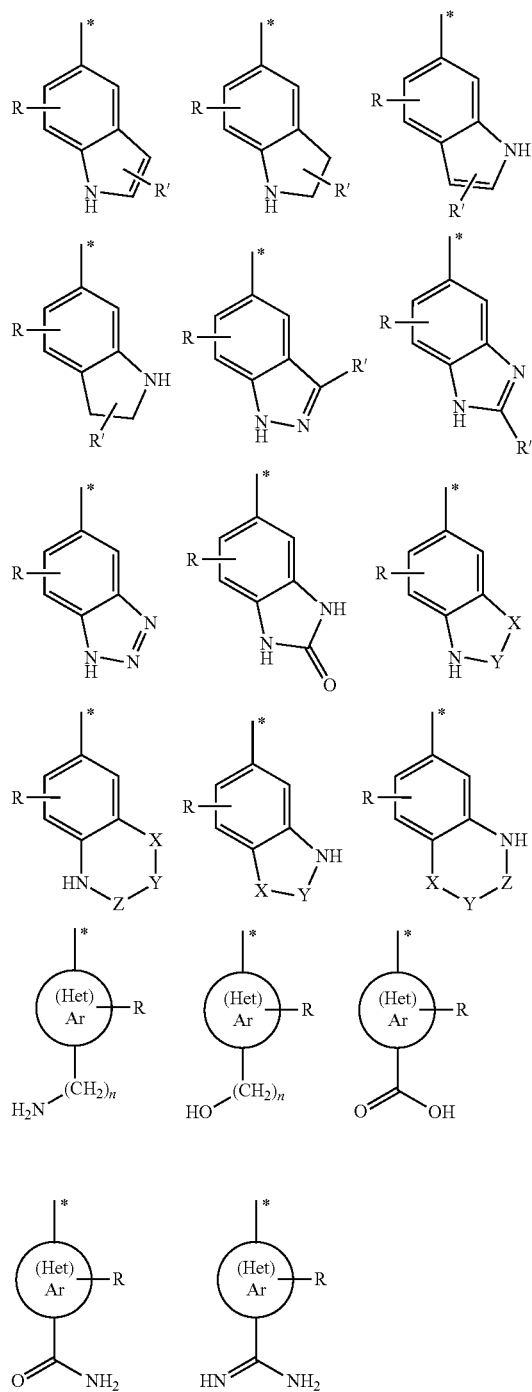

wherein:
an asterisk (*) marks the bond to the S-atom,
n is 0 or 1,

is chosen from an aryl and heteroaryl group,
X, Y and Z are independently chosen from C, N, O and S, with the proviso that bonds in the ring with X, Y, and Z are single or double bonds, any X, Y, or Z that is C or N is substituted with H-atoms only, and
R and R' are independently chosen from hydrogen, halogen, alkyl($C_{1-4}$), alkenyl($C_{1-4}$), alkynyl($C_{1-4}$), $CF_3$, $NH_2$, NHalkyl($C_{1-4}$), N[alkyl($C_{1-4}$)]$_2$, OH, SH, keto, O-alkyl($C_{1-4}$), S-alkyl($C_{1-4}$), SO-alkyl($C_{1-4}$), $SO_2$-alkyl($C_{1-4}$), $OCF_3$, nitro and cyano,
with the proviso that the compounds of formula (1) are not:

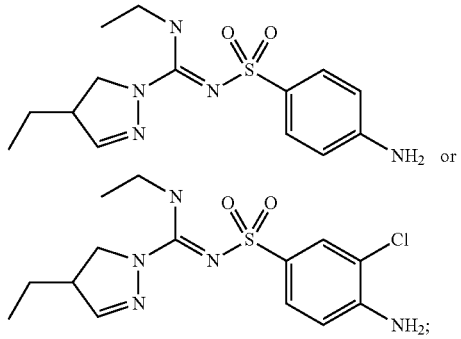

wherein the condition is chosen from Huntington's chorea, anxiety, depression, manic depression, psychoses, epilepsy, obsessive compulsive disorders, mood disorders, migraine, mild cognitive impairment, sleep disorders, eating disorders, anorexia, bulimia, binge eating disorders, panic attacks, akathisia, attention deficit hyperactivity disorder, attention deficit disorder, withdrawal from abuse of cocaine, ethanol, nicotine or benzodiazepines, pain, disorders associated with spinal trauma or head injury, hydrocephalus, functional bowel disorder, Irritable Bowel Syndrome, and type-2 diabetes.

2. The method of claim 1, wherein:
$R_1$, $R_4$ and $R_6$ are hydrogen;
$R_2$ and $R_3$ are independently chosen from hydrogen, a hydroxyl group and an alkyl($C_{1-4}$) group, optionally substituted with at least one substituent Q*, wherein each Q* is independently chosen from: halogen, alkyl ($C_{1-4}$), $NH_2$, NHalkyl($C_{1-4}$), N[alkyl($C_{1-4}$)]$_2$ and OH, or
$R_2$ and $R_3$, together with the carbon atom to which they are attached, form a $C_{3-8}$-cycloalkyl or a $C_{5-8}$-heterocycloalkyl ring optionally substituted with at least one substituent Q* as defined above;
$R_5$ is chosen from hydrogen, an alkyl($C_{1-4}$) group optionally substituted with at least one substituent Q* as defined above, and a monocyclic aromatic or heteroaromatic group optionally substituted with at least one substituent Q* as defined above;
$R_7$ is chosen from hydrogen, an unsubstituted alkyl($C_{1-4}$) group optionally substituted with at least one halogen atom, and a hydroxyl group; and R₈ is chosen from:
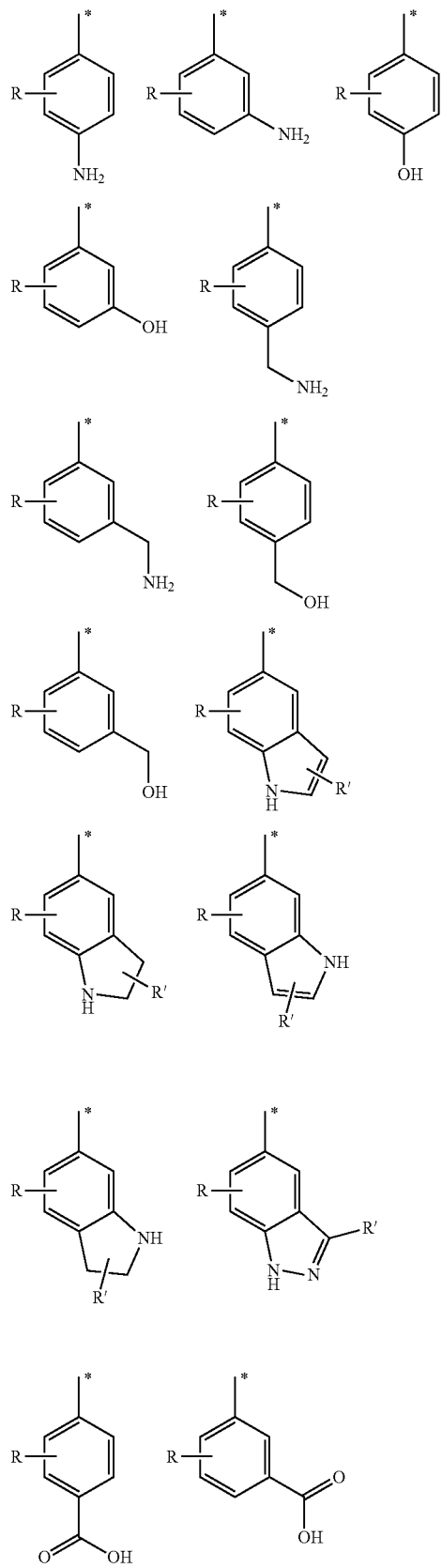
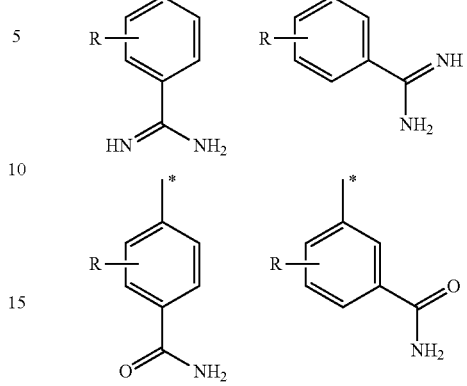
with the proviso that the compound of formula (1) is not:
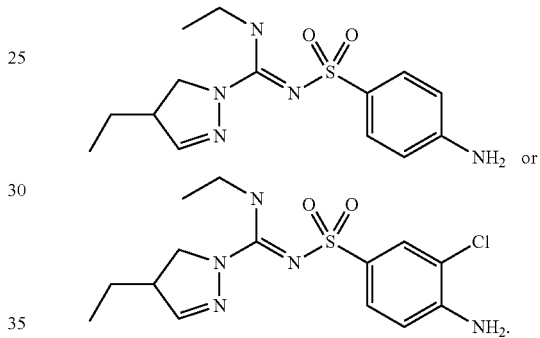
3. The method of claim 1, wherein the compound is selected from:
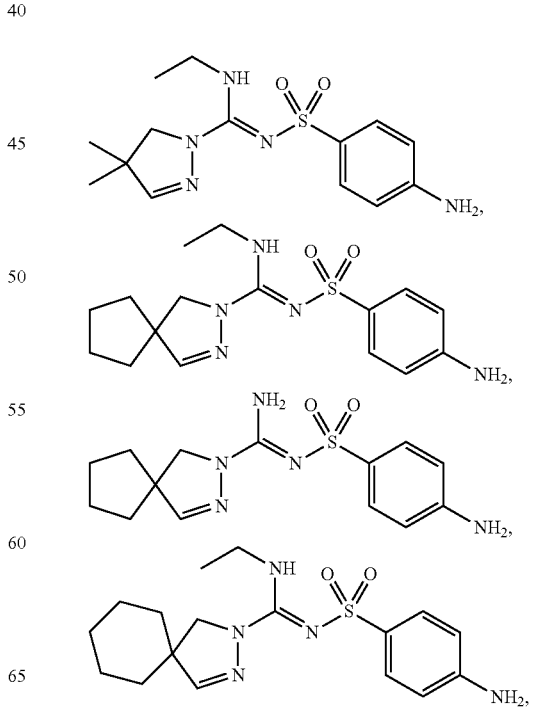

-continued

[chemical structure]

[chemical structure]

[chemical structure]

[chemical structure]

[chemical structure]

[chemical structure] or a pharmaceutically acceptable salt of any of the foregoing.

4. The method of claim 3, wherein the compound is:

[chemical structure]

or a pharmaceutically acceptable salt thereof.

5. The method of claim 3, wherein the compound is:

[chemical structure]

or a pharmaceutically acceptable salt thereof.

6. The method of claim 3, wherein the compound is:

[chemical structure]

or a pharmaceutically acceptable salt thereof.

7. The method of claim 3, wherein the compound is:

[chemical structure]

or a pharmaceutically acceptable salt thereof.

8. The method of claim 3, wherein the compound is an optically active enantiomer.

9. The method of claim 3, further comprising at least one additional therapeutic agent.

10. The method of claim 1, wherein the condition is anxiety.

11. The method of claim 1, wherein the condition is a psychosis.

12. The method of claim 1, wherein the condition is a mood disorder.

13. The method of claim 1, wherein the condition is withdrawal from abuse of cocaine.

14. The method of claim 1, wherein the condition is withdrawal from abuse of ethanol.

15. The method of claim 1, wherein the condition is withdrawal from abuse of nicotine.

16. The method of claim 1, wherein the condition is withdrawal from abuse of benzodiazepines.

17. The method of claim 1, wherein the condition is epilepsy.

18. The method of claim 1, wherein the condition is a sleep disorder.

19. The method of claim 1, wherein the condition is chosen from attention deficit hyperactivity disorder and attention deficit disorder.

20. A method of treating a condition in a patient in need thereof comprising administering to the patient a therapeutically effective amount of a compound of formula (1):

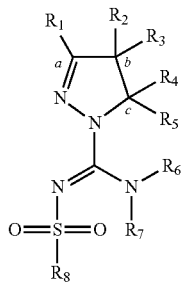
(1)

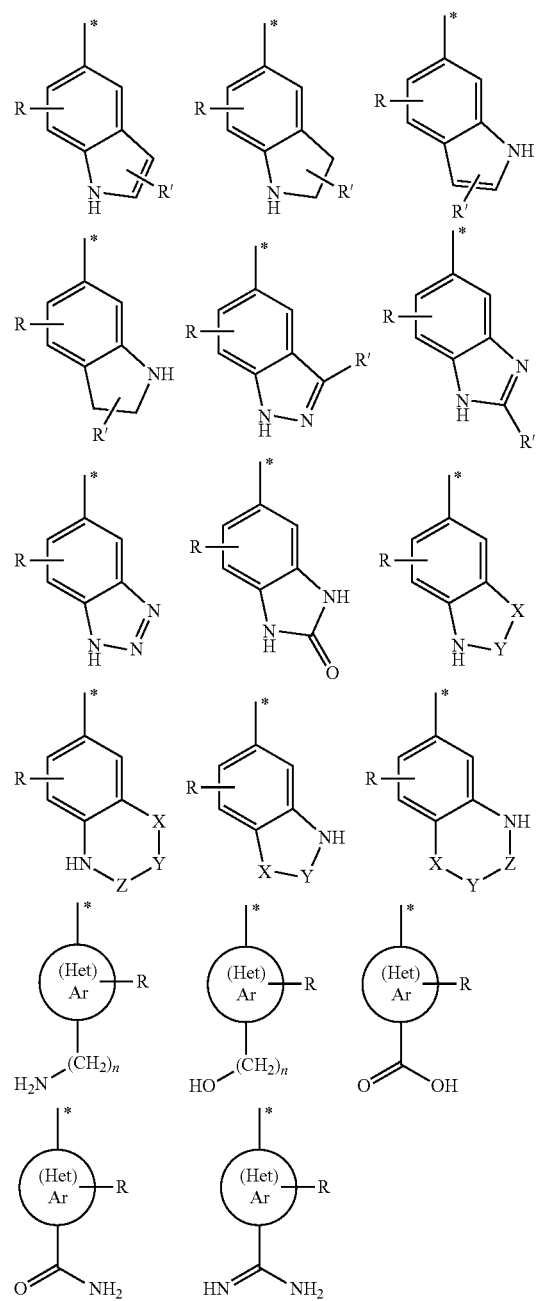

or a tautomer, stereoisomer, N-oxide, or a pharmacologically acceptable salt of any of the foregoing, wherein:

$R_1$ is chosen from hydrogen and an alkyl($C_{1-4}$) group optionally substituted with at least one substituent chosen from halogen and a hydroxyl group;

$R_2$ and $R_3$ are independently chosen from hydrogen, a hydroxyl group, and an alkyl($C_{1-4}$) group optionally substituted with at least one substituent Q, wherein each Q is independently chosen from: halogen, alkyl($C_{1-4}$), alkenyl($C_{1-4}$), alkynyl($C_{1-4}$), $CF_3$, $NH_2$, NHalkyl($C_{1-4}$), N[alkyl($C_{1-4}$)]$_2$, OH, =O, O-alkyl($C_{1-4}$), and $OCF_3$, $R_1$ and $R_2$, together with the carbon atoms marked 'a' and 'b', form a $C_{5-8}$-cycloalkyl ring, optionally substituted with at least one substituent chosen from halogen, a hydroxyl group, and an alkyl($C_{1-4}$) group, or $R_2$ and $R_3$, together with the carbon atom marked 'b', form a $C_{3-8}$-cycloalkyl or a $C_{4-8}$-heterocycloalkyl ring, optionally substituted with at least one substituent Q, as defined above;

$R_4$ and $R_5$ are independently chosen from hydrogen and an alkyl($C_{1-4}$) group optionally substituted with at least one substituent Q, as defined above, $R_4$ and $R_5$ are independently chosen from a monocyclic or fused bicyclic aromatic or hetero-aromatic groups, optionally substituted with at least one substituent Q, as defined above, or $R_3$ and $R_4$, together with the carbon atoms marked 'b' and 'c,' form a $C_{3-8}$-cycloalkyl or a $C_{5-8}$-heterocycloalkyl ring, optionally substituted with at least one substituent Q, as defined above;

$R_6$ and $R_7$ are independently chosen from hydrogen, an alkyl($C_{1-4}$) group optionally substituted with at least one substituent chosen from halogen atom, a hydroxyl group, and a dialkyl($C_{1-3}$)-amino-alkyl($C_{1-3}$) group, $R_6$ and $R_7$ are independently chosen from a monocyclic or fused bicyclic aromatic or hetero-aromatic group optionally substituted with at least one substituent Q, as defined above, $R_6$ and $R_7$ are independently chosen from a $C_{5-8}$-cycloalkyl group and a $C_{5-8}$-heterocycloalkyl group optionally substituted with at least one substituent Q, as defined above, or $R_6$ and $R_7$, together with the nitrogen atom to which they are attached, form a $C_{5-8}$-heterocycloalkyl group optionally substituted with at least one substituent Q, as defined above;

$R_8$ is chosen from:

wherein:

an asterisk (*) marks the bond to the S-atom, n is 0 or 1,

is chosen from an aryl and heteroaryl group,

X, Y and Z are independently chosen from C, N, O and S, with the proviso that bonds in the ring with X, Y, and Z are single or double bonds, any X, Y, or Z that is C or N is substituted with H-atoms only, and R and R' are independently chosen from hydrogen, halogen, alkyl($C_{1-4}$), alkenyl($C_{1-4}$), alkynyl($C_{1-4}$), $CF_3$, $NH_2$, NHalkyl($C_{1-4}$), N[alkyl($C_{1-4}$)]$_2$, OH, SH, keto, O-alkyl($C_{1-4}$), S-alkyl($C_{1-4}$), SO-alkyl($C_{1-4}$), $SO_2$-alkyl ($C_1$-4), $OCF_3$, nitro and cyano, with the proviso that the compounds of formula (1) are not:

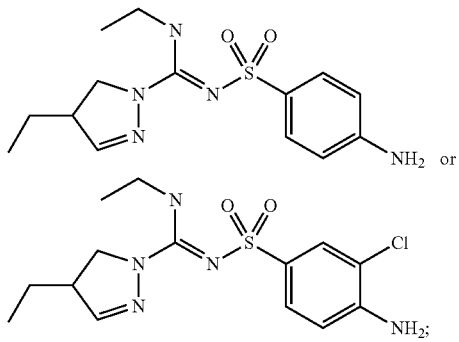

wherein the condition is mild cognitive impairment.

21. A method of treating a condition in a patient in need thereof comprising administering to the patient a therapeutically effective amount of a compound of formula (1):

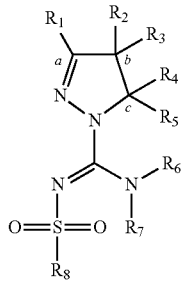

(1)

or a tautomer, stereoisomer, N-oxide, or a pharmacologically acceptable salt of any of the foregoing, wherein:

$R_1$ is chosen from hydrogen and an alkyl($C_{1-4}$) group optionally substituted with at least one substituent chosen from halogen and a hydroxyl group;

$R_2$ and $R_3$ are independently chosen from hydrogen, a hydroxyl group, and an alkyl($C_{1-4}$) group optionally substituted with at least one substituent Q, wherein each Q is independently chosen from: halogen, alkyl($C_{1-4}$), alkenyl($C_{1-4}$), alkynyl($C_{1-4}$), $CF_3$, $NH_2$, NHalkyl($C_{1-4}$), N[alkyl($C_{1-4}$)]$_2$, OH, =O, O-alkyl($C_{1-4}$), and $OCF_3$, $R_1$ and $R_2$, together with the carbon atoms marked 'a' and 'b', form a $C_{5-8}$-cycloalkyl ring, optionally substituted with at least one substituent chosen from halogen, a hydroxyl group, and an alkyl($C_{1-4}$) group, or $R_2$ and $R_3$, together with the carbon atom marked 'b', form a $C_{3-8}$-cycloalkyl or a $C_{4-8}$-heterocycloalkyl ring, optionally substituted with at least one substituent Q, as defined above;

$R_4$ and $R_5$ are independently chosen from hydrogen and an alkyl($C_{1-4}$) group optionally substituted with at least one substituent Q, as defined above, $R_4$ and $R_5$ are independently chosen from a monocyclic or fused bicyclic aromatic or hetero-aromatic groups, optionally substituted with at least one substituent Q, as defined above, or $R_3$ and $R_4$, together with the carbon atoms marked 'b' and 'c,' form a $C_{3-8}$-cycloalkyl or a $C_{5-8}$-heterocycloalkyl ring, optionally substituted with at least one substituent Q, as defined above;

$R_6$ and $R_7$ are independently chosen from hydrogen, an alkyl($C_{1-4}$) group optionally substituted with at least one substituent chosen from halogen atom, a hydroxyl group, and a dialkyl($C_{1-3}$)-amino-alkyl($C_{1-3}$) group, $R_6$ and $R_7$ are independently chosen from a monocyclic or fused bicyclic aromatic or hetero-aromatic group optionally substituted with at least one substituent Q, as defined above, $R_6$ and $R_7$ are independently chosen from a $C_{5-8}$-cycloalkyl group and a $C_{5-8}$-heterocycloalkyl group optionally substituted with at least one substituent Q, as defined above, or $R_6$ and $R_7$, together with the nitrogen atom to which they are attached, form a $C_{5-8}$-heterocycloalkyl group optionally substituted with at least one substituent Q, as defined above;

$R_8$ is chosen from:

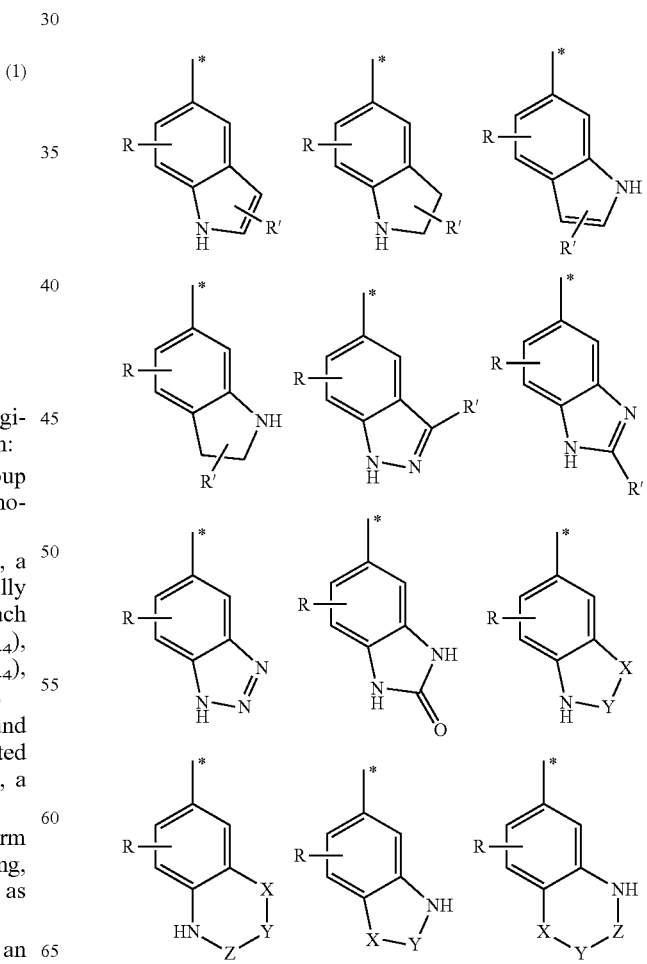

-continued

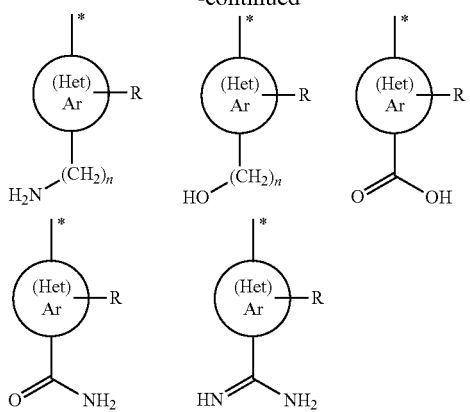

wherein:
an asterisk (*) marks the bond to the S-atom,
n is 0 or 1,

is chosen from an aryl and heteroaryl group,

X, Y and Z are independently chosen from C, N, O and S, with the proviso that bonds in the ring with X, Y, and Z are single or double bonds, any X, Y, or Z that is C or N is substituted with H-atoms only, and R and R' are independently chosen from hydrogen, halogen, alkyl($C_{1-4}$), alkenyl($C_{1-4}$), alkynyl($C_{1-4}$), $CF_3$, $NH_2$, NHalkyl($C_{1-4}$), N[alkyl($C_{1-4}$)]$_2$, OH, SH, keto, O-alkyl($C_{1-4}$), S-alkyl($C_{1-4}$), SO-alkyl($C_{1-4}$), $SO_2$-alkyl ($C_{1-4}$), OCF3, nitro and cyano, with the proviso that the compounds of formula (1) are not:

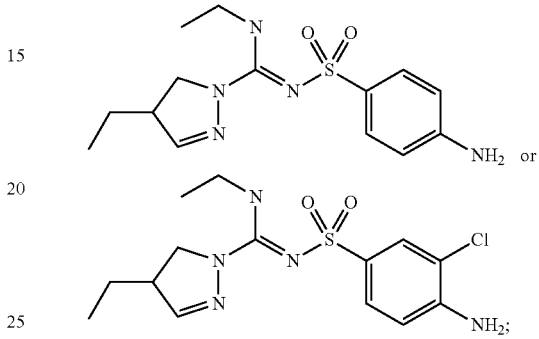

wherein the condition is chosen from depression.

* * * * *